US010385400B2

(12) United States Patent
Zhu et al.

(10) Patent No.: US 10,385,400 B2
(45) Date of Patent: Aug. 20, 2019

(54) METHODS AND KITS FOR MONITORING RESPONSE TO RADIATION THERAPIES IN CANCER

(71) Applicant: RNA Diagnostics Inc., Toronto (CA)

(72) Inventors: Mu Zhu, Waterloo (CA); Amadeo Mark Parissenti, Sudbury (CA); Laura Pritzker, Toronto (CA); Kenneth Pritzker, Toronto (CA); Stacey Santi, Copper Cliff (CA); Baoqing Guo, Sudbury (CA); Xiaohui Wang, Waterloo (CA); Rashmi Narendrula, Sudbury (CA)

(73) Assignee: RNA DIAGNOSTICS INC., Toronto (CA)

( * ) Notice: Subject to any disclaimer, the term of this patent is extended or adjusted under 35 U.S.C. 154(b) by 0 days.

(21) Appl. No.: 14/649,468

(22) PCT Filed: Dec. 3, 2013

(86) PCT No.: PCT/CA2013/001008
§ 371 (c)(1),
(2) Date: Jun. 3, 2015

(87) PCT Pub. No.: WO2014/085909
PCT Pub. Date: Jun. 12, 2014

(65) Prior Publication Data
US 2015/0315656 A1 Nov. 5, 2015

Related U.S. Application Data

(60) Provisional application No. 61/732,697, filed on Dec. 3, 2012, provisional application No. 61/806,222, filed on Mar. 28, 2013.

(30) Foreign Application Priority Data

Apr. 24, 2013 (WO) ................ PCT/CA2013/000408

(51) Int. Cl.
C12Q 1/68 (2018.01)
C12P 19/34 (2006.01)
C12Q 1/6886 (2018.01)
A61N 5/10 (2006.01)
G16B 30/00 (2019.01)
A61K 31/337 (2006.01)

(52) U.S. Cl.
CPC .......... *C12Q 1/6886* (2013.01); *A61K 31/337* (2013.01); *A61N 5/1064* (2013.01); *G16B 30/00* (2019.02); *A61N 5/10* (2013.01); *C12Q 2600/106* (2013.01)

(58) Field of Classification Search
CPC .. C12Q 1/68; C12Q 1/6886; C12Q 2565/125; C12Q 2600/106; C12Q 2600/118; C12Q 2600/142
See application file for complete search history.

(56) References Cited

U.S. PATENT DOCUMENTS 6,251,247 B1 6/2001 Mitsuhashi et al.
7,197,401 B2 3/2007 Hastings
7,504,209 B2 3/2009 Ingham et al.
7,888,035 B2 2/2011 Klass et al.
7,968,291 B2 6/2011 Brees et al.
8,131,473 B1 3/2012 Coffin et al.
2003/0203408 A1 10/2003 Williams et al.
2006/0063170 A1 3/2006 Erlander et al.
2006/0166231 A1 7/2006 Baker et al.
2006/0246577 A1 11/2006 Schroeder et al.
2008/0318801 A1 12/2008 Leung
2010/0057371 A1 3/2010 Denisov
2010/0317001 A1 12/2010 Parissenti et al.
2014/0287063 A1 9/2014 Parissenti et al.
2015/0154350 A1* 6/2015 Pritzker .................. C12Q 1/68
514/459
2015/0315656 A1 11/2015 Zhu et al.
2016/0077051 A1 3/2016 Parissenti et al.
2016/0237506 A1* 8/2016 Pritzker .................. G06F 19/18

FOREIGN PATENT DOCUMENTS

AU 2008295394 B2 3/2009
EP 1772522 4/2007
JP 5602018 B2 12/2010
WO 2004/090780 A2 10/2004
WO 2009/030029 A1 3/2009
WO 2013020201 2/2013
WO 2013/159200 A1 10/2013

OTHER PUBLICATIONS

Shin S. et al. International Journal of Oncology (2009) 35:81-86.*
Burke H.B. et al. Cancer (1998), 82, pp. 874-877.*
Formenti S.C. et al . Int. J. Radiation Oncology Biol. Phys., vol. 52, No. 2, pp. 397-405, 2002.*
Amundson, S.A. et al, Cancer Research, 64, 6368-6371, Sep. 15, 2004.*
Parissenti, A.M. et al. Association of low tumor RNA integrity with response to chemotherapy in breast cancer patients. Breast Cancer Research and Treatment. vol. 119, 2010, pp. 347-356.
Xia, Fen and Powell, Simon N. The molecular basis of radiosensitivity and chemosensitivity in the treatment of breast cancer. Semin Radiat Oncol (2002), 12(4) 296-304. Abstract provided.
Hu, Ze-Ping et al. Metabolomic response of human skin tissue to low dose ionizing radiation. 2012, Mol BioSyst 8; 1979-1986. Abstract provided.
Delic, J. et al., 1993 "Gamma-ray induced transcription and apoptosis-associated loss of 28S rRNA in interphase human lymphocytes". Int J Radiat Biol 64; 39-46. Abstract provided.
Al-Mayah, A.H.J. et al., 2012. "Possible role of exosomes containing RNA in mediating nontargeted effect of ionizing radiation". Radiat Research 177; 539-545. Abstract provided.

(Continued)

*Primary Examiner* — Stephen T Kapushoc
(74) *Attorney, Agent, or Firm* — Carmela De Luca; Tony Orsi; Bereskin & Parr LLP

(57) ABSTRACT

A method of evaluating a cancer cell sample, the method comprising: a. obtaining a cancer cell sample, optionally a breast cancer cell sample or an ovarian cancer cell sample, after the cancer cells have been exposed to a radiation dose; b. assaying the cancer cell sample to obtain a RNA integrity value and/or a RNA concentration of the cancer cell sample.

16 Claims, 15 Drawing Sheets

(56) References Cited

OTHER PUBLICATIONS

Krolak, J.M. et al., 1989. "18S Ribosomal RNA is Degraded during Ribosome Maturation in Irradiated HeLa cells". Radiat Research 118; 330-340. Abstract provided.
Thadani-Mulero, Maria et al. Androgen Receptor on the Move: Boarding the Microtubule Expressway to the Nucleus. Cancer Research, 2012, 72(18), pp. 4611-4615.
Schroeder, A. et al. The RIN: an RNA integrity number for assigning integrity values to RNA measurements. BMC Molecular Biology. 2006, 7:3.
Martinet, W. et al. Reactive oxygen species induce RNA damage in human atherosclerosis. Eruopean Journal of Clinical Investigation, 2004, vol. 34, pp. 323-327.
Yang, Tzu-Hsueh and Chang, Po-Ling. Determination of RNA degradation by capillary electrophoreses with cyan light-emitted diode-induced fluorescence. Journal of Chromatography, Elsevier Science Publishers, vol. 1239, Mar. 21, 2012, pp. 78-84.
Best, Sara et al. Integrity of Prostatic Tissue for Molecular Analysis After Robotic-Assisted Laparoscopid and Open Prostatectomy. Urology, Belle Meadd, vol. 70, No. 2, Aug. 2007, pp. 328-332.
Ganansia-Leymarie, V. et al. Signal transduction pathways of taxane-induced apoptosis. Curr Med. Chem Antica Ag 2003; 3: 291-306.
Cera, C. et al. Interaction between second generation anthracyclines and DNA in the nucleosomal structure, Nucleic Acids Res. 19 (1991) 2309-2314.
Spadari, S. et al. DNA polymerases and DNA topoisomerases as targets for the development of anticancer drugs, Anticancer Res. 6 (1986) 935-940.
Bachur, N.R. et al. Helicase inhibition by anthracycline anticancer agents, Mol.Pharmacol. 41 (1992) 993-998.
Agilent 2100 Bioanalyzer Protocol for RNA 6000 Nano LabChip kit, Jul. 2004 update.
Bulletin 5783 Rev A "Why choose the Experion Automated Eletrophoresis System From Bio-Rad?", Bio-Rad.
Oragene-RNA "Interpreting Bioanalyzer Results for RNA Collected Using Oragene-RNA", 2010 DNA Genotek, PD-WP-017 Issue 1.0.
Benner, "ChIP—Seq Analysis: Finding Peaks (ChIP-enriched Regions), retrieved from internet:" http://biowhat.ucsd.edu/homer/chipseq/peaks.html, retrieved on Mar. 26, 2012 12:34:41 PM.
Degradometer Version 1.4, Software Manual, 2003.
Denisov et al., RNA quality Indicator (RQI)—A New Tool for Assessing RNA Integrity to reliably detect differences in gene expression using qPCR experiments, BIO-RAD, poster.
Freed et al., When ribosomes go bad: diseases of ribosome biogenesis, Mol. BioSyst., 2010, 6, 481-493.
McArthur et al., Targeting Cell Cycle Checkpoints with Specific Inhibitor Drugs, http://www.petermac.org/Research/MolecularOncologyProjects. Accessed Mar. 26, 2012.
Kim et al., A robust peak detection method for RNA structure interference by high-throughput contact mapping, Bioinformatics, vol 25, No. 9, 2009, pp. 1137-1144.
Yoon et al., HiTRACE: High-throughput robust analysis for capillary electrophoresis, Bioinformatics, vol. 00, No. 00 2011, pp. 1-13.
Hatzis et al., Effects of Tissue Handling on RNA Integrity and Microarray Measurements from Resected Breast Cancers, Mar. 21, 2012 104 (6), Abstract.
Denisov et al., Development and Validation of RQI: An RNA Quality Indicator for the Experion Automated Eletrophoresis System, Bulletin 5761, 2008 Bio-Rad Laboratories, Inc.
Belin et al., Dysregulation of Ribosome Biogenesis and Translational Capacity is Associated with Tumor Progression of Human Breast Cancer Cells, Sep. 2009, 4(9), e7147.
Agilent RNA 6000 Nano Kit Quick Start Guide, Agilent Technologies, Edition Apr. 2007.
Auer et al., Chipping away at the chip bias: RNA degradation in microarray analysis, Nature Genetics, Dec. 2003, 35(4)292-293.
Weigelt et al., "Gene expression profiles of primary breast tumors maintained in distant metastases", PNAS, Dec. 23, 2003, 100(26):15901-15905.

Hurvitz et al., "Final Analysis of a Phase II, 3-Arm, Randomized Trial of Neoadjuvant Trastuzumab or Lapatinib or the Combination of Trastuzumab and Lapatinib, Followed by 6 cycles of Docetaxel and Carboplatin with Trastuzumab and/or Lapatinib in Patients with HER2+ Breast Cancer (TRIO-US B07)", San Antonio Breast Cancer Symposium Cancer Therapy and Research Center at UT Health Science Center Dec. 10-14, 2013 (poster).
King, KL et al. 28S ribosime degradation in lymphoid cell apoptosis: evidence for caspase and Bcl-2-dependent and-independent pathways. Cell Death and Differentiation, 2000, vol. 7, pp. 994-1001.
Honaas, Loren et al., A practical examination of RNA isolation methods for European pear (Pyrus communis). BMC Research Notes, 10:237, 2017. (DOI 10.1186/s13104-017-2564-2).
Jamshidi, Neema et al., Genomic Adequacy from Solid Tumor Core Needle Biopsies of ex Vivo Tissue and in Vivo Lung Masses: Prospective Study. Radiology, 2016.
Sellin Jeffries, Marlo K. et al., A comparison of commercially-available automated and manual extraction kits for the isolation of total RNA from small tissue samples. BMC Biotechnology 2014, 14:94.
Kim, Jin-He et al., Comparison of three different kits for extraction of high-quality RNA from frozen blood. SpringerPlus 2014, 3:76.
Yu, Keke et al., Effect of multiple cycles of freeze—thawing on the RNA quality of lung cancer tissues. Cell Tissue Bank (2017) 18:433-40.
Unger, Conny et al., Ultraviolet C radiation influences the robustness of RNA integrity measurement. Electrophoresis 2015, 36, 2072-208.
Toomey, Sinead et al., Correspondence RE: RNA Disruption Assay as a Biomarker of Pathological Complete Response in Neoadjuvant Trastuzumab-Treated Human Epidermal Growth Factor Receptor 2—Positive Breast Cancer. JNCI J Natl Cancer Inst (2016) 108(8).
Trudeau, Maureen, "Response". JNCI J Natl Cancer Inst (2016) 108(8).
Olinski, R. et al. Epirubicin-induced oxidative DNA damage and evidence for its repair in lymphocytes of cancer patients who are undergoing chemotherapy, Mol.Pharmacol. 52 (1997) 882-885.
Vaishampayan, U. et al. Taxanes: an overview of the pharmacokinetics and pharmacodynamics, Urology 54 (1999) 22-29.
Morse, D.L. et al. Docetaxel induces cell death through mitotic catastrophe in human breast cancer cells, Mol.Cancer Ther. 4 (2005) 1495-1504.
Wieder, T. et al. Activation of caspase-8 in drug-induced apoptosis of B-lymphoid cells is independent of CD95/Fas receptor-ligand interaction and occurs downstream of caspase-3, Blood 97 (2001) 1378-1387.
Mueller, 0. et al. RNA Integrity Number (RIN)—Standardization of RNA Quality Control. (2004).
Agilent 2100 Bioanalyzer,Agilent Technologies, Inc.2100 Expert User's Guide. Agilent Technologies Hewlett-Packard Str. 876337 Waldbronn Germany, Agilent Technologies, Inc. Agilent2100 G2946-90004_Vespucci_UG_eBook_(NoSecPack)[2], May 2005.
Wong et al., "Reduced Plasma RNA Integrity in Nasopharyngealcarcinoma Patients", Clinical Cancer Research, Apr. 15, 2006, 12:2512-2516, 12(8).
Parissenti A. M. et al., "Relationship of tumor RNA integrity to clinicopathologic parameters associated with epirubicin/docetaxel chemotherapy", 2007 Breast Cancer Symposium, Sep. 7 and 8, 2007, Abstract No. 107.
Parissenti A. M. et al., "Relationship of tumor RNA integrity to clinicopathologic parameters associated with epirubicin/docetaxel chemotherapy", 2007 Breast Cancer Symposium, Sep. 7 and 8, 2007, (Poster).
Parissenti A. M. et al., "Relationship of tumor RNA integrity to clinicopathologic parameters associated with epirubicin/docetaxel chemotherapy", Nov. 2007, Making Connections: A Canadian Cancer Research Conference Celebrating NCIC's 60th Anniversary, 203-204 (Abstract).
Pandey et al., Induction of the Interferon-Inductible RNA-Degrading Enzyme, RNase L, by Stress-Inducing Agents in the Human Cervical Carcinoma Cells, RNA Biology, May/Jun. 2004, pp. 21-27; 1:1.

(56) References Cited

OTHER PUBLICATIONS

Parissenti et al., "Reductions in Tumor RNA Integrity Associated with Clinical Response to Epirubicin/Docetaxel Chemotherapy in Breast Cancer Patients", Cancer Research 69 [Suppl 2], 378s, 2008.
Balatsos et al., "Drug action on poly(A) polymerase activity and isoforms during U937 cell apoptosis", Journal of Experimental and Clinical Cancer Research, Jan. 1, 2001, 20(1):63-69.
Ogston et al., "A new histological grading system to assess response of breast cancers to primary chemotherapy: Prognostic significance and survival", Breast, Oct. 2003, 12(5):320-327.
Carey et al., "Telomerase activity and prognosis in primary breast cancers", Journal of Clinical Oncology, Oct. 1999, 17(10):3075-3081.
Imbeaud et al., "Towards standardization of RNA quality assessment using user-independent classifiers of microcapillary electrophoresis traces", Nucleic Acids Research, 2005, 33(6):e56, doi:10.1093/nar/gni054.
Wong et al. "Plasma RNA integrity analysis: methodology and validation", Annals of the New York Academy of Sciences, 2006, 1075:174-178.
Minotti et al., "Anthracyclines: molecular advances and pharmacologic developments in antitumor activity and cardiotoxicity", Pharmacol Rev, 2004, 56:185-229.
Parissenti A. M. et al., "Relationship of tumor RNA integrity to clinicopathologic parameters associated with epirubicin/docetaxel chemotherapy", Internet Citation, Sep. 7, 2007 (Sep. 7, 2007), pp. 1-4.
Strand, Carina et al. RNA quality in frozen breast cancer samples and the influence on gene expression analysis—a comparison of three evaluation methods using microcapillary electrophoreses traces. BMC Molecular Biology 2007, 8:38.
Houge, G., et al. Fine Mapping of 28S rRNA Sites Specifically Cleaved in Cells Undergoing Apoptosis. Molecular and Cellular Biology, Apr. 1995, vol. 15, No. 4, pp. 2051-2062.
Hoat, Trinh X., et al. Specific cleavage of ribosomal RNA and mRNA during victorin-induced apoptotic cell death in oat. The Plant Journal (2006) 46, pp. 922-933.
Marx, Vivien. RNA Quality: Defining the Good, the Bad, & the Ugly. Genomics Proteomics. Retrieved from Internet www.dnaarrays.org/P_GenProMag.pdf May 4, 2005.
King, KL et al. 28S ribosome degradation in lymphoid cell apoptosis: evidence for caspase and Bcl-2 dependent and independent pathways. Cell Death and Differentiation (2000) 7, 994-1001.
Fimognari, Carmela et al. Protective effect of creatine against RNA damage. Mutation Research 670 (2009) 59-67.
Fimognari, Carmela et al. Corrigendum to "Protective effect of creatine against RNA damage". Mutation Research. 670 (2009) 59-67.
Copois, Virginie et al. Impact of RNA degradation on gene expression profiles: Assessment of different methods to reliably determine RNA quality. Journal of Biotechnology 127 (2007) 549-559.
Banerjee et al., "RNase L-independent specific 28S rRNA cleavage in murine coronavirus-infected cells", Journal of Virology, Oct. 2000, pp. 8793-8780, 74(19).
Kemp et al., "p53 induction and apoptosis in response to radio- and chemotherapy in vivo is tumor-type-dependent", Cancer Research, .Jan. 1, 2001, pp. 327-332, 61(1).
Kim et al., "The role of apoptosis in cancer cell survival and therapeutic outcome", Cancer Biology & Therapy, Nov. 2006, pp. 1429-1442, 5:11.
Raman et al., "Quality control in microarray assessment of gene expression in human airway epithelium", BMC Genomics, Oct. 24, 2009, 10:493, doi: 101186/1471-2164-10-493.
Samali et al., "The ability to cleave 28S ribosomal RNA during apoptosis is a cell-type dependent trait unrelated to DNA fragmentation", Cell Death and Differentiation, May 1997, pp. 289-293, 4(4).
Gjertsen, Bjorn Tore et al. Multiple apoptotic death types triggered through activation of separate pathways by cAMP and inhibitors of protein phosphatases in one (IPC leukemia) cell line. Journal of Cell Science 107, 3363-3677, 1994.
Greenhalgh D.A. et al. Effect of 5-fluorouracil combination therapy on RNA processing in human colonic carcinoma cells. Br. J. Cancer, 1990, vol. 61, pp. 415-419.
Cheang, Maggie C. U., et al. Ki67 Index, HER2 Status, and Prognosis of Patients With Luminal B Breast Cancer. J. Natl. Cancer Institute, 2009, 101, pp. 736-750.
Goldhirsch A. et al. Strategies for subtypes—dealing with the diversity of breast cancer: highlights of the St Gallen International Expert Consensus on the Primary Therapy of Early Breast Cancer 2011. Annals of Oncology, vol. 22, pp. 1736-1747, 2011.
Narendrula, Rashmi. Quantitative and qualitative changes in cellular RNA in response of chemotherapy. Oral presentation, Apr. 4, 2012.
Johnson G.D. et al. "Cleavage of rRNA ensures translational cessation in sperm at fertilization, Molecular Human Reproduction", Aug. 2011, pp. 721-726, 17(12).
Fimognari et al., "RNA as a new target for toxic and protective agents", Mutation Research, Sep. 2008, pp. 15-22, 648(1-2).
Telli M. et al., "Insight or Confusion: Survival After Response-Guided Neoadjuvant Chemotherapy in Breast Cancer", Journal of Clinical Oncology, Oct. 2013 pp. 3613-3615, 31(29).
Young, L.E. Zeroing in on cancer. Laurentian University Magazine, Winter 2010, p. 5. Retrieved from the internet <URL:http://www.laurentian.ca/NR/rdonlyres/D6249D37-F645-49F1-8CA0-1EA940D81CB4/0/Winter10_English_low.pdf>.
Hannemann J. et al. Changes in Gene Expression Associated With Response to Neoadjuvant Chemotherapy in Breast Cancer, Journal of Clinical Oncology, May 2005, 3331-3342, 23(15).
Sotiriou et al. Gene expression profiles derived from fine needle aspiration correlate with response to chemotherapy in breast cancer. Breast Cancer Research. 4:R3, Mar. 20, 2002 (8 pages).
Thisted. (1998) What is a P-Value? The University of Chicago, p. 1-6.
Fleige et al. (2006) RNA integrity and the effect on the real-time qRT-PCR performance. Molecular Aspects of Medicine, 27:126-139.
Thuerigen et al. (2006). Gene Expression Signature Predicting Pathologic Complete R esponse with Gemcitabine, Epirubicin, and Docetaxel in Primary Breast Cancer, Journal of Clinical Oncology, 24(12):1839-1845.
Degen et al. (2000) Caspase-dependent cleavage of nucleic acids. Cell Death and Differentiation, 7:616-627.
Fulda et al. (2006) Extrinsic versus intrinsic apoptosis pathways in anticancer chemotherapy. Oncogene, 25:4798-4811.
Kaufman et al. (2000) Induction of Apoptosis by Cancer Chemotherapy. Experimental Cell Research, 256:42-49.
Neschadim Anton et al. Relaxin receptor antagonist AT-001 synergizes with docetaxel in androgen-independent prostate xenografts. Endocrine-Related Cancer, 2014, 21(3):459-71.
Agilent Technologies (Agilent 2100 Bioanalyzer, Expert User's Guide, Copyright 2000, pp. 1-149) (Year: 2000).
Mueller et al., "RNA Integrity Number (RIN)—Standardization of RNA Quality Control", Agilent Technologies, Inc., pp. 1-7. 2016.
Parissenti et al., "Tumor RNA disruption predicts survival benefit from breast cancer chemotherapy", Breast Cancer Res. Treat., 2015, 153(1): 135-144.
Parissenti et al., Gene Expression Profiles as Biomarkers for the Prediction of Chemotherapy Drug Response in Human Tumor Cells, Anticancer Drugs 18(5) (Jun. 2007) 499-523.
Chang et al., Apoptosis and proliferation as predictors of chemotherapy response in patients with breast carcinoma. Cancer 2000, 89(11): 2145-52.
Archer, et al., Early changes in apoptosis and proliferation following primary chemotherapy for breast cancer. Br J Cancer 2003; 89(6): 1035-41.
Narla, et al. Ribosomopathies: human disorders of ribosome dysfunction. Blood 2010, Apr. 22. 115(16): 3196-205.

(56) References Cited

OTHER PUBLICATIONS

Burger, et al., Chemotherapeutic drugs inhibit ribosome biogenesis at various levels. The Journal of Biological chemistry Apr. 16, 2010; 285(16): 12416-25.
Crawford, et al., (1997) 16S mitochondrial ribosomal degradation is associated with apoptosis. Free Rad. Biol. Med. 22(7): 1295-1300.
Swe et al., (2000) zVAD-fmk and DEVD-cho induced late mitotic arrest and apoptotic expressions. Apoptosis 5(1): 29-36.
Cortazar et al. (2014) Pathological complete response and long-term clinical benefit in breast cancer: the CTNeoBC pooled analysis. Lancet vol. 384: 115-116.
Samkari, A., et al. Tumor RNA disruption as a tool to predict response to neoadjuvant chemotherapy in breast cancer: Optimizing timing of biopsy. (2016) Abstract No. P1-09-19 [abstract]. In: Proceedings of the 2016 San Antonio Breast Cancer Symposium; Dec. 6-10, 2016; San Antonio, TX. Philadelphia (PA): AACR; Cancer Res 2017; 77 (4 suppl): Abstract, 5 pages (Year: 2017).
Pritzker K., et al. RNA Disruption and Drug Response in Breast Cancer Primary Systemic Therapy. Journal of the National Cancer Institute, 2015, 51:76-80.
He, Kaiyu et al. Targets and Intracellular Signaling Mechanisms for Deoxynivalenol-Induced Ribosomal RNA Cleavage. Toxicological Sciences, 127(2), 382-390, 2012.
Scholl SM et al. Breast tumours response to primary chemotherapy predicts local and distant control as well as survival. Eur J Ca 1995; 31A: 1969-1995.
Curran W et al. Phase III comparison of sequential versus concurrent chemo-radiation for patients with unresected stage III non-small cell lung cancer (NSCLC): report of Radiation Oncology Group (RTOG) 9410. Lung Ca 2003; 29 (suppl 1): 93, abstract 303.
Bellon JR et al. Concurrent radiation therapy and paclitaxel or docetaxel chemotherapy in high-risk breast cancer. Int J Rad Onc Bio Phys 2000; 48: 393-397.
Chollet P et al. Clinical and pathological response to primary chemotherapy in operable breast cancer. Eur J Ca 1997; 33: 862-866.
Koukourakis MI et al. Weeky docetaxel and concomitant boost radiotherapy for non-small cell lung cancer. A phase I/II dose escalation trial. Eur J Ca 1998; 34: 838-844.
Onishi H et al. Concurrent two-dimensional radiotherapy and weekly docetaxel in the treatment of stage III non-small cell lung cancer: a good local response but no good survival due to radiation pneumonitis. Lung Ca 2003; 40: 79-84.
Adelstein DJ et al. An Intergroup phase III comparison of standard radiation therapy and two schedules of concurrent chemoradiotherapy in patients with unresectable squamous cell head and neck cancer. JCO 2003; 21: 92-98.
Rivera E, Mejia JA, Arun BK, Adinin RB, Walters RS, Brewster A et al. Phase 3 study comparing the use of docetaxel on an every-3-week versus weekly schedule in the treatment of metastatic breast cancer. Cancer 2008; 112 (7):1455-1461.
Bear HD et al. The effect on tumor response of adding sequential preoperative docetaxel to preoperative doxorubicin and cyclophosphamide: preliminary results from National Surgical Adjuvant Breast and Bowel Project protocol B-27. JCO 2003; 21: 4165-4174.
Bissery MC et al. Experimental antitumor activity of Taxotere (RP 56976, NCS 628503) a Taxol analogue. Ca Res 1991; 51: 4845-4852.
Kuerer HM, Newman LA, Smith TL, Ames FC, Hunt KK, Dhingra K et al. Clinical course of breast cancer patients with complete pathologic primary tumor and axillary lymph node response to doxorubicin-based neoadjuvant chemotherapy. J Clin Oncol 1999; 17(2):460-469.
Forastiere AA et al. Concurrent chemotherapy and radiotherapy for organ preservation in advanced laryngeal cancer. NEJM 2003; 349: 2091-2098.
Denis F et al. Final results of the 94-01 French Head and Neck Oncology and Radiotherapy Group randomized trial comparing radiotherapy alone with concomitant radiochemotherapy in advanced-stage oropharynx carcinoma. JCO 2004; 22: 69-76.
Bosset JF et al. Chemotherapy with preoperative radiotherapy in rectal cancer. NEJM 2006; 355: 1114-1123.
Formenti SC, Dunnington G, Uzieli B, Lenz H, Keren-Rosenberg S, Silberman H et al. Original p53 status predicts for pathological response in locally advanced breast cancer patients treated preoperatively with continuous infusion 5-fluorouracil and radiation therapy. Int J Radiat Oncol Biol Phys 1997; 39(5):1059-1068.
Djuzenova CS, et al. Radiosensitivity in breast cancer assessed by the histone γ-H2AX and 53BP1 foci. Radiation Oncology 8:98.
Formenti SC et al. Preoperative twice-weekly paclitaxel with concurrent radiation therapy followed by surgery and postoperative doxorubicin-based chemotherapy in locally advanced breast cancer: a phase I/II trial. JCO 2003; 21: 864-870.
Gazet JC et al. Assessment of the effect of pretreatment with neoadjuvant therapy on primary breast cancer. Br J Ca 1996; 73: 758-762.
Johung et al. A clinical model for identifying radiosensitive tumor genotypes in non-small cell lung cancer 2013 Clin Cancer Res. 19(22).
Martin M et al. Adjuvant docetaxel for node-positive breast cancer. NEJM 2005; 352: 2302-2313.
Mueller, O. et al., A microfluidic system for high-speed reproducible DNA sizing and quantitation. Electrophoresis 21 (2000) 128-134.
Hutcheon AW et al. Improvements in survival in patients receiving primary chemotherapy with docetaxel for breast cancer: a randomized controlled trial. Br Ca Res Tr 2001; 69: 298.
Nabholtz JM et al. Docetaxel and doxorubicin compared with docetaxel and cyclophosphamide as first-line chemotherapy for metastatic breast cancer: results of a randomized, multicenter phase III trial. JCO 2003; 21: 968-975.
Ravdin PM et al. Phase II trial of docetaxel in advanced anthracycline-resistant or anthracenedione-resistant breast cancer. JCO 1995; 13: 2879-2885.
Mauer AM et al. Phase I study of docetaxel with concomitant thoracic radiation therapy. JCO 1998; 16: 159-164.
O'Shaughnessy J et al. Superior survival with capecitabine plus docetaxel combination therapy in anthracycline-pretreated patients with advanced breast cancer; phase III trial results. JCO 2002; 20: 2812-2823.
Valero V et al. Phase II trial of docetaxel: a new highly effective antineoplastic agent in the management of patients with anthracycline-resistant metastatic breast cancer. JCO 1995; 13: 2886-2894.
Nature. Comprehensive molecular portraits of human breast tumours. 490:61-70, Oct. 4, 2012.
Chan S et al. Prospective randomized trial of docetaxel versus doxorubicin in patients with metastatic breast cancer. The 303 Study Group. JCO 1999; 17: 2341-2354.
Posner MR et al. Cisplatin and Fluorouracil alone or with docetaxel in head and neck cancer. NEJM 2007; 357: 1705-1715.
Rodel C et al. Prognostic significance of tumor regression after preoperative chemoradiotherapy for rectal cancer. JCO 2005; 23: 8688-8696.
Sauer R et al. Preoperative versus postoperative chemoradiotherapy for rectal cancer. NEJM 2004; 351: 1731-1740.
Ruyck et al. TGFß1 polymorphisms and late clinical radiosensitivity in patients treated for gynecologic tumors. Int. J. Radiation Oncol. Biol Phys. 2006. 65: 1240.
Roche H et al. Sequential adjuvant epirubicin-based and docetaxel chemotherapy for node-positive breast cancer patients; the FNCLCC PACS 01 trial. JCO 2006; 24: 5664-5671.
Smith IC et al. Neoadjuvant chemotherapy in breast cancer significantly enhanced response with docetaxel. JCO 2002; 20: 1456-1466.
Tabernero J, Climent MA, Lluch A, Albanell J, Vermorken JB, Barnadas A et al. A multicentre, randomised phase II study of weekly or 3-weekly docetaxel in patients with metastatic breast cancer. Ann Oncol 2004; 15(9):1358-1365.

(56) References Cited

OTHER PUBLICATIONS

Von Minckwitz G et al. Doxorubicin with cyclophosphamide followed by docetaxel every 21 days compared with doxorubicin and docetaxel every 14 days as preoperative treatment in operable breast cancer: the GEPARDUO study of the German Breast Group. JCO 2005; 23: 2676-2685.

Handbook, Qiagen. Sample & Assay Technologies, "RNeasy® MinElute® Cleanup Handbook: For RNA cleanup and concentration with small elution volumes", Oct. 1, 2010, pp. 1-32.

* cited by examiner

A)

B)

B)

C)

A)

METHODS AND KITS FOR MONITORING RESPONSE TO RADIATION THERAPIES IN CANCER

CROSS-REFERENCE TO RELATED APPLICATIONS

This application is a national phase entry of PCT/CA2013/001008, filed Dec. 3, 2013, which claims priority from U.S. Provisional patent application serial number 61/732,697 filed Dec. 3, 2012, U.S. Provisional patent application serial number 61/806,222 filed Mar. 28, 2013 and PCT Application serial number PCT/CA2013/000408 filed Apr. 24, 2013; each of these applications being incorporated herein in their entirety by reference.

FIELD

The disclosure relates to methods and kits for evaluating response to radiation in cancer cells and tissues, and to monitoring response of subjects with cancer and particularly breast and ovarian cancer treated with modalities comprising radiation therapy.

INTRODUCTION

PCT application (PCT/CA2008/001561) entitled "Method of Using Tumour RNA Integrity to Measure Response to Chemotherapy in Cancer Patients herein incorporated by reference discloses a method for monitoring response to chemotherapy in patients with locally advanced breast cancer by monitoring the ability of the chemotherapy agents to induce RNA degradation (loss of RNA integrity), as exhibited through a reduction in known metrics of RNA quality, including the RNA integrity number (RIN)[52].

In association with a national clinical trial (CAN-NCIC-CTG-MA.22), it was demonstrated that tumour RNA integrity number (RIN) values fell significantly upon treatment of locally advanced breast cancer patients with epirubicin/docetaxel chemotherapy and this response could be significantly correlated with the dose level of the regimen (p=0.05)[53]. Epirubicin, is an epimer of doxorubicin, and both compounds (known as anthracyclines) intercalate between DNA strands within cells[54]. The drugs also inhibit topoisomerase II[55] and DNA helicase[56], thereby blocking DNA replication. In addition, the drugs are cytotoxic through the generation of free radicals, damaging a variety of macromolecules including DNA and lipids[57]. Docetaxel, in contrast, is an analog of paclitaxel. Both drugs (known as taxanes) bind to microtubules and prevent their depolymerisation[58]. This results in arrest of cell cycle progression at mitosis and mitotic catastrophe[59], and ultimately, the induction of apoptosis[60]. Unlike tumour extent (cellularity) mid-treatment, it was observed in the MA.22 clinical trial that low mid-treatment tumour RIN values were predictive of pathologic complete response following treatment in these patients (p=0.05)[53].

SUMMARY

An aspect includes a method of determining in a radiation treated cancer cell sample, a RNA profile comprising obtaining a cancer cell sample which has received one or more doses of radiation; isolating RNA from the sample, the isolated RNA comprising one or more of radiation induced degraded RNA (e.g disrupted RNA) and/or intact RNA, separating the isolated RNA radiation induced degraded RNA from intact RNA and measuring the amount of radiation induced degraded RNA and/or measuring the amount of intact RNA to provide a RNA profile of the radiation treated cancer cell sample.

In an embodiment, the measuring the amount of radiation induced degraded RNA and/or measuring the amount of intact RNA to provide a RNA profile of the radiation treated cancer cell sample comprises obtaining an electropherogram dataset from which a RNA profile is determined. The profile can comprise features from the electropherogram. In an embodiment, the RNA profile is used to determine an RNA integrity value. The RNA integrity value can be a composite value determined from different regions of the electropherogram.

Another aspect includes a method of evaluating a cancer cell sample optionally selected from a breast cancer cell sample and an ovarian cancer cell sample, the method comprising:
a. assaying the cancer cell sample, optionally a breast cancer cell sample or ovarian cancer cell sample, that has been exposed to a radiation dose to obtain a RNA integrity value and optionally to obtain a RNA concentration of the cancer cell sample;
b. identifying an increase, decrease or absence of change in the RNA integrity value and optionally an increase or decrease or absence of change in the RNA concentration compared to a control; and
c. optionally determining a radiation response score derived from the increase, decrease or absence of change in the RNA integrity value and optionally the increase, decrease or absence of change in the RNA concentration.

In an embodiment, the increase or decrease in the RNA integrity value and optionally the increase or decrease or absence of change in the RNA concentration compared to the control which is used to calculate a radiation response score, indicates if the cancer cell sample is responding to the radiation dose.

In an embodiment the method comprises the step of obtaining the cancer cell sample, optionally a breast cancer cell sample or ovarian cancer cell sample, from a cancer cell source that has been exposed to a radiation dose prior to assaying the cancer cell sample.

Another aspect provides a method of evaluating a cancer cell sample optionally selected from a breast cancer cell sample and an ovarian cancer cell sample, the method comprising:
a. obtaining the cancer cell sample optionally the breast cancer cell sample or the ovarian cancer cell sample from that has been exposed to a radiation dose;
b. assaying the cancer cell sample to obtain a RNA integrity value and optionally measure a RNA concentration of the cancer cell sample;
c. comparing the RNA integrity value and optionally the RNA concentration to a control; and
d. identifying an increase, decrease or absence of change in the RNA integrity value and optionally the RNA concentration compared to the control.

In an embodiment, the method further comprises determining a radiation response score derived from the increase, decrease or absence of change in the RNA integrity value and optionally the increase, decrease or absence of change in the RNA concentration.

A further aspect provides a method of evaluating a cancer cell sample radiation response, the method comprising:

a. obtaining a cancer cell sample, optionally a breast cancer cell sample or an ovarian cancer cell sample, that has been exposed to a radiation dose;
b. assaying the cancer cell sample to obtain a RNA integrity value and optionally a RNA concentration of the cancer cell sample;
c. comparing the RNA integrity value and optionally the RNA concentration to a control;
d. identifying an increase, decrease or absence of change in the RNA integrity value and optionally RNA concentration compared to the control; and
e. determining a radiation response score derived from the increase, decrease or absence of change in the RNA integrity value and optionally the RNA concentration compared to the control.

In an embodiment, the control is one or more predetermined reference values, for example derived from a pretreatment sample or an earlier treatment sample or derived from a group of patients for example in a clinical trial. In an embodiment, the RNA integrity value is proportional to the degree of RNA degradation in the cancer sample. In an embodiment, the RNA integrity value is inverse proportional to the degree of RNA degradation in the cancer sample.

The RNA integrity of RNA in a cancer cell sample can be measured for example by measuring a RNA integrity value. In an embodiment, the RNA integrity value is proportional to the RNA integrity of the sample, for example in such a case a high or increased RNA integrity value corresponds to a high or increased RNA integrity. In an embodiment, the method further comprises comparing the RNA integrity value and optionally the RNA concentration of the cancer cell sample to a control such as one or more response thresholds wherein a decreased RNA integrity value (e.g. increased RNA degradation) and optionally decreased RNA concentration of the cancer cell sample compared to the response threshold is predictive/indicative that the cancer cells or subject are responsive to the radiation therapy and a comparable or an increased RNA integrity value and optionally increased concentration of the cancer cell sample compared to the response threshold is predictive/indicative the cancer cells are unresponsive to the radiation treatment.

In an embodiment, the comparing comprises comparing to a reference electropherogram or a reference RNA integrity value derived therefrom, for example derived from reference patients/cancer cells treated with a reference radiation treatment. Different reference electropherograms or reference RNA integrity values correspond to different radiation treatments (e.g. with or without a cytotoxic therapy such as chemotherapy, the type of cytotoxic therapy, different doses, different schedules etc).

In embodiments wherein the RNA integrity value is inverse proportional, e.g. measured by RDI, a high RNA integrity value is indicative of degraded or low RNA integrity, and a decreased RNA integrity value compared to the control (optionally one or more response thresholds) is predictive/indicative that the cancer cells are (or the subject is) unresponsive to the radiation treatment and an increased RNA integrity value compared to the control (e.g. one or more response thresholds) is predictive/indicative that the cancer cells are (or the subject is) responsive to the radiation treatment.

In an embodiment, the cancer cells have (and/or the patient has) received 1, 2, 3, 4, 5, 6 or more doses of radiation.

In another embodiment, the cancer cells are (and/or the patient is) treated with a dose of a chemotherapeutic agent prior to and/or concurrent with radiation treatment.

In an embodiment, the chemotherapeutic agent is selected from taxane chemotherapeutics, anthracyclines and combinations thereof.

In a further embodiment, the taxane is selected from paclitaxel, docetaxel, larotaxel, Abraxane, docoxahexaenoic acid-linked paclitaxel, paclitaxel polyglumex, Ortataxel, Genexol, liposomal-encapsulated paclitaxel, and paclitaxel in a Vitamin E emulsion.

In an embodiment, the cancer cell sample is obtained, during for example after a first dose of radiation or post treatment.

In another embodiment, the subject is administered a radiosensitizing or radioprotecting compound, for example prior to obtaining the cancer cell sample. For example the subject can be administered a radiosensitizing compound such as a taxane and/or a platinum compound, optionally systemically or remotely. Typically, the dose of the radiosensitizing agent such as a taxane is reduced compared to in the absence of radiation.

In an embodiment, the cancer cells (e.g. the cancer source) is contacted with a compound to optionally radiosensitize or radioprotect the cells or determine if the compound is a radiosensitizer or a radioprotector.

Accordingly another aspect includes a method of determining if a cancer cell is radiosensitive comprising treating a cell with a dose of radiation, optionally in combination with a radiosentizing agent for a sufficient time, isolating RNA, measuring a RNA integrity value, and comparing to a control, optionally untreated or treated with a dose of radiation alone or a radiosensitizing agent alone; wherein a decrease in RNA integrity is indicative that the cancer cell is radiosensitive and a stable or comparable to control RNA integrity is indicative that the cancer cell is radioresistant.

The cancer cell can optionally be in vitro and/or in vivo.

In an embodiment, the radiosensitizer is selected from oxygen increasing agents, hypoxic cell sensitizers, halogenated pyrimidines, and/or bioreductive agents.

Another aspect includes a method of determining if an agent is a radiosensitizing agent or a radioprotecting agent comprising:
a. incubating a cell source with a test agent;
b. exposing the cell source to a radiation dose;
c. assaying a sample of the cell source to obtain a RNA integrity value and optionally RNA concentration of a sample of the cell source incubated with the test agent;
d. comparing the RNA integrity value and optionally RNA concentration to a control reference sample e.g. corresponding to a sample incubated in the absence of the test agent and exposed to the radiation dose; and
e. identifying the test agent as a radiosensitizing agent if the RNA integrity value indicates that that RNA integrity and optionally the RNA concentration is decreased compared to the control reference sample value and identifying the agent as a radioprotecting agent if the RNA integrity value indicates that that RNA integrity and optionally the RNA concentration is increased compared to the control reference sample.

In an embodiment, the method comprises determining a radiation response score derived from the increase, decrease or absence of change in the RNA integrity value and optionally the RNA concentration compared to the control. The radiation response score can for example be used to rank or group the radioprotecting or radiosensitizing effectiveness of various test agents.

In an embodiment the cell source is incubated with (or a non-human animal is administered) the test agent for at least 24 h, at least 36 h, at least 48 h, at least 60 h or at least 72 h before measuring the RNA integrity and/or RNA concentration of the sample.

The test agent can also in an embodiment be administered to a subject having or suspected of having a cancer. For example, the test agent can be a radiosensitizing agent such as a taxane that is administered to the subject prior to radiation to determine tumour sensitivity to radiation.

In an embodiment, the cell used with the test agent is a cancer cell.

In another embodiment, the cancer cells are exposed to the radiation dose in vitro or in vivo. For example, cancer cells exposed in vivo includes where the subject is exposed to the radiation dose and/or receives the radiation comprising treatment regimen.

In an embodiment the control is a response threshold or one or more response thresholds.

In another embodiment, the response threshold is derived from an untreated sample and/or is a standard derived from a plurality of untreated samples.

In yet another embodiment, the response threshold is derived from an unresponsive sample and/or a responsive sample and/or is a standard derived from a plurality of unresponsive samples and/or responsive samples.

A further aspect includes a method for evaluating a patient-derived cancer cell sample optionally selected from a breast cancer cell sample or an ovarian cancer cell sample, the method comprising:
  a. assaying the cancer cell sample obtained from a subject after the subject has been exposed to a radiation dose with or without pre-treatment or concurrent treatment with a chemotherapy agent to obtain a RNA integrity value and optionally a RNA concentration of the cancer cell sample;
  b. identifying an increase, or decrease or absence of change in the RNA integrity value and optionally an increase, decrease or absence of change in the RNA concentration compared to a control; and
  c. optionally determining a response score derived from the increase or decrease or absence of change in the RNA integrity value and optionally the increase or decrease in the RNA concentration.

In an embodiment, the method for evaluating a patient-derived cancer cell sample optionally selected from a breast cancer cell sample or an ovarian cancer cell sample, the method comprising:
  a. obtaining a cancer cell sample, optionally a breast cancer cell sample or an ovarian cancer cell sample from a subject after the subject has been exposed to a radiation dose with or without pre-treatment or concurrent treatment with a cytotoxic, optionally chemotherapy agent; and
  b. assaying the cancer cell sample to obtain a RNA integrity value and optionally a RNA concentration of the cancer cell sample.

In an embodiment, the method further comprises comparing the RNA integrity value and/or the RNA concentration of the patient cancer cell sample to a control such as a response threshold wherein a decreased RNA integrity indicated by the RNA integrity value and/or a decreased RNA concentration of the patient cancer cell sample compared to the response threshold is predictive that the patient is responsive to the radiation therapy and a comparable (e.g. absence of change) or an increased RNA integrity indicated by the RNA integrity value and/or increased RNA concentration of the patient cancer cell sample compared to the response threshold is predictive/indicative the patient is unresponsive to the radiation treatment.

Another aspect includes a method of identifying non-responding patients comprising:
  a. obtaining a cancer cell sample from the patient after the patient has been exposed to one or more radiation doses;
  b. assaying the cancer cell sample to obtain a RNA integrity value and/or a RNA concentration of the cancer cell sample;
  c. comparing to a response threshold; and
  d. identifying patients having a RNA integrity indicated by a RNA integrity value and/or a RNA concentration that is above the response threshold.

Yet a further aspect include, a method of predicting a treatment outcome of a patient having cancer optionally breast cancer or ovarian cancer, the method comprising: assaying a cancer cell sample obtained from the subject to obtain a RNA integrity value and/or RNA concentration , wherein the subject has been treated with a radiation dose, wherein a RNA integrity indicated by the RNA integrity value that is below a response threshold predicts subject/cancer response to the radiation treatment and a decreased risk of progression; and a RNA integrity indicated by the RNA integrity value and/or RNA concentration that is higher than the response threshold predicts subject/cancer resistance to the radiation treatment and an increased risk of disease progression.

Obtaining a RNA integrity value and/or RNA concentration or obtaining a RNA integrity value and optionally RNA concentration means that a RNA integrity value is obtained alone or in combination with a RNA concentration.

In an embodiment, if the subject/cancer is predicted to have an increased risk of progression, the method further comprises changing the treatment and if the subject/cancer is predicted to have a decreased risk of progression, continuing the treatment.

In an embodiment, the radiation dose and/or chemotherapy is administered preoperatively.

A further aspect includes a treatment method comprising:
  a) exposing a patient with cancer to a radiation dose;
  b) obtaining a cancer cell sample from the patient after administration of the radiation dose;
  c) assaying the cancer cell sample to obtain a RNA integrity value and optionally a RNA concentration of the cancer cell sample and
  d) continuing the treatment when the RNA integrity indicated by the RNA integrity value and optionally the RNA concentration is decreased compared to a control such as a response threshold and changing the treatment when the RNA integrity indicated by the RNA integrity value and optionally the RNA concentration is comparable (e.g. absence of change) or increased compared to the control, optionally response threshold.

Also is provided in another aspect is use a method described herein for treating a subject with cancer, the use comprising a) assaying a cancer cell sample to obtain a RNA integrity value and optionally a RNA concentration of the cancer cell sample, wherein the patient has been exposed to a radiation dose and b) continuing to treat the patient when the RNA integrity indicated by the RNA integrity value and optionally the RNA concentration is decreased compared to a control such as a response threshold and changing the treatment when the RNA integrity indicated by the RNA integrity value and optionally the RNA concentration is comparable (e.g. absence of change) or increased compared to the control, optionally response threshold.

In an embodiment, step b comprises assigning the patient to continue the treatment when the RNA integrity indicated by the RNA integrity value and optionally the RNA concentration is decreased compared to a control such as a response threshold and assigning the patient to change the treatment when the RNA integrity indicated by the RNA integrity value and optionally the RNA concentration is comparable (e.g. absence of change) or increased compared to the control, optionally response threshold.

In an embodiment, the cancer cell sample is a breast cancer cell sample obtained from a breast cancer patient.

In another embodiment, the breast cancer is of the Her2, basal, luminal A, luminal B, or "normal" subtypes.

In another embodiment, the breast cancer patient has advanced disease, including locally advanced or inflammatory breast cancer (LABC).

In another embodiment, the cancer cell sample is an ovarian cancer cell sample obtained from an ovarian cancer patient.

In yet another embodiment, the response threshold is derived from an untreated cancer, optionally breast cancer or ovarian cancer patient or a standard derived from a plurality of untreated cancer, optionally breast cancer or ovarian cancer, patients.

In another embodiment, the response threshold derived untreated cancer patient or the standard derived from a plurality of untreated cancer patients is derived from one or more pretreatment samples.

In an embodiment, the response threshold predictive of responsiveness is RNA integrity and/or concentration decreased by at least 10%, at least 20%, at least 30%, at least 40%, at least 50%, at least 60%, at least 70%, at least 80% or at least 90% below a untreated control such as a pretreatment value.

In yet another embodiment, the response threshold is derived from an unresponsive patient cancer cell sample and/or a responsive patient cancer cell sample and/or is a standard derived from a plurality of unresponsive patient cancer cell samples and/or a plurality of responsive patient cancer cell samples.

In an embodiment, the patient is further treated with a dose of a chemotherapeutic agent.

In a further embodiment, the chemotherapeutic agent is selected from taxane chemotherapeutics for example paclitaxel, docetaxel, larotaxel, Abraxane, docoxahexaenoic acid-linked paclitaxel, paclitaxel polyglumex, Ortataxel, Genexol, liposomal-encapsulated paclitaxel, and paclitaxel in a Vitamin E emulsion In an embodiment, the taxane is docetaxel or paclitaxel.

In another embodiment, the cancer cell sample is obtained after the patient has received 1, 2, 3, 4, 5, 6, or more doses of radiation treatment.

In another embodiment, two or more cancer cell samples are obtained.

In another embodiment, the RNA integrity is measured by electrophoretic separation of RNA, optionally total RNA or ribosomal RNA.

In yet another embodiment, measuring the RNA integrity value comprises calculating a 28S: 18S ribosomal (rRNA) ratio.

In an embodiment, the RNA integrity is measured by calculating a RIN e.g., the RNA integrity value is the RNA integrity number (RIN) and is assayed for example using an Agilent bioanalyzer machine. The RIN is calculated using an algorithm described in, Schroeder, A., O. Mueller, et al. 2006; Mueller 2004; Vespucci 2005, e.g. Agilent Expert, which is used in the Agilent 2100 Bioanalyzer. The method automatically selects features from signal measurements and constructs regression models based on a Bayesian learning technique. Feature spaces of different dimensionality are compared in the Bayesian framework, which allows selecting a final feature combination corresponding to models with high posterior probability. The approach was applied to a large collection of electrophoretic RNA measurements recorded with an Agilent 2100 bioanalyzer to develop an algorithm that describes RNA integrity. The resulting algorithm is a user-independent, automated and reliable procedure for standardization of RNA quality control that allows the calculation of an RNA integrity number (RIN) under certain conditions and/or for certain samples.

In yet another embodiment, the RNA integrity is measured using an RNA disruption assay as described in WO2013/159200, incorporated herein in its entirety. The RNA integrity value is in an embodiment, a RNA disruption index (RDI) value. In another embodiment, wherein the sample is a patient sample, the RNA integrity value comprises a RDA zone.

In a further embodiment, RNA is isolated from the cancer cell sample and the RNA integrity value and/or the RNA concentration is measured on the isolated RNA.

In another embodiment, the RNA integrity value is measured by separating the RNA by microcapillary electrophoresis, and detecting RNA integrity with fluorescent dyes.

In another embodiment, the RNA concentration is measured.

In an embodiment, the RNA integrity value is measured.

In another embodiment, the RNA integrity value is RNA integrity number (RIN). In another embodiment, the RNA integrity value is a RNA disruption assay value e.g. a RDI or a RDA zone. RDI can be more sensitive than RIN in measuring radiation induced effects. RDI more accurately captures cytotoxic e.g. radiation and/or chemotherapy induced RNA degradation.

In another embodiment, both the RNA concentration and the RNA integrity are measured.

In yet another aspect is provided a method for remotely interpreting RNA integrity of a cancer cell sample, the method comprising:
  a. obtaining a cancer cell sample optionally selected from breast canner and ovarian cancer from a patient that has received a radiation dose at a remote site;
  b. assaying the cancer cell sample to obtain one or more datasets selected from an electropherogram dataset, a RNA integrity value and optionally a RNA concentration at the remote site;
  c. transmitting one or more datasets to a central site, by internet;
  d. generating, at the central site, one or more interpretive data sets from the one or more datasets using a computer;
  e. i. generating, using a computer, one or more test reports under the control of one or more expert reviewers; and,
  f. transmitting the one or more test reports to the remote site or another site by Internet.

In yet another aspect is provided a method for remotely interpreting RNA integrity of a cancer cell sample, the method comprising:
  a. obtaining a cancer cell sample optionally selected from breast cancer and ovarian cancer from a patient that has received a radiation dose at a remote site;
  b. sending the cancer cell sample to the central site:
  c. assaying the received cancer cell sample to obtain one or more datasets selected from an electropherogram dataset, a RNA integrity value and optionally a RNA concentration at the central site;

d. generating, at the central site, one or more interpretive data sets from the one or more datasets using a computer;
e. generating, using a computer, one or more test reports under the control of one or more expert reviewers; and,
f. transmitting the one or more test reports to the remote site or another site by internet.

The one or more datasets including the electropherogram dataset and the one or more interpretive datasets may be obtained and sent, for example, via a data communication network or wireless communication.

In an embodiment, the cancer cell sample, for example obtained from the subject, is placed in an RNA isolating or stabilizing composition prior to assaying.

A further aspect includes a kit for use in a method described herein comprising a RNA isolating composition and an RNAse free vessel for receiving the cancer cell sample and/or RNA sample, wherein the vessel is optionally labeled with an identifier optionally permitting for anonymous testing.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 4: Graph of RIN values vs. RNA concentration for patients in the London clinical trial who achieved pCR (Responders) and patients who did not achieve pCR (Non-Responders).

DETAILED DESCRIPTION OF THE DISCLOSURE

I. Definitions

Figure 1:
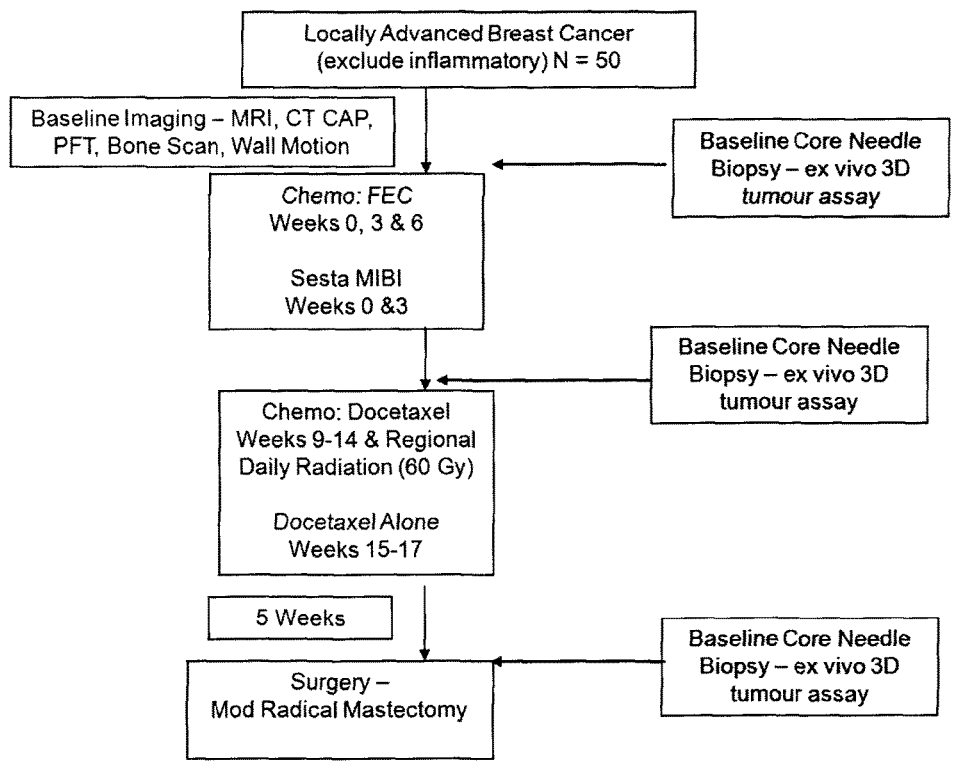
FIG. 1: Schema of clinical trial conducted at the London Regional Health Sciences Centre, whereby patients with locally advanced breast cancer were treated firstly by a chemotherapy regimen including 5'Fuorouracil, epirubicin, and cyclophosphamide (FEC) followed, by weekly docetaxel with concurrent daily radiation, followed by weekly docetaxel.

The term "amount" as used herein with respect to RNA degradation refers to an amount (e.g. relative amount or absolute amount) of RNA degradation that is detectable or measurable in RNA isolated from a sample. For example, the amount can be expressed using an absolute value (e.g. an RDI value or a RIN value) or a relative amount such as 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, 5.0, 10, 15, 20, 25, 30, 40, 60, 80 and/or 100 times a control amount, where for example, the control amount is, for example, a pre-treatment amount or, for example, a reference value corresponding to the average or median level in untreated or pretreatment samples. The amount can be compared to one or more threshold values, for example which identifies subjects with a likelihood of responding to the treatment.

The term "baseline amount" as used herein refers to an amount of RNA degradation (e.g. how intact the RNA is) in a sample such as a pretreatment sample that can be used for comparison to a test sample (e.g. comparison to a cell population and/or tumour) taken at a later time point, for example during or after treatment e.g. during or after a treatment regimen comprising radiation and optionally chemotherapy, cytotoxic antibody and/or other treatment. For example, in methods related to monitoring response to treatment, "base-line amount" can refer to a level of RNA degradation in a sample taken prior to a subsequent sample, e.g. a base-line sample is taken before treatment, the comparison to which provides an indication of response to treatment.

The term "assaying a cancer cell sample to obtain a RNA integrity value" as used herein means performing an assay on a RNA sample of the cancer cell sample for ascertaining or measuring quantitatively or semi-quantitatively the degree of degradation and/or intactness of RNA or a fraction thereof to provide a value representative of the assay results. For example, the RNA integrity value can be determined by a number of methods involving microcapillary electrophoresis, for example by determining a RNA integrity number using for example an Agilent Bioanalyzer machine, an Experion® Capillary Electrophoresis System with its equivalent RNA Quality Index (RQI), Nanodrop® (Thermo Scientific, Inc.) or other equivalent systems, such as those manufactured by Applied Biosystems, Lumex, or Beckman Coulter Corporation or similar system, and/or for example In where the RNA integrity value is a 28S:18s rRNA ratio, determined using gel agarose electrophoresis and/or spectroscopy, for example by assessing UV absorbance at 280:260. Other methods of determining RNA integrity including methods disclosed in Patent Cooperation Treaty Application No PCT/CA2013/000408 entitled ASSAYS, METHODS AND APPARATUS FOR ASSESSING RNA DISRUPTION filed Apr. 24, 2013, incorporated by reference herein in its entirety, describes assays for assessing RNA integrity, which can be used herein. In embodiments, an electropherogram dataset is obtained (e.g. features of which comprise the RNA profile) and used to calculate an RNA integrity value.

The term "assaying a cancer cell sample to obtain a RNA concentration" as used herein means performing an assay on a RNA sample for ascertaining or measuring quantitatively the amount of RNA or a fraction thereof to provide a value representative of the assay results. For example, the RNA concentration can be determined by a number of methods including for example microcapillary electrophoresis, for example using for example an Agilent Bioanalyzer machine, an Experion® Capillary Electrophoresis System with its equivalent RNA Quality Index (RQI), Nanodrop® (Thermo Scientific, Inc.) or other equivalent systems, such as those manufactured by Applied Biosystems, Lumex, or Beckman Coulter Corporation or similar system. The RNA concentration can be based on UV absorbance, for example by assessing UV absorbance at 260 nm.

The term "breast cancer" as used herein includes all subtypes of breast cancer, including the HER2, basal, lumina (A, luminal B, and "normal" subtypes of breast cancer as well as locally advanced breast cancer (LABC).

The term "cancer cell sample" as used herein means for example any sample comprising cancer cells and/or cancer bed cells including for example cells obtained from a cancer cell source such as tumour tissue or an in vitro cell culture. The cancer cells can for example be breast cancer cells, ovarian cancer cells, non-melanoma skin cancer, head and neck cancer, breast cancer, lung cancer cells such as non-small cell lung cancer, cervical cancer, anal cancer, prostate cancer, lymphoma cancer cells, liposarcoma cancer cells, or any cancer cells treatable by a regimen comprising radiation or being tested for treatability by a regimen comprising radiation.

The term "cancer bed cells" as used herein means reparative tissue cells that have infiltrated a site previously occupied by a cancer (e.g. at the tumour lesion site) and can include stromal connective tissues surrounding the tumour. These may be obtained in a patient who has responded to the radiation treatment, optionally post treatment or during treatment in a patient that has responded rapidly. For example in the MA22 study, some tumours that exhibited a pCR post-treatment had strong RNA degradation in samples obtained at the tumour lesion site, even though no tumour cells were present, and in the MA22 study some samples that went on to have a pCR had no tumour cellularity mid-therapy but had a high RDI value (low RIN) which indicates that the cells providing the RNA at this timepoint were likely reparative tissue cells. These cancer bed cells are more metabolically active than the non-tumour cells which surround the site.

The term "changing cancer treatment" as used herein includes for example one or more of changing the dosage level and/or schedule of the radiation or chemotherapeutic, discontinuing the treatment, adding a chemotherapeutic agent(s), biologic(s) or radiosensitizing agent(s) to the treatment or changing to an alternate cancer treatment such as a drug therapy or surgery (e.g. discontinuing radiation treatment).

The term "comparable to a control" or "comparable to a reference threshold" or "absence of a change" as used herein in the context of a RNA integrity value or RNA concentration means less than a 30% decrease or increase, optionally, this decrease could be less than a 25% decrease, less than a 20% decrease, or less than a 10% decrease from a control such as a pretreatment control, for example, or the increase could be less than a 25% increase, less than a 20% increase, or less than a 10% increase from a control such as a pretreatment control. In an in vitro method, "comparable to a control" "comparable to a reference threshold" or "absence of a change" can be less than a 10% or 5% decrease or increase. In an in vivo method, "comparable to control", "comparable to a reference threshold" or "absence of a change" can be less than a 30% or 25% increase or decrease.

The term "control" as used herein refers to a comparator sample such as intact RNA and/or RNA obtained from a subject or a group of individuals who are known as non-responders and/or responders and/or a reference sample such as a pretreatment sample or earlier sample from the tested individual. For example, the control can be a sample from a subject comprising cancer cell RNA such as breast cancer or ovarian cancer cell RNA, such as a pretreatment or earlier sample from the subject. The control can also be the expected or predetermined RNA integrity value for an untreated cancer tissue or cancer cell RNA sample (e.g. intact RNA). For example, an untreated cancer tissue or untreated cancer cell RNA sample can be determined and is expected to be "intact", for example have a RIN value of greater than 7, or greater than 8, or greater than 9, (a RIN of 9 can be used particularly for in vitro cultures). The control can be used as a reference threshold for example when monitoring the response of a patient or in cell line based testing. The baseline or pretreatment levels seen in cells in in vitro cultures is a much lower level of RNA degradation than in vivo, where tumours can have significantly higher baseline levels of RNA degradation. Cell cultures in the laboratory are under ideal conditions to promote cell viability, including growth factors, nutrients, buffers, appropriate oxygenation, ROS scavengers, vitamins, etc. In an embodiment, the control is a positive control e.g. cells/tumour treated with radiation. In another embodiment, the control is a negative control, e.g. cell/tumour not receiving radiation treatment, optionally not receiving any treatment.

The term "cytotoxic treatment" as used herein means any agent that can be used with radiation, sequentially and/or concurrently, that can induce cell death that is used in the treatment of cancer, including for example, traditional and non-traditional chemotherapy (e.g. targeted therapies), radiation treatment, hormonal treatment (e.g. for responsive cancers) and combinations thereof. Such agents include but are not limited to microtubule stabilizing agents such as Docetaxel and paclitaxel, DNA synthesis inhibitors such Epirubicin, inhibitors of Her2 Receptor such as Trastuzumab, DNA cross-linking agents such as Mafosfamide, carboplatin and cisplatin, VEGFA inhibitors such as Bevacizumab, Receptor Tyrosine Kinase inhibitors such as Sunitinib and Toceranib, Bisphosphonates such as Zoledronic acid, Thymidylate synthase inhibitors such as 5-fluorouracil.

The term "chemotherapeutic agent" as used herein means any drug or drug combination used for the treatment of cancer such as breast cancer or ovarian cancer or other cancers treatable by radiation comprising regimens such as for example non-melanoma skin cancer, head and neck cancer, breast cancer, non-small cell lung cancer, cervical cancer, anal cancer, prostate cancer, including for example drugs used for primary chemotherapy including for example a platinating agent (e.g. cisplatin and/or carboplatin) and/or a taxane (e.g. paclitaxel and/or docetaxel), drugs typically used in the treatment of recurrent ovarian cancer (e.g. anthracyclines such as doxorubicin or epirubicin or their pegylated forms), topoisomerase I and II inhibitors (e.g. topotecan and etoposide, respectively), nucleoside analogs such as gemcitabine and 5-fluorouracil, DNA cross-linking agents such as Mafosfamide, the estrogen receptor blocker tamoxifen, and/or the Her-2/Neu blocker bevacizumab. In an embodiment, the chemotherapeutic agent is sunitinib.

The term "dose" as used herein in reference to radiation refers to an individual radiation exposure either administered at each time within a schedule or the total amount of radiation exposure within a schedule. With respect to a chemotherapy treatment a dose means an amount of an individual drug either administered at each time within a schedule OR the total amount of each drug administered within a schedule or the total amount of drug administered during a course of chemotherapy.

The term "decreased RNA integrity" as used herein for determining response with respect to patient samples means an RNA integrity that is at least 20%, at least 25%, at least 30%, at least 40%, at least 50%, at least 60%, at least 70%, at least 80% or at least 90% less than a control or corresponding value for example a pretreatment sample or for example a maximal value (e.g. maximal RIN). With respect to a cell culture sample, a decrease of at least 5%, 10%, 15%, 20% or 25% compared to control is indicative of a decreased RNA integrity.

The term "decreased RNA concentration" as used herein means an RNA integrity that is at least 20%, at least 25%, at least 30%, at least 40%, at least 50%, at least 60%, at least 70%, at least 80% or at least 90% less than a control or corresponding reference value for example a pretreatment sample or for example a maximal value.

The term "positive treatment outcome" in the context of a patient as used herein refers to a positive therapeutic response to treatment, for example alleviation or amelioration of one or more symptoms or conditions, diminishment of extent of disease, stabilized (i.e. not worsening) state of disease, preventing spread of disease or preventing disease progression, delay or slowing of disease progression, reversal of disease, amelioration or palliation of the disease state, and remission (whether partial or total), whether detectable or undetectable. "A positive treatment outcome" can also mean prolonging overall survival, stable disease and/or disease/progression free survival as compared to expected survival if not receiving treatment, including for example a pathologic complete response post-treatment. The extent of the positive treatment outcome can be for example related to the extent of RNA degradation and/or RNA concentration decrease determined for a cancer sample obtained during treatment.

The term "post-treatment" as used herein means after completion of a treatment comprising a radiation regimen, optionally completion of all arms of a treatment regimen e.g. after completion of any chemotherapy or other treatment post radiation.

The term "negative treatment outcome" in the context of a patient as used herein means a lack of a therapeutic response to the treatment, for example no response, recurrence of disease, or spread of disease (disease progression).

The term "responders" as used here means patients that demonstrate a positive treatment or therapeutic outcome, including for example, a measurable therapeutic response. Responders optionally include patients who demonstrate increased disease free survival (DFS) or overall survival (OS) compared to the average for a group of similarly treated patients, a pathological complete response (pCR) or a partial response.

The term "non-responders" as used herein means patients (e.g. non-responders) that do not demonstrate a positive treatment outcome including for example no measurable therapeutic response, for example exhibit a negative therapeutic outcome such as a decreased DSF or OS compared to the average for a group of similarly treated patients.

The term "RNA sample" means any sample comprising purified and/or isolated RNA, including any purified and/or isolated RNA fraction such as total RNA, rRNA, and/or mRNA. In an embodiment, the RNA sample comprises rRNA. An RNA sample can be obtained for example using for example a number of methods known in the art for isolating RNA.

The term "ovarian cancer" as used herein means all subtypes of ovarian cancer, including the serous, clear cell, endometrioid, and mucinous subtypes [10].

The term "radiation" in relation to a treatment means any energy, photon or particle, applied to a tumour, including for example ionizing radiation.

The term "radiosensitizer" as used herein means an agent such as a small molecule drug or biologic that makes a tumour cell more sensitive to radiation therapy. The radiosensitiver can be an oxygen increasing agent, a hypoxic cell sensitizer, a halogenated pyrimidine, or a bioreductive agent.

The term "oxygen increasing agent" as used herein means an agent such as a small molecule drug or biologic that increases tumour oxygenation and/or reduces tumour hypoxia, including for example oxygen. The term "hypoxic cell sensitizer" as used herein means an agent, such as a small molecule drug, that can mimic oxygen (but does not increase oxygen levels) and that is typically not metabolized by tumour cells allowing the agent to penetrate a tumour. Examples include nitroimidazoles. Hypoxic cell sensitizers, such as 2-nitroimiazole increase the killing of hypoxic cells, which are typically radioresistant.

The term "bioreductive agent" as used herein means an agent such as a small molecule drug that can be reduced to a cytotoxic species, for example in a hypoxic region of a tumour. Examples include quinone antiobiotics such as mitomycin C, niroaromatics, and di-N oxides.

The term "radioprotector" as used herein means s used herein means an agent such as a small molecule drug or biologic that makes a tumour cell less sensitive to radiation therapy.

The term "RNA degradation" as used herein means a decrease in the RNA integrity of isolated cancer cell or tissue RNA compared to RNA from untreated cancer cells or tissues, or an expected RNA integrity for cancer cells. For example, human RNA (e.g. isolated from primary cells and/or tissue) is commonly recognized as degraded when RIN is <7, and/or optionally <7, less than 6.8, less than 6.6, less than 6.4, less than 6.2, less than, 6.0, less than 5.8, less than 5.6, less than 5.4, less than 5.2 or less than 5.0 and for cell lines when RIN is for example =<8, optionally <9. The RNA degradation can comprise treatment induced RNA degradation and autolytic RNA degradation.

The term "autolytic RNA degradation" as used herein refers to RNA degradation taking place during autolytic cell destruction. Autolysis is initiated, for example, by the cells' lysosomes releasing digestive enzymes into the cytoplasm due to the cessation of active processes in the cell, and not due to an active physiologic or pathophysiologic process. Autolytic RNA degradation in a sample can be induced by removal of cells from physiologic environment for extended period of time (e.g. incubation in saline) and/or nonspecific cessation of physiologic processes e.g. heat treatment.

The term "treatment induced RNA degradation" as used herein refers to discretely fragmented and/or degraded RNA that is signal induced in response to a cytotoxic treatment such as radiation treatment, chemotherapy treatment and/or cytotoxic antibody treatment (e.g. Trastuzumab). Cytotoxic signal induced RNA degradation can include RNA degradation that has some features that resemble autolytic degradation, particularly for example during later stages.

The term "RNA integrity" as used herein means to the degree of intactness of the RNA following extraction or isolation from the cell or tissue sample e.g. whether the isolated RNA is degraded. RNA integrity can be assigned a value (e.g. RNA integrity value) that corresponds to the degree of RNA intactness and/or degradation, e.g. proportionately or inverse proportionately. A high RNA integrity is commonly taken as meaning little or no degradation, for example less than a 30% decrease, less than 25% decrease, less than 20% decrease from maximal RNA integrity value (e.g. when the RNA integrity value is measured using RIN, e.g. RIN=10 or other scale where RNA integrity value is proportional to the RNA integrity of the sample), or less than a 30% increase, less than a 20% increase for example from baseline when the RNA integrity value is inverse proportional to the RNA integrity of the sample e.g. RDI (e.g. for an in vivo sample and optionally less than 10% or 5% decrease or increase for an in vitro sample) and/or a RNA integrity value corresponding to a control such as a pretreatment control and retention of capacity to amplify mRNAs of interest following extraction or isolation. Using RDI, a high RNA integrity is for example less than 10, or less 3 and using RIN a high RNA integrity is greater than 7, greater than 8 or greater than 9. A low RNA integrity is for example RNA that exhibits greater than 20%, greater than 25%, greater than 30%, greater than 35%, greater than 40%, greater than 45%, greater than 50%, greater than 55%, greater than 60%, greater than 65%, greater than 70%, or greater than 75% decrease from maximal for example using RIN, wherein maximal RIN=10 (or other scale where the RNA integrity value is proportional to RNA integrity), or exhibits greater than 20%, greater than 25%, greater than 30%, greater than 35%, greater than 40%, greater than 45%, greater than 50%, greater than 55%, greater than 60%, greater than 65%, greater than 70%, or greater than 75% increase in RNA integrity value for example from baseline, for example using RDI (or other scale where the RNA integrity value is inverse-proportional to RNA integrity), a control such as a pretreatment control or decreased capacity to amplify mRNAs of interest when they are known to be present in controls in RNA following extraction or isolation.

The term "RNA integrity value" as used herein is a measure of the degree or extent of intactness or degradation of RNA of a sample following extraction or isolation from the cell or tissue sample. For example the RNA integrity value can be a spectrophotometer intensity measurement, and/or a 28S:18S ribosomal RNA ratio. The RNA integrity value can be an RNA integrity number (RIN), determined using an Agilent Bioanalyzer, the output of the RIN algorithm, wherein generally the higher the RIN value, the higher the RNA integrity and the lower the RIN value the higher the RNA degradation. For example, a RIN of 0 represents completely hydrolyzed RNA and a RIN of 10 represents completely undegraded RNA. A person skilled in the art would recognize that the scale could also be inverted (for example, by dividing the value into 1, e.g. 1/RNA integrity value) such that the lower the RNA integrity value, the higher the RNA integrity and the higher the RNA integrity value, the lower the RNA integrity. For example, the RNA integrity value can be the output of a calculation based on electropherogram features as described in Patent Cooperation Treaty Application No PCT/CA2013/000408, ASSAYS, METHODS AND APPARATUS FOR ASSESSING RNA DISRUPTION filed Apr. 24, 2013, for example represented as an RNA Disruption Index (RDI), or can be a transformed scale. For example for patient samples, the scale can be defined by clinical RNA disruption assay (RDA) zones based on cut-offs or response thresholds, wherein each score or RDA zone is associated with a likelihood of a response for example associated with a likelihood of responsive to a treatment, for example defined by NPV and/or PPV. In embodiments wherein RDI or RDA zones are employed, a high or increased RNA integrity value (for example compared to a baseline sample or control) is indicative of high or increased RNA degradation. For example in such an embodiment, the higher the RNA integrity value, the greater the induced RNA degradation (and decrease in RNA integrity). Any scale can be employed, for example 3, 10, or 600. Accordingly, wherein the RNA integrity value is proportional to the RNA integrity of the sample, a high or increased RNA integrity value corresponds to a high or increased RNA integrity and wherein the RNA integrity value is inverse proportional to the RNA integrity of the sample, a high or increased RNA integrity value corresponds to low or decreased RNA integrity. The RNA integrity value can be calculated using one or a number of features. Also the scale employed can be a linear scale or a logarithmic scale.

The term "RNA isolating or stabilizing composition" as used herein refers to any composition that inhibits RNAse activity and/or stabilizes RNA preventing RNA degradation.

The term "stable RNA integrity" as used herein means RNA that is not degraded appreciably, for example as compared to an appropriate comparator sample or the expected RNA integrity for the cell type of tissue. Typically for humans this is isolated RNA with RIN=>7, and can be for example in the context of tumour cell RNA=>6.8, =>6.6, =>6.4, =>6.2, =>6.0, or =>5.8 and for cell lines, for example RIN=>9. Other measures including RDI can also be used.

The terms "patient" and "subject" which are used herein interchangeably refer to any member of the animal kingdom, including mammals, for example dogs, rodents such as rats and mice, preferably a human being, including for example a subject that has or is suspected of having cancer, optionally breast cancer or ovarian cancer.

The term "RNA" as used herein includes any RNA or RNA fraction, including but not limited to total RNA, rRNA and/or mRNA, of subset of RNAs for example RNA can include the total of RNA types and components that may be present following RNA isolation, for example ribosomal RNAs (rRNAs) messenger RNAs (mRNAs), or fractions comprising for example at least rRNA. As an example, total RNA can be used with the methods described herein or a class or subset of RNAs can also be used. For example, RNA subsets that can be assayed with the methods described include for example subsets comprising rRNA, and/or mRNA.

The term "resistant" as used herein refers to a cancer cell or tumour response to radiation alone or in combination with a cytotoxic, optionally chemotherapeutic, agent or regimen, where the cancer cells or subset of cancer cells within a tumour show no or insufficient response (for example determinable in a clinical study) to the treatment in terms of RNA degradation, which is associated for example with a negative treatment outcome.

The term "response" as used herein refers to a cancer cell or tumor response to radiation alone or in combination with a cytotoxic, optionally chemotherapeutic, agent and/or regimen, where the cancer cells or subset of cancer cells within a tumour respond to the treatment in terms of RNA degradation—e.g. show significant and/or sufficient RNA degradation (for example determinable in a clinical study), which is associated for example with a positive treatment outcome.

The term "low risk" as used in relation to progression refers to less than average risk (e.g. decreased probability) calculated for a group of patients with the same cancer, treated similarly; and high risk of progression means greater than average risk (e.g. increased probability) compared to the group of patients.

The term "RNA Disruption Index" or "RDI" is used herein as used in Patent Cooperation Treaty Application No PCT/CA2013/000408 filed Apr. 24, 2013 and is a value generated using RNA disruption assay (RDA) and can be a ratio of defined features (e.g. features shown in FIG. 12), of the output of linear discriminant analysis (LDA) or quadratic discriminant analysis of features described herein. The RDI is a logarithmic scale and can be calculated using features shown for example in FIG. 12, optionally for example based on (Intermediate Area+LowC Area)/(28S Area+18S Area). The RDI scale reflects the absolute ratio of disrupted RNA/normal RNA. The RDI values determined from a group of known response outcome patients (e.g. that are determined to be associated with a particular NPV or PPV) can be used to define the thresholds boundary for RDA zones.

The term "RDA zones" as used herein refers to clinical zones associated with treatment response outcome comprising a range of RDI values. Each RDA zone is defined by one or two boundaries each boundary corresponding to a selected threshold (e.g. corresponding to a desired NPV or PPV). Subject RDI values that fall within the clinical zones that are associated with or are predictive of treatment response, for example pCR and/or increased DFS. In an embodiment, 3 RNA disruption assay zones can be used, RDA zone 1, RDA zone 2 and RDA zone 3, defined by selected NPV and/or PPVs. A person skilled in the art would readily realize that any number of zones can be used each with different selected thresholds.

The term "RDA zone 1" as used herein refers to a range of RDA scores (e.g. RDI values) that have a negative predictive value (NPV) of at least 0.8, at least 0.85, at least 0.9, at least 0.95, at least 0.96, at least 0.97, at least 0.98 or greater. These numbers and the associated thresholds, are for example based on DFS and/or pCR clinical trial results for a specific treatment for example such as a clinical trial such as a clinical trial described in Example 1 with increased number of patients. In an example embodiment, RDA Zone 1 is equal to an RDI of equal or less than 10 calculated using the feature Intermediate Area/(28S+18S Areas). In other embodiments, other features or combination of features can be used. The "RDA zone 1" can be defined to include any set of scores by selecting the desired NPV.

The term "RDA zone 2" as used herein refers to a range of RDA scores (e.g. RDI values) falling between RDA zone 1 and 3, and can be considered an intermediate or indeterminate zone.

The term "RDA zone 3" as used herein refers to a range of RDA scores (e.g. RDI values) that have a positive predictive value (PPV) of at least 0.15, at least 0.16, at least 0.17, at least 0.18, at least 0.19, at least 0.2 or greater. These numbers and the associated thresholds are for example based on pCR and/or DFS clinical trial results for a given treatment, e.g. a clinical trial as described in Example 1 with additional patients. The "RDA zone 3" can be defined to include any set of scores by selecting the desired PPV.

In an embodiment, the radiation response score is an RDA zone 1, 2 or 3. The radiation response score can also be resistant, responding and indeterminate.

The term "response threshold" or "reference threshold" as used herein can be an expression or cut-off value of RNA integrity and/or RNA concentration in a pre-determined sample or group of samples, above and/or below which a cancer cell type or tumour is identified as being more likely resistant or more likely responsive to treatment and for example indicative of patient outcome. For example, a patient that has a RNA integrity value indicative of RNA integrity and/or RNA concentration below a cut-off or response threshold is indicated to be more likely responsive to the radiation treatment and/or regimen and/or predicts positive treatment outcome. The response threshold can for example be derived from a control such as a pretreatment or untreated sample or a value derived from a population of subjects that are known responders and/or non-responders which for a preselected degree of specificity and sensitivity, classifies patients likely to be responders from patients likely to be non-responders. In the case of a control such as a pretreatment control or untreated control, the response threshold can be the expected RNA integrity for (e.g. when a RIN value, optionally 7, 8, 9 or 10) based on for example the cell population, treatment etc. A person skilled in the art will recognize that the direction of the change indicative of worse or better outcome will depend on the scale used.

The term "sample" as used herein refers to 1) any biological fluid, cell or tissue sample from a subject (e.g. test subject) or cell line that comprises cellular RNA, optionally tumour tissue/cells and/or cancer bed cells and/or 2) RNA derived from such a sample. For example, the sample can be a biopsy, including a needle aspirate, such as a fine needle aspirate, a core biopsy, a brush biopsy and/or a laparoscopic biopsy. The sample can, for example, be a "post-treatment" sample wherein the sample is obtained after one or more doses of radiation or cytotoxic cancer treatments, or a "base-line sample" which is optionally pre-treatment or taken at an earlier time-point than the post-treatment sample, and is for example, used as a base line for assessing or monitoring response to a radiation optionally in combination with cytotoxic treatment.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, reversal of disease, amelioration or palliation of the disease state, and remission (whether partial or total), whether detectable or undetectable. "Treatment" can also mean prolonging survival as compared to expected survival if not receiving treatment.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The recitation of numerical ranges by endpoints herein includes all numbers and fractions subsumed within that range (e.g. 1 to 5 includes 1, 1.5, 2, 2.75, 3, 3.90, 4, and 5). It is al3o to be understood that all numbers and fractions thereof are presumed to be modified by the term "about." Further, it is to be understood that "a," "an," and "the" include plural referents unless the content clearly dictates otherwise.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Methods

Described herein are methods for evaluation of cancer cells including for example breast cancer cells and ovarian cancer cells for their response to radiation treatment.

A clinical study was described in PCT/CA2008/001561, herein incorporated by reference, which demonstrated that breast cancer cells demonstrate reduced RNA integrity when treated with a chemotherapeutic. It is has also been demonstrated by the inventors that ovarian cancer cell lines show loss of RNA content (e.g. concentration) and/or integrity in response to chemotherapeutic treatment.

Patent Cooperation Treaty Application No PCT/CA2013/000408 entitled ASSAYS, METHODS AND APPARATUS FOR ASSESSING RNA DISRUPTION filed Apr. 24, 2013, incorporated by reference herein in its entirety, describes assays for assessing RNA integrity, which can be used herein.

Accordingly, an aspect includes a method of evaluating a cancer cell sample optionally selected from a breast cancer cell sample and an ovarian cancer cell sample, the method comprising:

a) obtaining a cancer cell sample, optionally a breast cancer cell sample or an ovarian cancer cell sample, after the cancer cells have been exposed to a radiation dose;

b) assaying the cancer cell sample to obtain a RNA integrity value and/or a RNA concentration of the cancer cell sample.

A decreased RNA integrity value is reflective of RNA degradation and responsiveness to treatment.

In an embodiment, the method further comprises comparing the RNA integrity value and/or the RNA concentration of the cancer cell sample to a response threshold wherein a decreased RNA integrity value and/or RNA concentration of the cancer cell sample compared to the response threshold is predictive that the cancer cells are responsive to the radiation therapy and a comparable or an increased RNA integrity value (i.e. indicative of comparable or increased RNA integrity) and/or RNA concentration of the cancer cell sample compared to the response threshold is predictive the cancer cells are unresponsive to the radiation treatment.

It is demonstrated herein that RNA degradation can be detected in breast cancer cells and ovarian cancer cells in response to radiation exposure. In an embodiment, the cancer cell sample is a breast cancer cell sample. In another embodiment, the cancer cell sample is an ovarian cancer cell sample.

RNA degradation was detected for example after one dose in the ovarian cancer cell line. In an embodiment, the cancer cells have received 1, 2, 3, 4, 5, 6 or more doses of radiation treatment.

RNA degradation is detected in cancer cells such as breast cancer and ovarian cancer cells treated with radiation and a cytotoxic agent such as a chemotherapeutic. In an embodiment, the cells are further treated with a dose of a cancer cytoxic agent, optionally a chemotherapeutic agent. In an embodiment, the chemotherapeutic agent is selected from anthracyclines, taxanes and combinations thereof, preferably wherein the chemotherapeutic agent comprises epirubicin, docetaxel or combinations thereof. In another embodiment, the taxane is paclitaxel, docetaxel, larotaxel, Abraxane, docoxahexaenoic acid-linked paclitaxel, paclitaxel polyglumex, Ortataxel, Genexol, liposomal-encapsulated paclitaxel, and paclitaxel in a Vitamin E emulsion In a further embodiment, the taxane is docetaxel or paclitaxel.

In an embodiment, the patient is administered in a radiosensitizer agent. In an embodiment, the radiosensitizer agent is selected from a variety of classes of compounds, including oxygen, hypoxic cell sensitizers, halogenated pyrimidines, and bioreductive agents.

A decreased RNA integrity value is reflective of RNA degradation, primarily the degradation of the highly abundant rRNAs. In an embodiment, the RNA sample is total RNA. In another embodiment, the RNA sample is and/or comprises rRNA. In another embodiment, the RNA sample is and/or comprises mRNA.

The method can be used for example to test a tumour's sensitivity to a radiation sensitizing agent and/or screen for compounds that radio-sensitizes cancer cells or otherwise improve response to radiation treatment. For example, cells can be pretreated in vitro with a compound and subsequently exposed to radiation. The extent of RNA integrity and concentration changes can be used to screen compounds. Accordingly, in another embodiment, the cells are contacted with a compound to determine if the compound is a radio-sensitizer and/or a radio-protector. As demonstrated in the examples, combinations of chemotherapy and radiation can result in prominent increases in RNA degradation compared to chemotherapy treatment or radiation treatment alone. Accordingly in an embodiment, the method is for identifying synergistic combinations of a test agent and radiation.

In an embodiment, the method comprises: i) exposing cells to a fixed dose or radiation and an increasing dose of the test agent and ii) assessing the RNA integrity of the cells, wherein a test compound that reduces the RNA integrity compared to a control is radiation sensitizer and the RNA integrity is a radiation radioprotector.

One example of a screen would be to conduct the RNA integrity assay with fixed doses of radiation and to assess the ability of the radioprotector or the radiosensitizer to reduce or augment the degree of RNA degradation, respectively. The extent of RNA degradation at the various radiation doses in the absence or presence of the radiosensitizer or radioprotector can be used to determine LD50s in the absence or presence of the agent, in order to quantify the degree of protection/sensitization.

Extent of response can be assessed for example by comparing to a response threshold. For example, the response threshold for in vitro embodiments can comprise an untreated control or a value that corresponds to an in vitro control. For example, cell lines generally have little if any RNA degradation if handled appropriately using methods which are known in the art. The response threshold therefore can be a selected value for example, 9, 8 or 7. In an embodiment, the response threshold is derived from an untreated sample and/or is a standard derived from a plurality untreated samples.

The response threshold can also be a preselected threshold derived for example from treated or untreated samples, such as a median or average. In yet another embodiment, the response threshold is derived from an unresponsive sample and/or a responsive sample and/or is a standard derived from a plurality of unresponsive samples and/or responsive samples.

As mentioned above, cancer cells such as breast cancer and ovarian cancer cells can be screened in vitro. Tests can also be conducted in vivo using for example an animal model where cancer cells are implanted, the animal is administered radiation alone or in combination with a test agent and the response monitored. Accordingly, in another embodiment, the cancer cells are exposed to radiation in vitro or in vivo.

The cancer cell is in an embodiment in vivo in a patient.

In an embodiment, the patient is treated with radiation and/or chemotherapy prior to surgery. When administered after surgery, methods dexcribed herein can be used to monitor response to chemotherapy/radiation therapy for example in any recurrent tumours.

In vivo cells may experience increased signal induced RNA degradation. Cells in culture for example are not subjected to the anti-vascular effects of radiation (Fenton et al., 2001; El Kaffas et al., 2013), which could be expected to reduce RNA integrity.

Figure 4A:
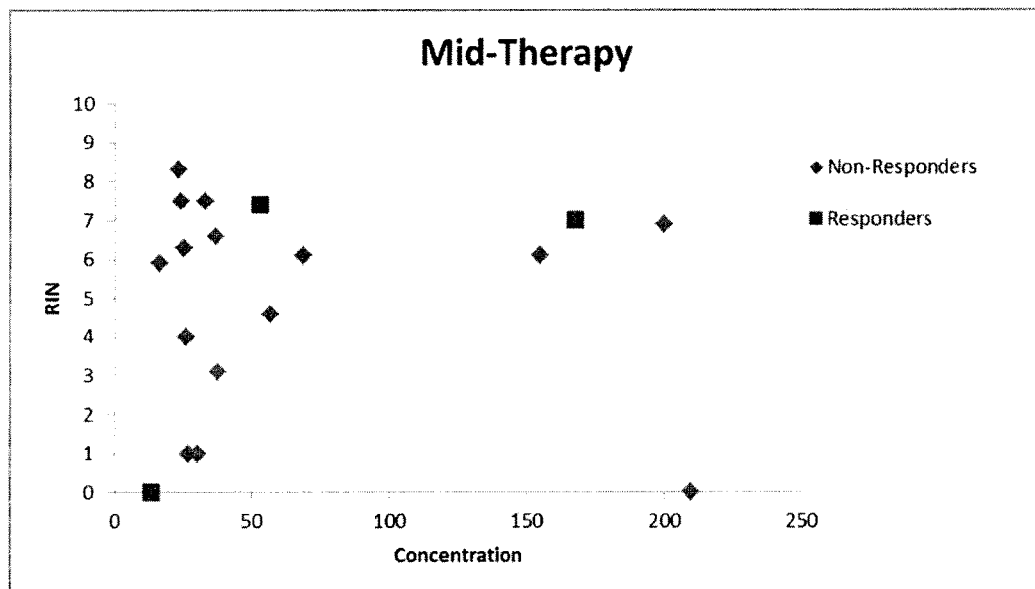
In FIG. 4A, tumour samples were taken at mid-treatment (after FEC); one Responder sample out of three had a low RNA concentration and a low RN value.
Figure 4B:
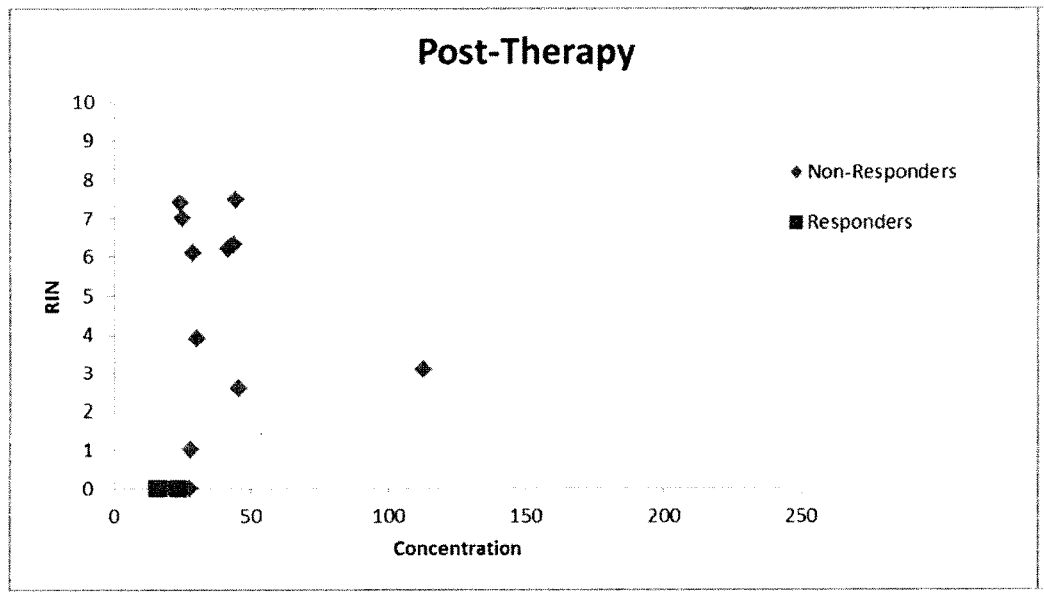
In FIG. 4B, tumour samples were taken after radiation and docetaxel; both Responder samples had low RNA concentrations and low RIN values.

As demonstrated in for example FIG. 4b, patients who exhibited a pathological complete response (pCR) had decreased RNA integrity and decreased RNA concentration post-treatment when treated with FEC-D and radiation A further aspect includes a method for evaluating a patient derived cancer cell sample, the method comprising:

a) obtaining a cancer cell sample from a subject after the subject has been exposed to a radiation dose;

b) assaying the cancer cell sample to obtain a RNA integrity value and optionally a RNA concentration of the cancer cell sample.

In an embodiment, the method further comprises comparing the RNA integrity value and optionally the RNA concentration of the patient cancer cell sample to a response threshold wherein a decreased RNA integrity and/or RNA concentration of the patient cancer cell sample compared to the response threshold is predictive that the patient is responsive to the radiation therapy and a comparable or an increased RNA integrity and optionally the RNA concentration of the patient cancer cell sample compared to the response threshold is predictive the patient is unresponsive to the radiation treatment.

In an embodiment, the cancer cell sample is selected from a breast cancer cell sample or an ovarian cancer cell sample.

The cancer cell sample can be obtained from a cell line and/or obtained from a patient. For example, the cancer cell sample can be obtained in a cytological or histological biopsy. The biopsy can be for example a needle core biopsy or fine needle aspirate or a biopsy or resection obtained during surgery.

For example, for ovarian cancer cell sample can comprise peritoneal fluid, and/or be a cell scrape, a tumour fine needle aspirate (FNA) and/or core biopsy.

In an embodiment, the response is a therapeutic response e.g. the breast cancer or ovarian cancer cell response to the radiation treatment and/or regimen is sufficient to provide a therapeutic benefit to the subject. Therapeutic response is for example predictive of clinical outcome post treatment.

In an embodiment the clinical outcome is a positive treatment outcome. In another embodiment the treatment outcome is a negative treatment outcome.

The extent or degree of RNA degradation can be associated with treatment response. Extensive degradation for example can be associated with pathological complete response. A lesser degree of degradation can be associated with lesser than pathological complete response. For example, a subject may not achieve pathological complete but may exhibit some RNA degradation during and/or post-treatment. Such a subject may for example, be treated in a subsequent treatment regimen less aggressively than a subject with no response.

In an embodiment, the positive treatment outcome predicted is complete pathologic response following treatment. In an embodiment, the positive treatment outcome predicted is reduced risk of disease progression, increased likelihood of disease free survival and/or increased overall survival. In an embodiment, the negative treatment outcome predicted is an increased risk of disease progression, decreased survival and/or recurrence. The risk of disease progression, length of disease free survival and/or other outcomes are, for example, relative to the average or median risk of progression of responders and/or non-responders of patients with the same disease and/or treatment.

As demonstrated for example in FIG. 4b, non-PCR responders could be segregated from pathological complete responders in terms of RNA integrity alone or in combination with RNA concentration.

Another aspect includes a method of identifying non-responding patients comprising:
  a) obtaining a cancer cell sample from the patient after the patient has been exposed to a radiation dose;
  b) assaying the cancer cell sample to obtain a RNA integrity value and/or a RNA concentration;
  c) comparing to a response threshold ; and
  c) identifying patients having a RNA integrity value indicative of RNA integrity and/or RNA concentration that is above the response threshold.

In an embodiment, the cancer is selected from a breast cancer cell sample or an ovarian cancer cell sample.

Yet a further aspect includes, a method of predicting a treatment outcome of a patient having cancer such as breast cancer or ovarian cancer, the method comprising: assaying a cancer cell sample obtained from the subject to obtain a RNA integrity value and/or RNA concentration for the cancer cell sample, wherein the subject has been treated with a radiation dose, wherein a RNA integrity indicated by the RNA integrity value that is below a response threshold predicts subject/cancer response to the radiation treatment and a decreased risk of progression; and a RNA integrity indicated by the RNA integrity value and/or RNA concentration that is higher than the response threshold predicts subject/cancer resistance to the radiation treatment and an increased risk of disease progression.

In an embodiment, a RDI value of 3 or less indicates non-response to radiation, for example wherein RDI is calculated based on (Intermediate Area+LowC Area)/(28S Area+18S Area).

The methods can be employed for example in a method of treatment.

Accordingly, a further aspect includes a treatment method comprising:
  a) exposing a patient with cancer, optioanally breast cancer or ovarian cancer, to a radiation dose;
  b) obtaining a cancer cell sample after administration of to the radiation dose,
  c) assaying the cancer cell sample to obtain a RNA integrity value and/or a RNA concentration of the cancer cell sample; and
  d) continuing the treatment when the RNA integrity (e.g. as indicated by the RNA integrity value) and/or the RNA concentration is decreased compared to a response threshold and changing the treatment when the RNA integrity value and/or the RNA concentration is comparable or increased compared to the response threshold.

The treatment can be changed for example by employing radiosensitizing agents during radiation therapy, modifying the dose and/or schedule of the radiation and/or chemotherapy and/or adding or changing the chemotherapy.

In an embodiment, the cancer cell sample is a breast cancer cell sample obtained from a breast cancer patient. In another embodiment, the breast cancer is Her2+, basal subtype or luminal B subtype. In another embodiment, the breast cancer patient has locally advanced breast cancer (LABC).

In another embodiment, the cancer cell sample is an ovarian cancer cell sample obtained from an ovarian cancer patient.

In another embodiment, the cancer cells are cancer selected from endometrial cancer, non-melanoma skin cancer, head and neck cancer, breast cancer, lung cancer such as non-small cell lung cancer, cervical cancer, anal cancer or prostate cancer. Radiation sensitivity can vary, depending upon tumour subtype for example as in lung cancer (Johung et al. 2013 Clin Cancer Res. 19(22)) and endometrial cancers (Ruyck et al. Int. J. Radiation Oncol.Biol Phys. 65: 1240) as well as breast cancer (Djuzenova et al, Radiation Oncology 8:98).

Radiation can be used for radiation sensitive tumours including for example lymphoma, liposarcoma, often in conjunction with chemotherapy. Radiation is often used for localized cancers not accessible to surgery and for local palliation of less radiosensitive cancers that have spread and are resistant to chemotherapy. Accordingly in an embodiment, the cancer cells are cancer selected lymphoma and liposarcoma.

RNA integrity may be used to predict response in patients. Breast cancer and ovarian cancer cells have increased RNA degradation even in the absence of drug; seen for example in MCF-7 and A2780 cells described in the Examples.

MCF-7 and SkBr3 cells both show signal induced RNA degradation effects which are detected by RDI. MCF-7 cells also have comparable RNA degradation effects caused by Epirubicin and/or Docetaxel.

Breast cancer tumours have variable responses to radiotherapy[63]. Molecular signatures/heat shock protein expression are currently under investigation as indicators of radiation response. Markers that can identify which tumours are responding would be useful.

Radiation can cause DNA damage and RNA damage[64,65].

Radiation induced RNA damage has been identified in lymphocytes[65], MCF-7 cells[66], and HeLa cells[67].

In an embodiment, the response threshold comprises a RNA integrity value. In a further embodiment, the response threshold comprises both a RNA integrity value and a concentration value.

The response threshold can be derived from an untreated cancer patient such as a breast cancer or ovarian cancer patient or be a standard derived from a plurality of untreated cancer patients (e.g. cells derived from untreated breast cancer or ovarian cancer patients or obtained prior to treatment e.g. from one or more pretreatment samples e.g. controls).

For example, the response threshold corresponds to a pretreatment RNA integrity value and optionally RNA concentration. For example, the response threshold can correspond to the RNA integrity value of a biopsy RNA sample taken from the subject or two or more subjects prior to initiating therapy or reference values from tumours of similar patients prior to therapy. A decrease in RNA integrity compared to the pretreatment RNA integrity value for example, would indicate treatment response and/or positive treatment outcome and for example a comparable RNA integrity value of the cancer cell RNA to the pretreatment RNA integrity value, would indicate resistance negative treatment outcome.

The response threshold can also be derived a patient whose response is known (e.g. responder or non-responder) or be a standard derived from a plurality of patients whose response is known.

In an embodiment, the response threshold is derived from an unresponsive patient cancer cell sample and/or a responsive patient cancer cell sample and/or is a standard derived from a plurality of unresponsive patient cancer cell samples and/or a plurality of responsive patient cancer cell samples.

In embodiments, a patient RNA integrity value indicative of RNA integrity and/or a RNA concentration that is below a response threshold is indicative the cancer is responding to the radiation treatment (and/or radiation plus chemotherapeutic agent and/or regimen) and/or predicts a positive treatment outcome; and/or a patient RNA integrity value indicative or RNA integrity and/or a RNA concentration that is greater than a response threshold is indicative the cancer is resistant to the radiation treatment (and/or radiation plus chemotherapeutic agent and/or regimen) and/or predicts a negative treatment outcome.

In an embodiment, the response threshold is a reference or cut-off RNA integrity value from subjects with the same or similar tumour type and/or radiation comprising treatment regimen-subjects with a RNA integrity value indicative of a RNA integrity and/or a RNA concentration that is below or less than the response threshold are predicted (e.g. have an increased probability) to have a positive treatment response and/or subjects with a RNA integrity value indicative of a RNA integrity and/or a RNA concentration that is above or higher than the response threshold are predicted to have a negative treatment response.

In another embodiment, the response threshold corresponds to the mean (e.g. average) RNA integrity value and/or mean RNA concentration for responders and/or non-responders, for example. In an embodiment, the mean RNA integrity value is an average of the mean RNA integrity in cancer cell samples or ovarian cancer cell samples from cancer subjects respectively that respond to a radiation treatment (alone or in combination with a chemotherapeutic agent) and/or the mean RNA integrity value is an average of the mean RNA integrity in cancer cell samples from cancer subjects that do not respond to treatment. In another embodiment, the response threshold corresponds to a threshold of high negative or positive predictive value or high area under the curve by receiver operator curve analysis or other probability analysis methods.

In an embodiment, more than one response threshold can be used. For example, RNA integrity values measured using RDA together with or separate from RNA concentration can be stratified into multiple zones such as three zones, for example Zone 1: non-responders, high negative predictive value, Zone 2: intermediate to include partial responders (some drug effect but insufficient to achieve response; this zone may include for example up to 15% of responders), and Zone 3: which is selected to include for example 85% of responders such as pathological complete responders and subjects with increased disease free survival (DFS), high positive predictive value. It has been found for example that patients treated with chemotherapy and which demonstrate signal induced RNA degradation falling within zone 3 have increased DFS even if they do not exhibit pCR. The increased DFS is similar to the pCR population. It is expected that radiation comprising regiments where the RNA integrity value similarly identifies patients as falling with zone 3, will have similar DFS benefit. Other scales and/or formats for risk assessment based on RNA integrity data could be used, as would be understood by a person skilled in the art.

RDA which can be used for assessing radiation induced RNA integrity changes, in at least one embodiment, comprises obtaining at least one electropherogram dataset corresponding to a cancer cell sample comprising cellular RNA optionally at a time point before, during or after the treatment; determining values for features from the at least one electropherogram dataset by using two identifying ranges to accommodate possible shifting of 18S and 28S peaks, detecting the 18S and 28S peaks, and calculating the features derived at least in part based on the located 18S and 28S peaks; and optionally determining an RDA score based on a combination of the values of the features.

In an embodiment, the method comprises obtaining at least one electropherogram dataset corresponding to a cancer cell sample comprising cellular RNA at a time point before, during or after the treatment; determining values for features from at least two shifted regions of the at least one electropherogram dataset, the shifting being due to the treatment; and optionally determining an RDA score based on a combination of the values of the features.

In an embodiment, the RDA, comprises accessing at least one electropherogram dataset corresponding to a unique biological sample comprising cellular RNA at a time point before, during or after the treatment; determining values for features from the at least one electropherogram dataset by using two identifying regions to accommodate possible shifting of 18S and 28S peaks, detecting the 18S and 28S peaks, and calculating the features derived in part based on the located 18S and 28S peaks; and optionally determining an RDA score based on a combination of the values of the features.

In another embodiment, the RDA method comprises obtaining at least one electropherogram dataset corresponding to a cancer cell sample comprising the cellular RNA at a time point; defining an 18S peak and a 28S peak from the at least one electropherogram dataset; determining at least one parameter value for both the 18S peak and the 28S peak; redefining at least one of the 18S peak and the 28S peak when required according to one or more rules applied to the at least one parameter value; determining an 18S peak area and a 28S peak area; and determining an RDA score based on at least one of the 18S peak area and the 28S peak area.

Figure 12:
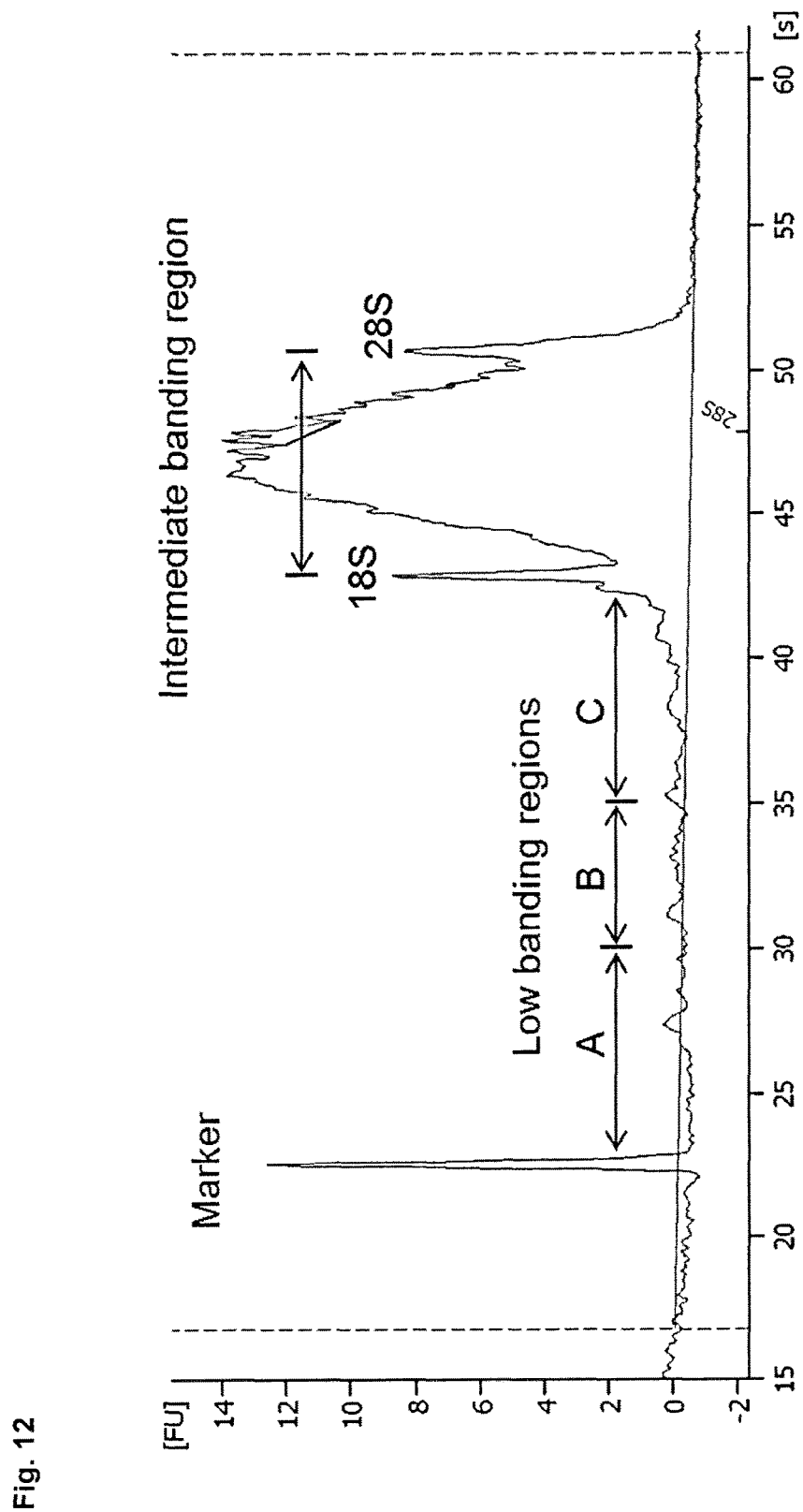
FIG. 12: is a graph of an example electropherogram in which the 18S peak, the 28S peak, the intermediate banding region, the low C banding region, the low B banding region, the low A banding region and the marker region are defined.
Figure 13:
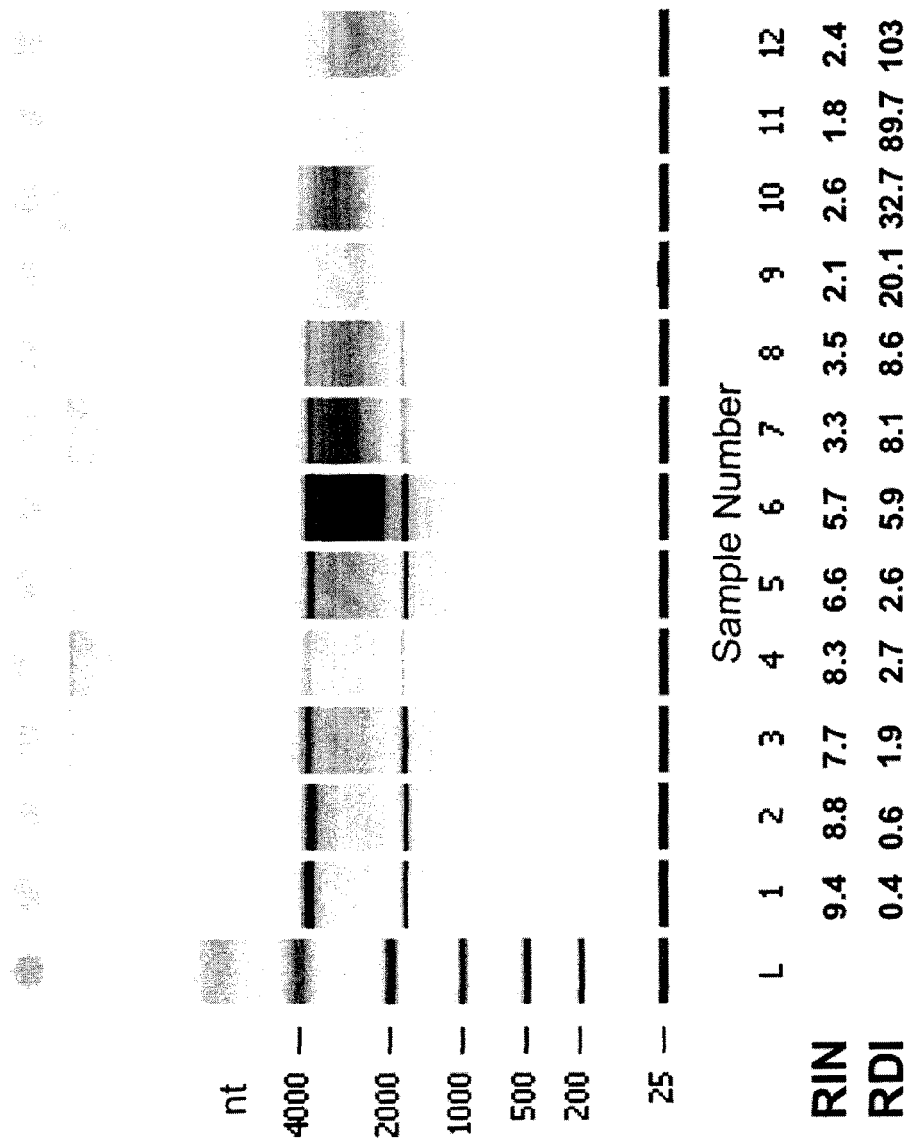
FIG. 13: is an image of a gel of electrophoretically separated RNA samples and corresponding RIN and RDI values for each sample.

FIG. 12 shows different features of the electropherogram that can be used to calculate RDI values.

For example, the features can include one or more of the area of an 18S peak, the area of a 28S peak, the area of an intermediate banding region, the area of a low banding region, the area of one or more band sub-regions, and the total area. The total area is the sum of the area of the 18S peak, the 28S peak, the intermediate banding region and the low banding region. Other features can include one or more of the width of the 18S peak and the width of the 28S peak. The area of these peaks and regions can be calculated in general using well-known mathematical techniques such as the trapezoidal rule for numerical integration (Atkinson, 1989).

The low banding region can also be divided into the "low C", "low B" and "low A" sub-regions or banding regions as demonstrated in FIG. 12 for use in some RDA methods. It has been found that the low A banding region may contain RNA due to autolytic degradation as well as due to other effects and that the low C banding region is an important region in assessing the effect on RNA due to various external stimuli such as cytotoxic treatments, for example. It has also been found that in response to certain drugs, the RNA starts to spread to the low C banding region, then to the low B banding region and then to the low A banding region.

In an embodiment, the combination of features comprises a ratio of the 28S peak area to the 18S peak area, which can be represented by the expressions "28Sarea/18Sarea" or "28S:18S".

In an embodiment, the combination of features for RDA comprises a ratio of the intermediate banding region area to the addition of the 18S peak area in the shifted 18S region and the 28S peak area in the shifted 28S region, which can be represented by the expression "intermediate area/(18Sarea+28S area)". In an embodiment, the combination of features is (Intermediate Area+LowC Area)/(28S Area+18S Area).

In another embodiment, the combination of features for RDA comprises a ratio of the low banding region area to the addition of the 18S peak area in the shifted 18S region and the 28S peak area in the shifted 28S region, which can be represented by the expression "low banding area/(18S+28S)".

In an embodiment, RDIs are stratified into 3 zones.

RNA concentration when plotted against RNA integrity values such as RDI values can provide additional information. For example, the lower the RNA concentration in the sample, for a given RDI the less absolute amount of residual normal RNA present.

In another embodiment, the response threshold is selected from a mean maximum RNA integrity, median maximum RNA integrity, mean RNA integrity, median RNA integrity, mean minimum RNA integrity, and median minimum RNA integrity of responders and/or non-responders.

In another embodiment, the response threshold is selected from a mean maximum RNA concentration, median maximum RNA concentration, mean RNA integrity, median RNA concentration, mean minimum RNA concentration, and median minimum RNA concentration of responders and/or non-responders.

In an embodiment, the RNA integrity value is compared to a response threshold when for example the response threshold is derived from a control such as a pretreatment control or untreated control for example, by one or more probability analysis methods. For example, the control can be a subject control, such as a pretreatment sample from the subject. In an embodiment, where the control is a pretreatment subject control, a decrease in the RNA integrity value and/or a RNA concentration compared to the pretreatment subject control is indicative or cancer responsiveness and/or positive treatment outcome. In another embodiment, where the control is a pretreatment subject control, a comparable RNA integrity value and/or a RNA concentration—and/or stable RNA integrity value and/or RNA concentration-compared to the pretreatment subject control is indicative of cancer resistance to the radiation treatment and/or negative treatment outcome post treatment. The control can be a population pretreatment control, for example an average, minimum, or maximum RNA integrity value or RNA concentration or reference range for two or more subjects with cancer, optionally breast or ovarian cancer, prior to treatment.

In an embodiment, the response threshold predictive of responsiveness comprises RNA integrity and/or concentration that is decreased by at least 10%, at least 20%, at least 30%, at least 40%, at least 50%, at least 60%, at least 70%, at least 80% or at least 90% below a untreated control such as a pretreatment value.

In an embodiment, the RNA integrity value and/or RNA concentration indicative of responsiveness and/or positive treatment outcome is decreased at least by 20%, at least 25%, at least 30%, at least 35%, at least 40%, at least 50%, at least 60%, at least 70%, at least 80% or at least 90% below a control such as a pretreatment sample.

In an embodiment, the RNA integrity value and/or RNA concentration indicative of resistance (e.g. or non-responders) and/or negative treatment outcome is decreased less than 40%, less than 35%, less than 30%, less than 25%, less than 20%, or less than 10% or is increased or comparable compared to a control.

In another embodiment, the cancer cell sample is obtained after the patient has received 1, 2, 3, 4, 5, 6, or more doses of radiation treatment. In an embodiment, the cancer cell sample is obtained after the patient has completed the radiation treatment and optionally any adjunct treatment.

In an embodiment, the patient treatment comprises a dose of a chemotherapeutic agent.

In clinical practice radiation can follow chemotherapy. It is likely that the combination—whether sequential or concurrent would result in increased signal induced RNA degradation.

In a further embodiment, the chemotherapeutic agent is selected from anthracyclines, taxanes and combinations thereof, preferably wherein the chemotherapeutic agent comprises epirubicin, docetaxel sunitinib or combinations thereof. In another embodiment, the taxane is paclitaxel, docetaxel, larotaxel, Abraxane, docoxahexaenoic acid-linked paclitaxel, paclitaxel polyglumex, Ortataxel, Genexol, liposomal-encapsulated paclitaxel, and paclitaxel in a Vitamin E emulsion.

In an embodiment, the taxane is docetaxel or paclitaxel.

In an embodiment, the chemotherapeutic agent is administered in a chemotherapy regimen e.g. subsequent to one or more doses of radiation. In another embodiment, one or more cancer cell samples comprising cancer cell RNA, are obtained at one or more times during chemotherapy (after 1, 2, 3, or 4 cycles, and/or any number of cycles or doses) and/or after completion of the chemotherapy regimen. In another embodiment, one or more RNA samples correspond to breast cancer or ovarian cancer cell samples obtained at one or more times during chemotherapy (after 1, 2, 3, or 4 cycles, and/or any number of cycles or doses) and/or after completion of the chemotherapy regimen.

Cancer cell samples are treated in a manner to minimize RNAse activity, for example, cancer cell samples are placed immediately in RNA preservative such as RNAlater (Qiagen) or other RNA stabilization reagent or RNA preservative with RNAse inhibitor or flash frozen for example to −80° C., for example using liquid nitrogen. A person skilled in the art would be familiar with the steps taken for obtaining and storing cancer cell and RNA samples.

In an embodiment, RNA is isolated from the cancer cell sample and the RNA integrity value and/or RNA concentration is measured on the isolated RNA.

In an embodiment, RNA is isolated/purified from the cancer cell sample, optionally the breast cancer cell sample or the ovarian cancer cell sample which is obtained from the patient. For example, RNA can be isolated using methods and kits known in the art, including for example Trizol based isolations, column based kits such as total RNA extraction columns and kits. An example of a RNA isolation method is provided in Example 1. In another embodiment, the method is performed on pre-isolated/purified RNA.

In an embodiment, the method comprises obtaining a cancer cell sample, optionally a breast cancer cell sample or an ovarian cancer cell sample after the patient (or cells) has/have received a radiation dose, isolating and/or purifying RNA from the cancer cell sample to provide an isolated/purified RNA sample comprising cancer cell RNA. The RNA sample is assayed for RNA integrity and optionally for RNA concentration.

The RNA integrity value can be determined for example by any method that assesses the state of RNA degradation in cancer cell RNA.

In an embodiment, the RNA assessed is denatured. In an embodiment, the RNA assessed is non-denatured.

In an embodiment, the RNA integrity value is determined by calculating a RNA integrity number (RIN) for example using a method that involves using microfluidics, microcapillary electrophoresis, and fluorescent dyes, for example using an Agilent Bioanalyzer machine, an Experion® Capillary Electrophoresis System with its equivalent RNA Quality Index (RQI), Nanodrop® (Thermo Scientific, Inc.) or other equivalent systems, such as those manufactured by Applied Biosystems, Lumex, or Beckman Coulter Corporation or similar system. In an embodiment, the method comprises separating the RNA by microcapillary electrophoresis, detecting RNA for example with fluorescent dye and quantitating RNA integrity.

Recently, microcapillary electrophoresis has been used increasingly to assess RNA integrity, particularly since only nanogram quantities of RNA are required. One such platform, the Agilent® 2100 Bioanalyzer (Agilent Technologies, Inc., U.S.A.) uses microfluidics technology to carry out electrophoretic separations of RNAs in an automated, reproducible manner (Mueller, O. et al., Electrophoresis 21 (2000) 128-134). The Agilent® 2100 Bioanalyzer is now used in many laboratories for the assessment of RNA integrity. The development of software for the Agilent® Bioanalyzer allows calculation of an RNA integrity number (RIN) for each sample after capillary electrophoresis. (Schroeder, A. et al., *BMC. Mol. Biol.* 7 (2006) 3; Imbeaud, S. et al. *Nucl. Acids Res.* (2005), 33, 6, e56, 1-12). This software incorporates an algorithm which quantifies the amounts of multiple RNAs in the electropherogram of a given RNA sample and assigns a RIN value based on this assessment.

For example the Agilent Bioanalyzer uses fluorescent dyes that bind to nucleic acid to evaluate RNA concentration and integrity. RNA moves through a separation channel of a RNA chip, and intercalating dye binds the RNA. The fluorescence of these molecules is measured as they pass a detector.

In an embodiment, between 20-250 ng of RNA is assessed or any number in between. In another embodiment, about 0.5 ng about 1 ng, about 5 ng, about 10 ng, about 20 ng, about 30 ng, about 40 ng, about 50 ng is assessed. In another embodiment. The concentration of the RNA sample is optionally at least 5 ng/µL, at least 6 ng/µL, at least 7 ng/µL or at least 8 ng/µL.

In an embodiment, the RNA integrity value is expressed as an RNA integrity number (RIN), wherein the RIN comprises a calculation of RNA integrity of multiple RNAs, preferably wherein the RIN is calculated using one or more of a RIN algorithm, an analytic electrophoresis system, or a RNA chip.

In an embodiment, a RIN indicative of cancer responsiveness and/or positive treatment outcome is less than 4.5, less than 3.5, less than 3, less than 2.5, less than 2, less than 1.5 and/or less than 1. Accordingly in an embodiment the response threshold is about 4.5, about 4.0, about 3.9, about 3.8, about 3.7, about 3.6, about 3.5, about 3, about 2.5, about 2, about 1.5 or about 1 and a cancer cell RIN below the response threshold is indicative of response and/or positive treatment outcome.

In an embodiment, a RIN indicative of cancer resistance and/or negative treatment outcome is greater than 5, greater than 5.5, greater than 6, greater than 6.1, greater than 6.2, greater than 6.3, greater than 6.4, greater than 6.5, greater than 7, greater than 7.5 or greater than 8 and a cancer cell RIN higher than a response threshold of about 5,about 5.5,about 6, about 6.1, about 6.2, about 6.3, about 6.4, about 6.5, about 7, about 7.5 or about 8 is indicative of resistance and/or negative treatment outcome.

In an embodiment, the RNA integrity is measured by calculating a 28S: 18S ribosomal (rRNA) ratio (e.g. 28S/18S rRNA ratio).

A 28S rRNA: 18S rRNA ratio can be determined for example by using for example denaturing agarose gel systems which can include for example either formaldehyde and MOPs buffer, or glyoxal in the loading buffer, to denature the RNA allowing molecules to run by size. The 28S and 18S rRNA bands can be visualized for example by ethidium bromide staining or other more sensitive dyes such as RiboGreen®.

For example, RNA integrity can be evaluated by visualization of RNA bands under ultraviolet light after gel electrophoresis and staining of the gel with ethidium bromide. Typically, the intensity values for the 28S and 18S rRNA bands are determined by film densitometry and a 28S/18S rRNA ratio computed. RNA is considered of high quality if the 28S/18S rRNA ratio is about 2.0 or higher.

In an embodiment, the RNA integrity value and/or the 28S:18s rRNA ratio is determined using spectroscopy, for example by assessing UV absorbance at 280:260. In an embodiment the RNA integrity value is a ratio of 28S rRNA and 18S rRNA.

In a further embodiment, the RNA integrity value is determined by assessing the RNA integrity of a subset of RNAs or fraction of total RNA. In an embodiment, the RNA is total RNA, ribosomal RNA or mRNA.

RNA concentration can be determined by a number of methods including for example microcapillary electrophoresis, for example using for example an Agilent Bioanalyzer machine, an Experion® Capillary Electrophoresis System with its equivalent RNA Quality Index (RQI), Nanodrop® (Thermo Scientific, Inc.) or other equivalent systems, such as those manufactured by Applied Biosystems, Lumex, or Beckman Coulter Corporation or similar system. The RNA concentration can be based on UV absorbance, for example by assessing UV absorbance at 280:260. Either and/or both RNA concentration can be assessed.

In an embodiment, the RNA integrity value is measured. In another embodiment, both the RNA concentration and the RNA integrity are measured.

In addition, one or more cancer samples can be assessed. For example samples can be obtained before starting radiation treatment, after one or more doses and/or upon completion.

In another embodiment, two or more cancer cell samples are obtained. For example, the samples can be taken at different time points for example after 1 dose, after 3 doses of radiation and/or in combination with cytotoxic, optionally chemotherapy treatment.

In an embodiment, the biopsy is divided into two or more cancer cell samples and two or more RNA samples are isolated/purified from the cancer samples and the RNA integrity value and optionally the RNA concentration is obtained for each. In an embodiment, an average RNA integrity value or RNA concentration of two or more RNA samples is used. In another embodiment, the highest or maximum RNA integrity value of the two or more RNA samples is used.

This approach to monitoring treatment response is expected for example to permit non-responding patients (e.g. identified as having moderate to high RNA integrity after initiation of treatment) to be switched to other treatments (surgery, other radiation doses, addition or switch to other drugs) without completing the remaining cycles of the ineffective regimen. This may spare patients the toxic side effects of regimens to which their cancers are not responding.

The methods described herein can for example be used to assess and/or stratify subjects in a clinical trial.

A further aspect comprises a method comprising sending a cancer cell sample optionally a breast cancer or an ovarian cancer cell sample or RNA sample derived therefrom to a testing site, wherein the sample is for example packaged in a RNAse free vessel and optionally resuspended in a lysis buffer, RNA isolation and/or stabilization composition optionally comprising RNAse inhibitors, the vessel labeled with an identifier permitting, for example, anonymous testing; and receiving from the testing site an assessment of the sample's RNA integrity, including a score (e.g. zone 1, zone 2 or zone 3) or other indicator indicating the risk of treatment failure. The risk assessment can be provided for example to a medical practitioner, who will use the risk assessment based on RNA quality data (in addition to other data) to decide on the best treatment option to recommend to his or her patient.

III. Kits

A further aspect includes a kit for use in a method described herein comprising a RNA isolating composition and an RNAse free vessel for receiving the tumour and/or RNA sample, wherein the vessel is optionally labeled with an identifier optionally permitting for anonymous testing.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Incidence, Mortality, and Treatment of Breast Cancer

Breast cancer is the most common cancer diagnosis in women, with 22,300 and 5,300 Canadian women being diagnosed with and dying of the disease in 2007, respectively[1]. Although treatments have improved both survival and progression-free survival for early and metastatic breast cancer patients, those with locally advanced breast cancer (LABC) have significantly poorer treatment outcome. LABC is traditionally defined as stage IIB (T3N0) and Stage IIIA/B from the TMN classification. Clinically these tumours are greater than 5 cm in size and/or extend beyond the breast tissue into the surrounding skin or muscle, with/without matted axillary lymph nodes (N2), internal mammary nodes (N3) or ipsilateral supraclavicular lymph node involvement. LABC represents approximately 10-15% of all breast cancer cases, and the survival is estimated at 30-42% at 5 years[1] a significant portion of whom will be living with metastatic disease. However, a small subset of women who receive neoadjuvant chemotherapy and achieve a pathologic complete response (pCR), (defined as no microscopic residual invasive breast cancer following neo-adjuvant treatment) have a vastly improved 5 year disease free survival rate of 87%[2] and 5 year overall survival rates of 89%[2] and 90%[3]. As such, pCR rates have become a surrogate measure for favourable long-term outcomes in trials involving neo-adjuvant treatment, particularly since this is the only subgroup for which this value can be measured. The correlation between improved survival from locally advanced breast cancer and pCR has been identified in other studies, mainly using anthracyclines[6-8].

Improved Survival of Breast Cancer with the Use of Taxanes

In order to improve survival from breast cancer, novel cytotoxic agents have been tested following or concurrently with anthracycline chemotherapy, notably the taxanes. Docetaxel is a microtubule-stabilizing agent which induces cell-cycle arrest at mitosis and apoptosis[9,10]. It has demonstrated response rates up to 50% in anthracycline-resistant metastatic breast cancer[11-13], and superior survival when used first-line in randomized studies in the metastatic setting[14,15]. Docetaxel is most commonly given intravenously every 3 weeks. However, a randomized phase III study in the metastatic setting compared docetaxel 100 mg/m$^2$ every 3 weeks, to 35 mg/m$^2$ weekly for 3 of every 4 weeks[16]. Although response rates were lower on the weekly arm, there was no difference in progression-free survival (5.7 months vs 5.5 months; p=0.46) or overall survival (OS) (18.3 months versus 18.6 months; p=0.34). There was higher overall serious toxicity in the Q 3-week arm, (88.1% versus 55.9%; p=0.0001).

Use of Taxanes in the Neoadjuvant Setting

Based on its activity in the metastatic setting, docetaxel has been tested in randomized trials in early stage breast cancer, and demonstrated superior survival when added to anthracycline-based regimens compared to these regimens alone[17-18]. FEC-D, (fluorouracil 500 mg/m$^2$ IV, epirubicin 100 mg/m$^2$, cyclophosphamide 500 mg/m$^2$ IV every 3 weeks×3 cycles, followed by docetaxel 100 mg/m$^2$ IV every 3 weeks×3) is currently one of the most commonly employed regimens in the adjuvant post-operative setting.

Several nonrandomized studies of docetaxel have also shown activity in the locally advanced setting either as a single agent, concurrent, or sequentially with other agents[19-23]. In order to determine whether the addition of docetaxel improves outcomes in the pre-operative setting, several randomized studies have been conducted. The largest, the NSABP-27, randomized 2411 women with T1c-T3 N0-N1 disease to receive 4 cycles of AC pre-operatively, versus 4 cycles of AC followed by 4 cycles of docetaxel preoperatively, or 4 cycles of AC preoperatively followed by surgery and 4 cycles of post-operative docetaxel. Compared to preoperative AC alone, the addition of docetaxel significantly improved clinical complete response (cCR) (40.1% v 63.6%; p<0.001), pCR (13.7% v 26.1%; p<0.001) and proportion of patients with negative nodes (50.8% v 58.2%; p<0.001)[24]. With 8.5 years of follow-up, across all 3 groups, there was no difference in disease free survival (DFS) or overall survival (OS) (2). However, in the patients achieving a pCR, there was a significant improvement in DFS (HR=0.49, p<0.0001) and OS (HR=0.36, p<0.0001).

The Aberdeen Breast Group also tested the efficacy of the addition of docetaxel to an anthracycline-based regimen in the preoperative setting[25]. One hundred and forty-five women with newly diagnosed T3, T4 or TxN2 disease received 4 cycles of CVAP (cyclophosphamide 1,000 mg/m2, doxorubicin 50 mg/m$^2$, vincristine 1.5 mg/m$^2$ and prednisone 40 mg). Those who achieved a partial or complete clinical response were then randomized to either 4 more cycles of CVAP or 4 cycles of docetaxel (100 mg/m$^2$). Those who did not respond to the initial 4 cycles of chemotherapy were treated with docetaxel in a nonrandomized fashion. Intention-to-treat analysis demonstrated a higher cCR (94% v 66%, p=0.03) and pCR (31% v 16% p=0.04) with the addition of docetaxel compared to 4 more cycles of CVAP. At 38 months median follow-up docetaxel significantly improved DFS (90% v 77%; p=0.03) and OS 97% v 84%; p=0.05)[26]. A third study, the GEPARDUO study compared AC (doxorubicin and cyclophosphamide)

for 4 cycles followed by docetaxel for 4 cycles (AC-DOC) to dose—dense doxorubicin 50 mg/m$^2$ plus docetaxel 75 mg/m$^2$ every 14 days for 4 cycles with filgastrim support (ADOC) preoperatively in 913 women with T1-3 N0-2 breast cancer[27]. All endpoints including clinical response, pCR and breast-conserving surgery rates were significantly improved with the sequential AC-T (doxorubicin and cyclophosphamide followed by a taxane) over the dose dense arm. Survival end points have not yet been reported.

Use of Radiation To Further Improve Neoadiuvant Chemotherapy Response in Patients with Locally Advanced Breast Cancer?

In spite of the improved outcomes associated with the addition of taxanes to neoadjuvant chemotherapy regimens, these gains have been modest. pCR rates for non-trastuzumb-based regimens employing both anthracyclines and taxanes are still quite low (15-30%). Since the achievement of a pCR in patients is associated with strongly enhanced survival, efforts must be directed at improving pCR rates in breast cancer patients, in particular those with locally advanced disease. One possibility for improvement of pCR rates for patients with breast cancer is to combine chemotherapy with radiation therapy in the neoadjuvant setting. In other tumor sites, a combined modality approach of local radiation given concurrently with radio sensitizing chemotherapy or other agent has been employed in order to improve outcomes. These include agents such as fluoropyrimidines, platinum and more recently taxanes. Postoperative concurrent chemoradiation has long been the standard of care in locally advanced rectal cancer. Recent trials comparing preoperative to postoperative chemoradiation have demonstrated improved local control with the preoperative approach[28,29]. Furthermore, a significant improvement in pCR and DFS with preoperative chemo/radiotherapy has been reported[30]. Chemo/radiotherapy is also the standard of care for patients with unresectable head and neck cancer. The concurrent approach has demonstrated improvements in organ preservation and survival over radiation alone in multiple randomized trials[31-34]. In locally advanced non-small cell lung cancer, several randomized trials have demonstrated improved local control and survival with the use of concurrent versus sequential chemoradiation, most commonly with platinum-based chemotherapy[35-38]. Moreover, multiple small studies have been done in this patient population adding docetaxel as a radiosensitizer[39-44].

Limited published data exists for the use of neoadjuvant chemo/radiotherapy in locally advanced breast cancer. A retrospective review of 44 patients receiving concurrent chemoradiation with taxanes for stage I-IV breast cancer has been reported[45]. While this study demonstrated the safety and feasibility or concurrent chemoradiation with taxanes in locally advanced breast cancer, response rates and survival outcomes were not reported.

A second study of 44 women with stage IIB to III locally advanced breast cancer has been reported where patients received twice weekly intravenous paclitaxel 30 mg/m$^2$ for 8-10 weeks concurrent with radiation to total dose of 45 Gy, followed by surgery[46]. No grade 4 toxicities were observed in the preoperative chemoradiation phase. In the postoperative phase, the only grade 4 toxicity was leucopenia (10%). Sixteen percent of patients achieved a pCR, with 18% a pPR. There was no association between total dose of preoperative chemotherapy and pCR. A second study (in abstract form only) reported on 23 patients receiving 50.4 Gy over 6 weeks, with paclitaxel 175 mg/m$^2$ day 1, and 5FU 1000 mg/m2/day continuous infusion day 1-3 for 3 cycles every 3 weeks[48]. This was followed by 3 cycles of FEC every 3 weeks, then surgery. Grade 3 toxicities included radiation dermatitis, esophagitis, vomiting, mucositis and neutropenia. The clinical CR was 82.6%, and pCR was 52.2%. Overall 2-year survival is 80.7%.

Given the above promising findings, a phase II trial evaluating the FEC-D regimen[49] was recently conducted for locally advanced, non-inflammatory breast cancer patients given in a neoadjuvant setting, while adding concurrent radiation to the first 6 of 9 weeks of docetaxel, followed 5 weeks later by a modified radical mastectomy (which remains the surgical standard of care for LABC patients). In order to minimize the side effects of this chemotherapy and optimize its tolerability with radiation[50,51], docetaxel weekly×9 weeks was administrated (dose adjusted to 35 mg/m$^2$) rather than q3 weekly×3 cycles. For patients whose tumours were Her2-neu gene amplification positive, Herceptin was given IV q3 weekly for one year. Toxicities were then evaluated and response rates for this treatment regimen were assessed.

Moreover, in a recent clinical trial for patients with locally advanced breast cancer (NCIC-CTG-MA.22), the relationship between tumour RNA quality and response to epirubicin/docetaxel chemotherapy was assessed. Three image guided core biopsies were obtained from patients prior to, during, and immediately after administration of chemotherapy and immediately flash frozen on dry ice for subsequent storage in liquid nitrogen. RNA was isolated from the biopsies and the quantity and quality of the RNA assessed using an Agilent 2100 Bioanalyzer. RNA quality was quantified by the bioanlayzer in terms of an RNA integrity number (RIN), where a RIN of 0 represents completely hydrolyzed RNA and a RIN of 10 represents completely undegraded RNA. This study, demonstrated that chemotherapy treatment resulted in a dose-dependent reduction in tumour RIN values mid-treatment and post-treatment. Moreover, unlike tumour extent/cellularity, low mid-treatment tumour RIN values were found to be correlated with the achievement of a pCR in patients post-treatment. All patients that had a pCR post-chemotherapy exhibited a reduction in maximum tumour RIN mid-treatment (mid-treatment in the above case, was after 3 or 4 cycles of chemotherapy). In the current study of FEC-D chemotherapy with concurrent radiation, it was also assessed whether changes in tumour RNA quantity and quality took place in response to the regimen.

Methods

Administration of the FEC-D Regimen with Concurrent Radiation

A schema for the above-described study is described in FIG. 1. Thirty two patients with stage III non-metastatic, non-inflammatory locally advanced breast cancer were treated with neoadjuvant 5-Fluoro-uracil, Epirubicin, and Cyclophosphamide (FEC also referred to as CEF) q3 weekly for 4 cycles followed by weekly Docetaxel (35 mg/m$^2$) concurrently with regional radiation (45 Gy with 16 Gy boost in 25 & 5 fractions) for 6 weeks followed by an additional 3 weeks of docetaxel chemotherapy without radiation. This was followed by a modified radical mastectomy. Patient and tumour characteristics were recorded at baseline and following treatment and clinical response and treatment-related toxicities noted (Table1). Image guided serial 14 gauge tumour core biopsies were taken from the patients pre-, mid-and post-treatment, and 1 mm$^3$ sections were immediately taken from the biopsies, immersed in RNAlater™, and stored frozen. In this trial "pre" is before any FEC, mid is after FEC, MID treatment is after FEC but before docetaxel with concurrent radiation therapy, and post is after radiation/docetaxel.

Isolation of RNA from Tumour Core Biopsies

RNA was isolated from image-guided tumour core biopsies of patients pre-, mid-, and post-treatment using Qiagen miRNeasy® Mini kits, following a modification of the protocol published on the manufacturer's website, http://www1.giagen.com/literature/handbooks/_literature.aspx?id=1000291. Biopsies were cut into several sections for various assays, with the section used for RNA integrity analysis placed in RNAlater. The biopsies in RNAlater were immediately dropped in 0.5 ml of RLT buffer containing β-ME (10 µl into 1 ml) in a 1.5 ml tube. The biopsies in RLT buffer were homogenized with a Coreless motor homogenizer for 5 min (from the Kontes Glass Company). The lysate was then passaged at feast 5 times through a 20-gauge needle (0.9 mm diameter) fitted to an RNase-free syringe. The sample was then centrifuged at high speed in a refrigerated microfuge at 4° C. for 3 minutes, with transfer of the supernatant to a new tube. One volume (500 µl) of 70% ethanol was then added to the supernatant and the sample mixed well by repeated pipetting. If some lysate was lost during homogenization, then the volume of ethanol was adjusted accordingly. Visible precipitates formed after the addition of ethanol in some samples did not affect the RNA isolation procedure. A maximum of 700 µl of the sample, including any precipitate, were added to a Qiagen® mini column and placed in a 2 ml collection tube. The column was centrifuged for 15 s at ≥8000×g (≥10,000 rpm) and the flow-through discarded. The remainder of the sample was then added to the column and the column centrifuged again. From this point forward, the column was then washed twice in RPE buffer and dried by centrifugation as per the manufacturer's protocol. The RNA was then eluted from the column in 30 µl of RNase-free water and the eluate reapplied and eluted from the column to increase the yield and concentration of the RNA obtained.

Assessment of RNA Quality Using an Aqilent 2100 Bioanalyzer

The above RNA samples were applied to RNA 6000 Nano Lapchips™ (purchased from Agilent Biotechnologies, Inc.) and subjected to capillary electrophoresis using an Agilent® 2100 Bioanalyzer. The protocol followed was identical to that described in the company's technical brochure for the Agilent® 2100 Bioanalyzer, available at: http://www.chem.agilent.com/scripts/LiteraturePDF.asp?iWHID=36225. The amount and quality (RIN value) of RNA from each core biopsy was then determined by the Bioanalyzer.

Results

Clinical Responses and Toxicities to FEC-D chemotherapy with concurrent radiation While 30 of the 32 patients (94%) completed the treatment protocol described above, patients experienced significant toxicities. Twenty seven patients (84%) had grade 3 or greater toxicities, including grade 3 resolving pneumonitis (6 patients), grade 3 dermatitis (6 patients) and one treatment-related death. As shown in Table 1, eight of these patients (25%) exhibited a pathologic complete response (pCR) to treatment, which is approximately twice the Ontario pCR rate for locally advanced breast cancer. Moreover, at a mean 21 months of follow-up, the relapse-free survival rate was 100% in the pCR cohort and 65% among partial responders (PRs). This suggests that the regimen, while exhibiting strong toxicity, appears to enhance the pCR and survival rate for locally advanced breast cancer. Tumours that exhibited pCRs were distributed almost equally amongst the basal (2 of 5 tumours=40%), Her2 (3 of 3 tumours=100%), and luminal B (3 of 6 tumours=50%) subtypes. No pCRs were found among the 11 patients with luminal A tumours (0%). While the numbers are small, the data suggests that FEC-D regimen with concurrent radiation appeared able to induce pCRs across a variety of breast cancer subtypes.

TABLE 1

Data on patient characteristics prior to and post-treatment in the London Clinical Study, including age, baseline nodal status and stage, completion of treatment, level of pathologic response, post-treatment nodal status and stage, pre-treatment receptor expression status, predicted tumour subtype and degree of toxicity experience by patients.

| ID | AGE | Base Stage | Path Response | Path Stage | ER | PR | Her2 | Subtype-Like | Mean 2.5 Yr F/U |
|---|---|---|---|---|---|---|---|---|---|
| 1 | 62 | Stage IIIA | PR | Stage 1 | Negative | Negative | Positive | Her2 | Died |
| 2 | 38 | Stage IIB | CR | Stage 0 | Negative | Negative | Positive | Her2 | Alive No Disease |
| 3 | 26 | Stage IIIA | CR | Stage 0 | Negative | Negative | Negative | Basal | Alive No Disease |
| 4 | 58 | Stage IIIA | CR | Stage 0 | Positive | Positive | Positive | Luminal B | Alive No Disease |
| 5 | 43 | Stage IIIA | Stable | Stage IIIA | Positive | Positive | Positive | Luminal B | Alive No Disease |
| 6 | 52 | Stage IIIA | Stable | Stage IIB | Positive | Positive | Positive | Luminal B | Alive No Disease |
| 7 | 49 | Stage IIIA | CR | Stage 0 | Positive | Positive | Positive | Luminal B | Alive No Disease |
| 8 | 63 | Stage IIIA | Prog | Stage IV | Negative | Negative | Negative | Basal | Died |
| 9 | 48 | Stage IIIA | PR | Stags IIB | Positive | Positive | Negative | Luminal A | Alive No Disease |
| 10 | 61 | Stage IIIA | PR | StageIIA | Positive | Positive | Negative | Luminal A | Died |
| 11 | 39 | Stage IIB | PR | Stage IIA | Positive | Positive | Negative | Luminal A | Died |
| 12 | 47 | Stage IIB | PR | Stage I | Positive | Positive | Negative | Luminal A | Alive No Disease |
| 13 | 43 | Stage IIB | CR | Stage 0 | Negative | Negative | Positive | Her2 | Alive No Disease |
| 14 | 49 | Stage IIIA | PR | Stage IIA | Negative | Negative | Negative | Basal | Died |
| 15 | 64 | Stage IIIA | PR | Stage IIIA | Positive | Negative | Negative | Luminal A | Died |
| 16 | 34 | Stage IIIC | PR | Stage I | Negative | Negative | Negative | Basal | Alive No Disease |
| 17 | 40 | Stage IIB | PR | Stage I | Positive | Positive | Negative | Luminal A | Alive No Disease |
| 18 | 58 | Stage IIIC | PR | Stage IIA | Positive | Positive | Positive | Luminal B | Alive No Disease |
| 19 | 42 | Stage IIIA | Stable | Stage IIA | Positive | Positive | Negative | Luminal A | Alive No Disease |
| 20 | 53 | Stage IIIB | CR | Stage 0 | Negative | Negative | Negative | Basal | Alive No Disease |
| 21 | 44 | Stage IIB | PR | Stage 1 | Positive | Positive | Positive | Luminal B | Alive No Disease |
| 22 | 45 | Stage IIB | PR | Stage IIA | Positive | Negative | Negative | Luminal A | Alive No Disease |
| 23 | 57 | Stage IIIA | CR | Stage O | Positive | Negative | Positive | Luminal B | Alive No Disease |
| 24 | 60 | Stage IIB | PR | Stage IIB | Positive | Positive | Negative | Luminal A | Alive WITH Disease |
| 25 | 50 | Stage IIIA | PR | Stage IIB | Negative | Negative | Negative | Basal | Alive WITH Disease |
| 26 | 44 | Stage IIIB | PR | Stage IIA | Positive | Positive | Negative | Luminal A | Alive No Disease |

TABLE 1-continued

Data on patient characteristics prior to and post-treatment in the London Clinical Study, including age, baseline nodal status and stage, completion of treatment, level of pathologic response, post-treatment nodal status and stage, pre-treatment receptor expression status, predicted tumour subtype and degree of toxicity experience by patients.

| ID | AGE | Base Stage | Path Response | Path Stage | ER | PR | Her2 | Subtype-Like | Mean 2.5 Yr F/U |
|----|-----|-----------|---------------|------------|----|----|------|--------------|-----------------|
| 27 | 45 | Stage IIIA | PR | Stage IIA | Positive | Positive | Negative | Luminal A | Alive No Disease |
| 28 | 62 | Stage IIIA | PR | Stage IIIA | Positive | Negative | Positive | Luminal B | Alive No Disease |
| 29 | 51 | Stage IIIB | PR | Stage IIA | Positive | Positive | Positive | Luminal B | Alive No Disease |
| 30 | 58 | Stage IIIA | NA | Died in Tx | Positive | Positive | Positive | Luminal B | Died |
| 31 | 31 | Stage IIIC | PR | Stage IIA | Positive | Positive | Positive | Luminal B | Alive No Disease |
| 32 | 62 | Stage IIIA | PR | Stage IIIA | Positive | Positive | Negative | Luminal A | Alive No Disease |

Y = yes, N = no, PR = partial response, CR = complete response, Stab = stable disease, Prog = progressive disease.

TABLE 2

Effects of FEC chemotherapy followed by docetaxel treatment with concurrent radiation therapy in LABC patients. Toxicities included radiation pneumonitis and dermatitis and one death during treatment from acute respiratory distress. Syndrome (ARDS). Two year survival post-treatment was higher for patients achieving pCR. pCRs occurred in patients with tumours of the Her2, luminal B, and basal subtypes, but were absent in luminal A tumours.

| Category | Quantity |
|----------|----------|
| TOXICITY | |
| Radiation Pneumonitis | 25% |
| Radiation Dermatitis | 25% |
| ARDS Death | N = 1 |
| 2.5 YEAR SURVIVAL | |
| Patients With pCR | N = 7, 100% |
| Patients Without pCR | N = 24, 62% |
| pCR BY TUMOUR SUBTYPE | |
| ER+/PR+ or −/Her2− (Luminal A) | N = 0/12 = 0% |
| ER−/PR+ or −/Her2+ (Luminal B) | N = 3/10 = 30% |
| ER−/PR−/Her2+ (Her2) | N = 2/3 = 66% |
| ER−/PR−/Her2− (Basal) | N = 2/6 = 33% |

Figure 2:
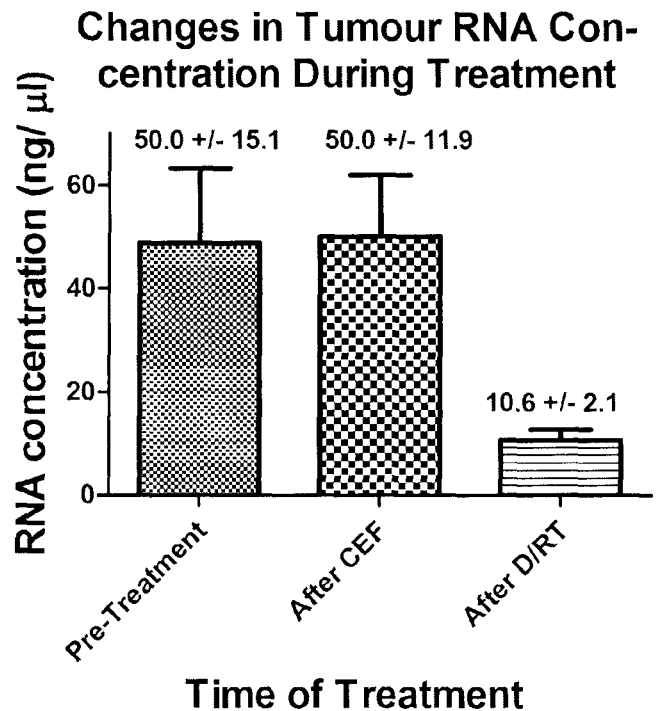
FIG. 2: Effect of FEC treatment and/or docetaxel treatment with concurrent radiation for patients in the London Clinical Trial depicted in FIG. 1. Mean tumour RNA concentrations±standard error at the various treatment times are depicted in the top panel, while the bottom panel depicts the biopsy RNA concentration values for each patient.
Figure 2:
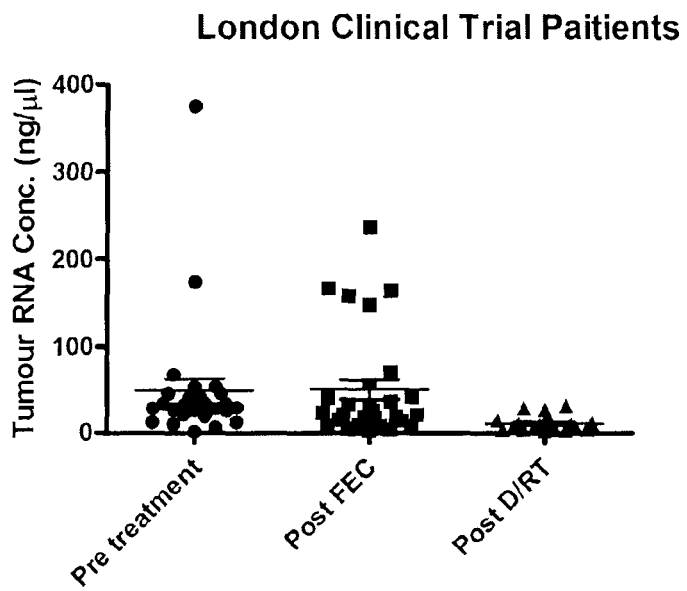
Figure 3:
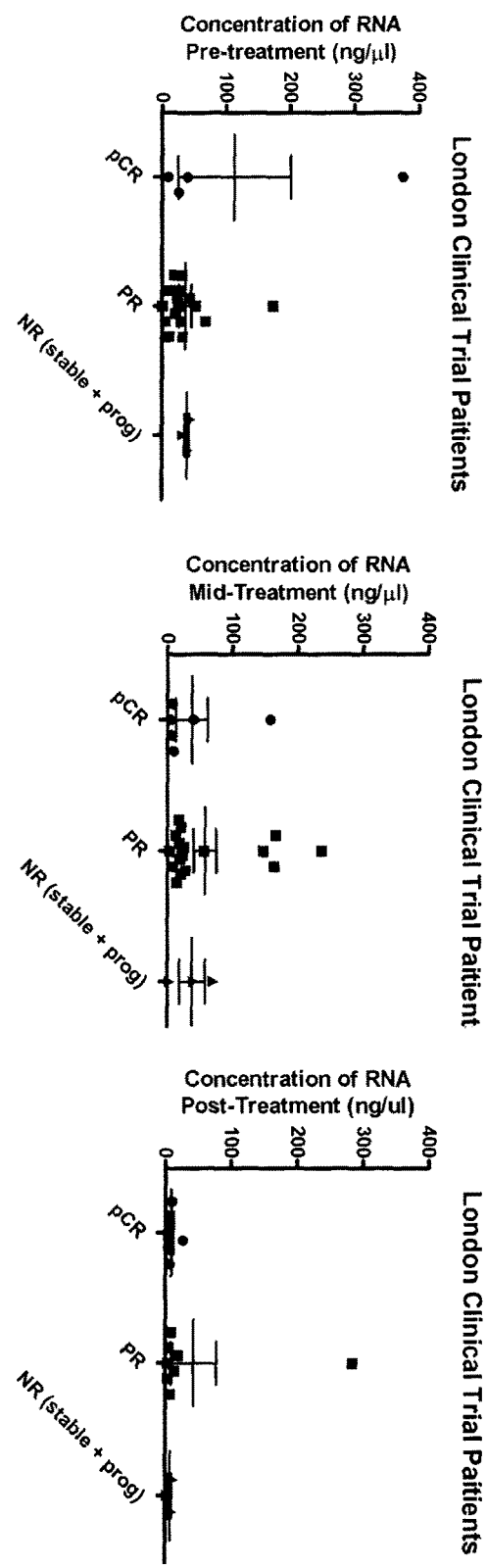
FIG. 3: Inability of tumour RNA concentration values pre-, mid-, or post-treatment by themselves to indicate degree of clinical response in the London clinical trial, which included a post-treatment pathologic complete response (pCR), a partial response (PR), or no response (NR), including the presence of stable or progressive (prog) disease.

Changes in Tumour RNA Content In Response to FEC Chemotherapy Followed by Docetaxel Chemotherapy with Concurrent Radiation Treatment It was then assessed whether, similar to the NCIC-CTG-MA.22 clinical trial, changes in tumour RNA quality or quantity could be observed during or in response to treatment and whether low RNA quality was associated with a strong clinical response upon the completion of treatment (pCR). FIG. 2 illustrates the RNA concentration values for all patient biopsies isolated prior to treatment, in the middle of treatment, and post-treatment. This plot reveals that there was some significant variability in the quantity of RNA isolated from the biopsies throughout treatment, including pre-treatment biopsies. This suggests possible variations in the preservation of RNA in the collected biopsies. In addition, the data suggests little difference in RNA concentration between pre-treatment biopsies and biopsies collected after FEC chemotherapy (mean tumour RNA concentration of 50.0±15.1 and 50.0±11.9 ng/μl, respectively). In contrast, the mean tumour RNA concentration fell significantly after the completion of the FEC-D regimen with concurrent radiation and was 10.6±2.1 nanograms/microliter. These findings suggest that the FEC chemotherapy alone is insufficient to induce reductions in tumour RNA concentration, but upon treatment with concurrent radiation therapy and docetaxel, tumour RNA content falls dramatically. Despite this treatment effect, there were no significant differences in tumour RNA concentration were observed amongst patients that exhibited a pathologic complete response post-treatment (pCR), patients that exhibited a partial response to treatment (PR), and patients with stable or progressive disease (SD or PD) post-treatment (FIG. 3). Changes in Tumour RIN Values In Response to FEC chemotherapy followed by docetaxel chemotherapy with concurrent radiation treatment.

To assess changes in tumour RNA content in during FEC-D chemotherapy with concurrent radiation treatment, all samples that were noted as "insufficient signal" for mathematical analysis were omitted An insufficient signal is one with no detectable peaks above background. As shown in FIG. 4A, in the three samples post-FEC chemotherapy but before docetaxel/radiation treatment which achieved a pCR at the end of treatment, 2 out of 3 samples demonstrated RIN values indicative of high RNA integrity or minimal RNA degradation (e.g. RIN>7 which is comparable to baseline levels). One patient sample had a very low RIN value suggestive of significant loss of RNA integrity (RIN value=n/a or 0). In the samples from non-responding patients (patients who did not achieve pCR post-treatment), little effect of FEC treatment on tumour RNA quantity or integrity could be observed when compared to pre-treatment samples.

When tumour RNA integrity was assessed after both FEC chemotherapy and docetaxel/radiation treatment, only two samples from patients that achieved a pCR post-treatment had sufficient RNA for mathematical analysis (FIG. 4B). For these two samples, both had RIN values of n/a or zero, indicative of very strong loss of RNA integrity. These two responders to treatment were strongly distinct from nonresponders based on RNA concentration and RIN values. The low RIN values are indicative of loss of normal (e.g. non-fragmented) RNA. In the nonresponders, a wide range of RIN values are noted which is indicative of a spectrum of change in tumour RNA from highly fragmented to highly intact. These results suggest that loss of RNA integrity occurred with radiation and docetaxel resulting in decreased RIN values and a loss in RNA concentration. This loss of RNA integrity correlated with a strong response to treatment (pCR). High RNA concentration and high RIN is suggestive of non-response based on the clinical data.

Example 2

Changes in Tumour Cell RNA Integrity In Vitro in Response to Radiation With or Without Docetaxel Treatment There are genomic similarities between ovarian and breast cancers (Nature 490:67-70, 4 Oct., 2012) and may show similar responses. To this end, we looked at an ovarian cancer line for its RNA response to radiation therapy.

Figure 5A:
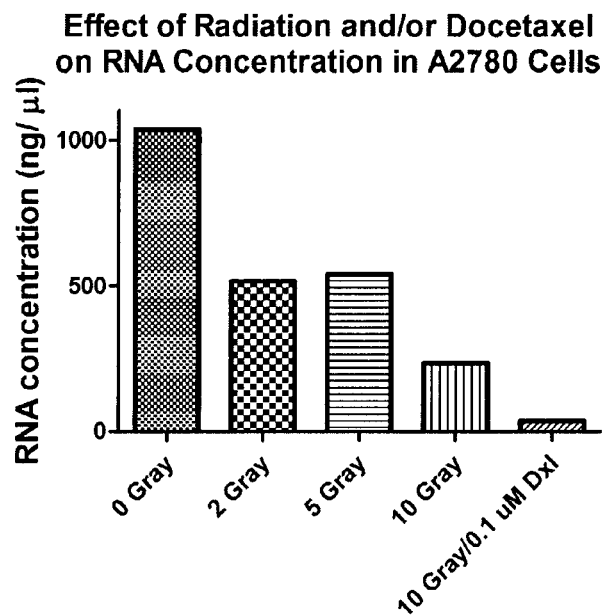
FIG. 5: Effect of various doses of radiation on RNA content (concentration) (panel A) or RNA integrity (panel B) in A2780 ovarian tumour cells. The effect of 0.1 µM docetaxel treatment with concurrent 10 Gray radiation is also depicted. Radiation treatment alone reduced RNA content and integrity in an apparent dose-dependent manner, which was strongly augmented by concurrent 0.1 µM docetaxel treatment.
Figure 5B:
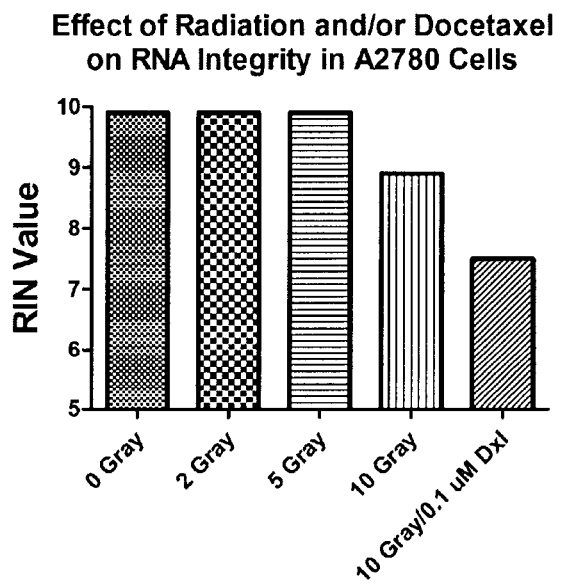

Experiments were conducted to assess whether radiation with or without docetaxel treatment could induce changes in cellular RNA concentration and/or RIN values in A2780 ovarian tumour cells. As shown in FIG. 5A, radiation treatment induced a dose-dependent change in A2780 cell RNA content, with 10 Gray of radiation inducing almost a 5-fold reduction in RNA concentration levels. Interestingly, pre-incubation of cells with 0.1 µM docetaxel further reduced cellular RNA concentration by an additional 6.5-fold, almost eliminating all RNA from the cells. In contrast under the tested conditions, radiation doses up to 5 Gray had no effect on cellular RNA integrity, as no changes in RIN values were observed compared to samples prior to radiation treatment (FIG. 5B). If cells were pre-incubated for 24 hours with 0.1 µM docetaxel prior to 10 Gray radiation treatment, the cellular RIN value decreased to 75% of pre-treatment values. There were additional decreases in RIN when radiation and chemotherapy were used together concurrently. Taken together, these findings suggest that radiation can induce reductions in cellular RNA content and reductions in RNA integrity. Moreover, the combination of both radiation and docetaxel treatment induces even stronger reductions in both cellular RNA content and RNA integrity. These observations are consistent with those described above for tumours of patients with locally advanced breast cancer, in particular for the combined therapy post-treatment, where RNA concentration fell dramatically in response to FEC-D chemotherapy with concurrent radiation therapy and where differences between between responding patients (pCR) and non-reponding patients (no pCR) appeared to be observed post-treatment.

Figure 6A:
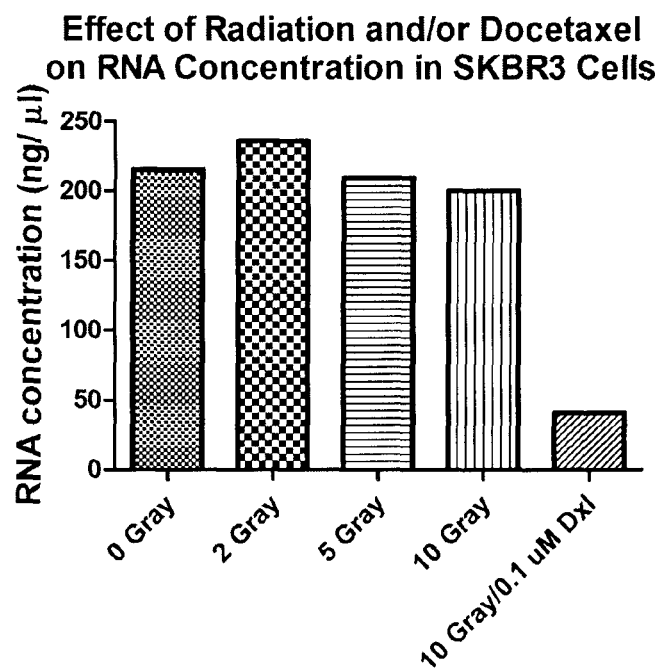
FIG. 6: Effect of various doses of radiation on RNA content (concentration) (panel A) or RNA integrity (panel B) in Her2+ SKBR3 breast tumour cells. The effect of 0.1 µM docetaxel treatment with concurrent 10 Gray radiation is also depicted. Ten gray radiation treatment alone slightly reduced RNA content, with no apparent effect on RNA integrity. Effects of 10 gray radiation on RNA content and RNA integrity was strongly augmented by concurrent 0.1 µM docetaxel treatment, in particular for RNA integrity.
Figure 6B:
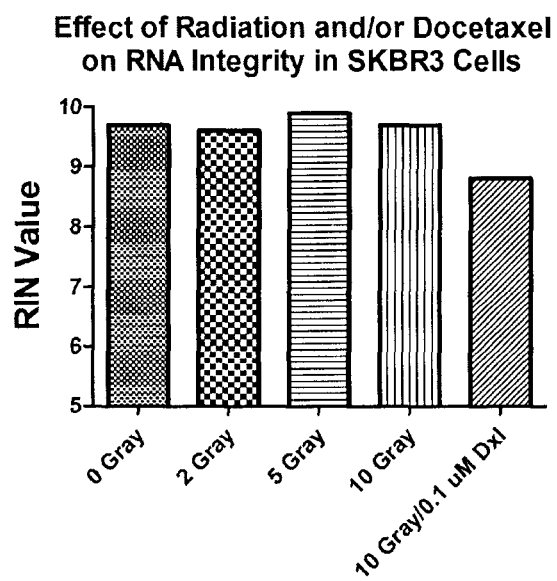

It was then examined whether similar observations could be observed in vitro for specific breast tumour cell lines. As shown in FIG. 6A, a change in RNA concentration of about 7% was observed for SKBR3 breast tumour cells in culture when treated with up to 10 Gray of radiation. If cells were pre-treated with 0.1 µM docetaxel prior to 10 Gray radiation, a 5-fold reduction in cellular RNA concentration was observed (19% of untreated cells). RNA concentration decreases 2 fold (or more) in BT-20, A2780 and MB-468 cells with radiation only. These findings suggest that in breast tumour cells in vitro (and possibly in the tumours of breast cancer patients), some changes in cellular RNA concentration may be observed by radiation treatment alone. Concurrent docetaxel treatment with radiation therapy dramatically reduces cellular RNA content, consistent with the observed findings for patients with locally advanced breast cancer treated with FEC-D chemotherapy followed by radiation treatment. Similar findings were observed when the effects of the above treatments on RIN values were examined in SKBR3 (HER2+, ER−) cells (FIG. 6B). Measurable (9%) reductions in cellular RIN values was observed in response to radiation if cells were pre-treated with docetaxel.

The identifying ranges may be initialized to a default setting and then shifted if required. For example, for the 18S and 28S peaks, the default ranges can be initially set to [39.5s, 44.95 s] and [45.05 s, 53.5 s]. On a scale of 0 to 100, the range for the 18S region is [45.85, 61.25], and that for the 28S region is [61.6, 85.75]. These ranges can then be shifted under certain conditions, such as, but not limited to the case when the marker region is not at its expected location. For example, these ranges may be shifted if the time of the marker, which is the time associated with the first peak that is a dye-only peak meaning that it does not contain any RNA but rather indicates the start of the run for the gel, is not at about 22.5 seconds. For these samples, a shift factor is calculated according to 20 equation 1:

$$rngshft = \text{marker time} - 22.5 \quad (1)$$

where marker time is the start time of the marker. The range for the 18S region is then shifted up according to [39.5+rngshft ×1.5, 44.95+rngshft ×1.5] and the range of the for the 28S region is shifted up according to [45.05+rngshft ×2.5, 53.5+25 rngshft ×2.5].

An internal standard means an RNA sample that is used as a normalizer for a particular assay. For example, when the assay comprises using an RNA chip, the internal standard can be the sample that is determined as having the smallest value for the measure: (intermediate area +low B area+low C area)/(28S area +18S area). The internal standard can be used to identify which samples are adjusted. The internal standard can be a subject sample and/or a control sample. The control sample is a sample of intact RNA or approximately intact RNA after treatment.

Figure 7A:
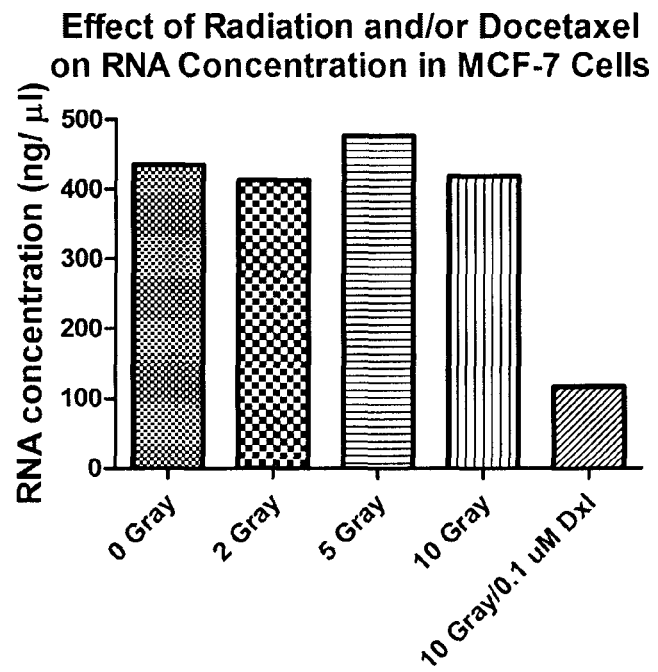
FIG. 7: Effect of various doses of radiation on RNA content (concentration) (panel A) or RNA integrity (panel B) in MCF-7 breast tumour cells [a subtype of breast tumour (luminal A)]. The effect of 0.1 µM docetaxel treatment with concurrent 10 Gray radiation is also depicted. Radiation treatment alone has little effect on RNA content and integrity, which was only slightly augmented by concurrent 0.1 µM docetaxel treatment.
Figure 7B:
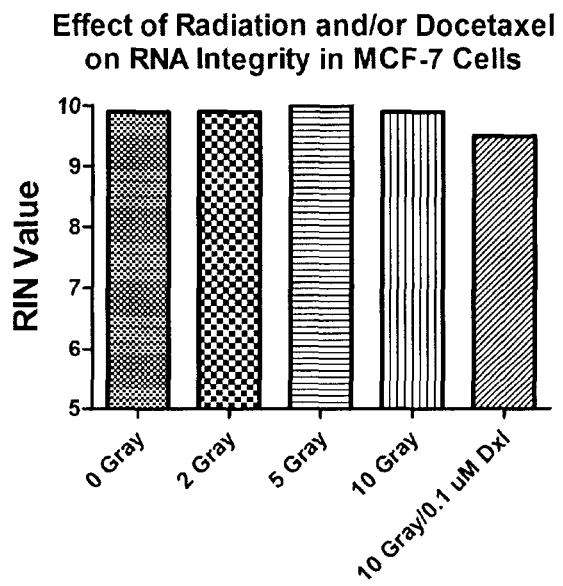

The effects of the above treatments on MCF-7 (ER+, HER2−) cells (FIGS. 7A and 7B) were examined, findings were similar to those of SKBR3 cells, with 4% and 73% reductions in RNA levels observed for the 10 Gray and 10 Gray/0.1 µM docetaxel treatments, respectively. Similarly, no significant reduction in cellular RIN values were observed for MCF-7 cells, even at the highest radiation dose (10 Gray). Moreover, only a 4% reduction in cellular RIN values were observed when cells were pre-treated with 0.1 µM docetaxel prior to the 10 Gray radiation.

Example 3

A2780 cells were treated with increasing doses of Epirubicin with and without 10 Gy radiation. A2780 cells were plated into 6 cm plates in 4 ml of RPMI culture medium. The plates were placed in the incubator and the cells were allowed to adhere overnight. The next day, the medium was removed from all plates and new media containing the appropriate epirubicin concentration (1 pM, 5 pM, 20 nM, 50 nM, and 100 nM) was added to the plates. Cells were pre-treated for 24 h with epirubicin prior to receiving radiation treatment. The following day (24 h post epirubicin drug-treatment), the cells were given 10 Gy of x-ray radiation treatment (300 kV, 9 mA) in approximately 4.3 min of x-ray exposure using a RS320 Irradiation System (Gulmay Medical) The cells were returned to the cell culture incubator, and RNA was extracted from the cells 96 h post-radiation treatment (which corresponds to 120 h post-epirubicin treatment).

Figure 8:
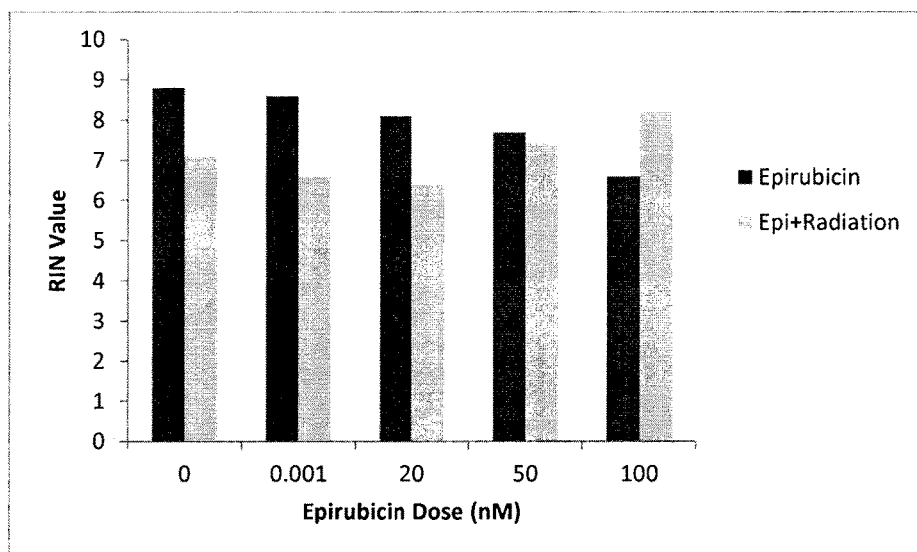
FIG. 8: Graphs of A2780 cells were treated with increasing doses of Epirubicin with and without 10 Gy radiation. A) RIN value vs. Epirubicin Dose; B) RDI value vs. Epirubicin Dose; C) RNA concentration vs. Epirubicin Dose.
Figure 8:
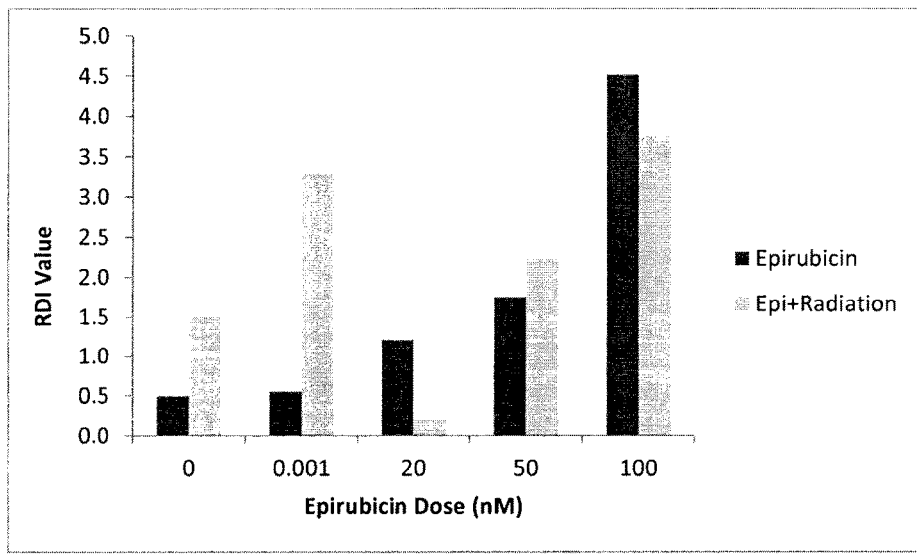
Figure 8:
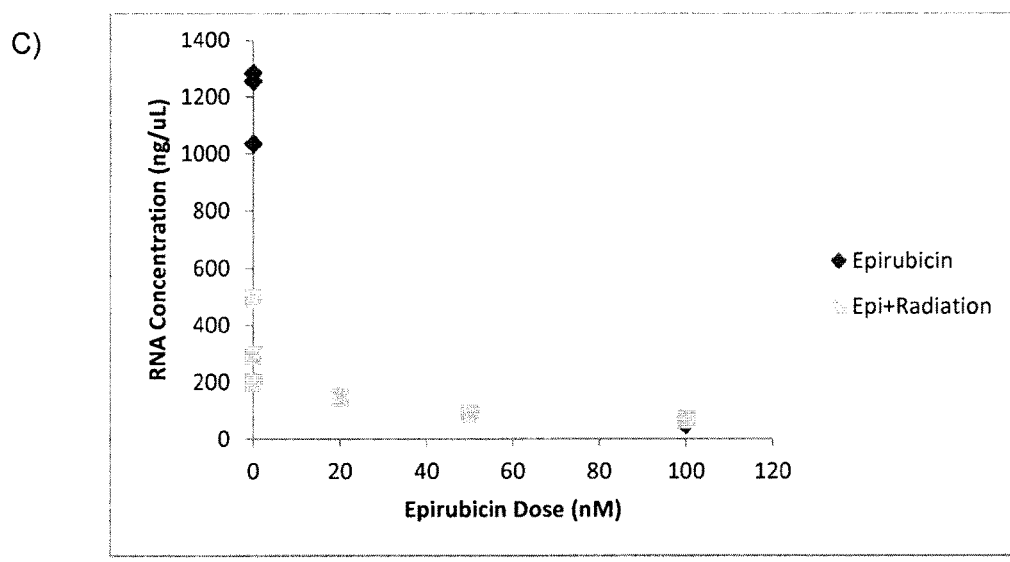

FIG. 8A shows RIN values versus Epirubicin dose. A loss in RIN value is seen with radiation at low doses of Epirubicin.

FIG. 8B shows RDI values vs Epirubicin dose. RDI values increase with radiation at low drug doses.

FIG. 8C shows RNA concentration vs. Epirubicin Dose and demonstrates an increased loss in RNA concentration with radiation at low drug doses.

The low banding region can also be trisected into several regions including the "low C", "low B" and "low A" sub-regions or banding regions as demonstrated in FIG. 12 for use in some RDA methods. It has been found that the low A banding region may contain RNA due to autolytic degradation as well as due to other effects and that the low C banding region is an important region in assessing the effect on RNA due to various external stimuli such as cytotoxic treatments, for example. It has also been found that in response to certain drugs, the RNA starts to spread to the low C banding region, then to the low B banding region and then to the low A banding region. The low C banding region is a range between 35 seconds and a start of the 18S peak.

Figure 9:
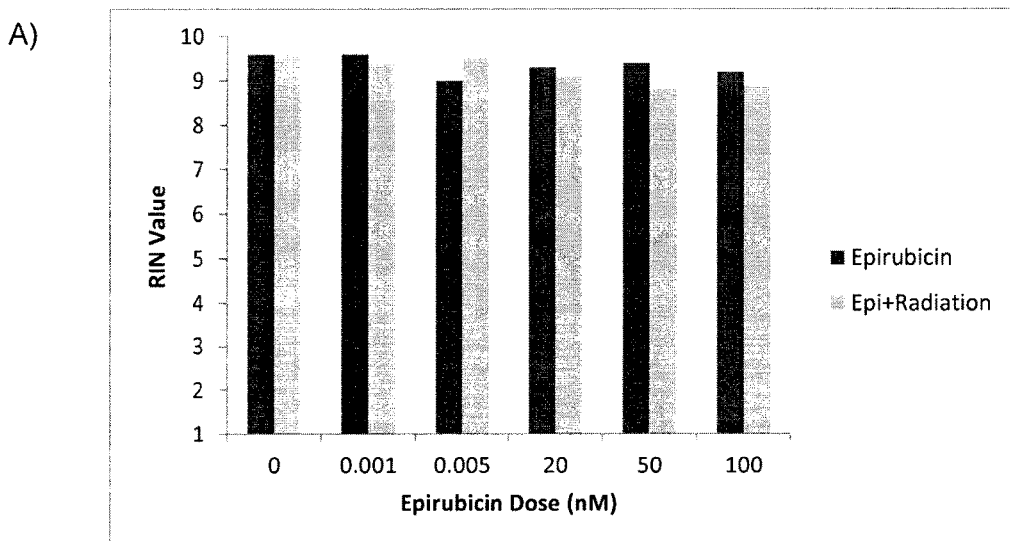
FIG. 9: Graphs of MCF-7 cells were treated with increasing doses of Epirubicin with and without 10 Gy radiation. A) RIN value vs. Epirubicin; B) RDI value vs. Epirubicin; C) RNA concentration vs. Epirubicin Dose.
Figure 9:
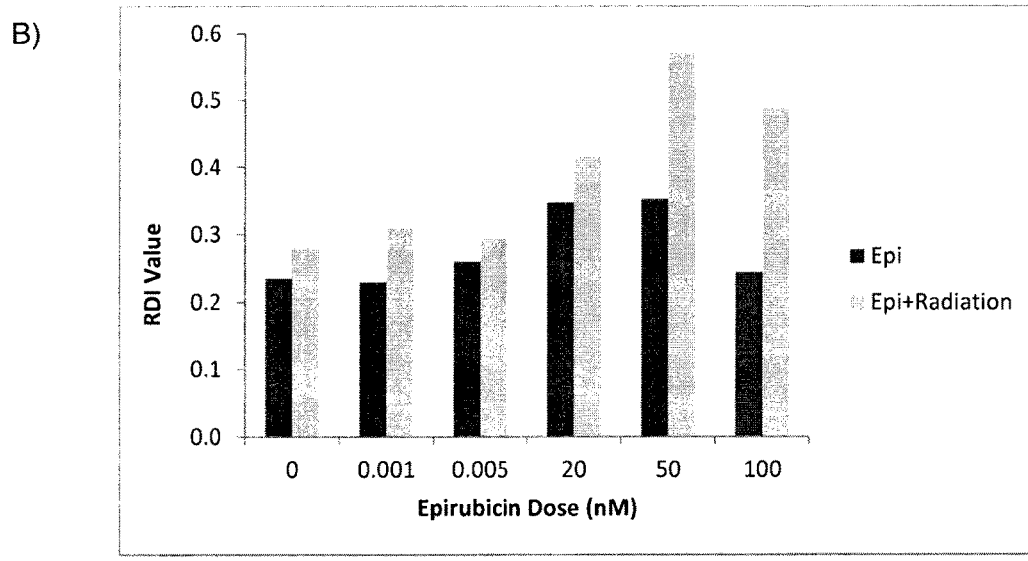
Figure 9:
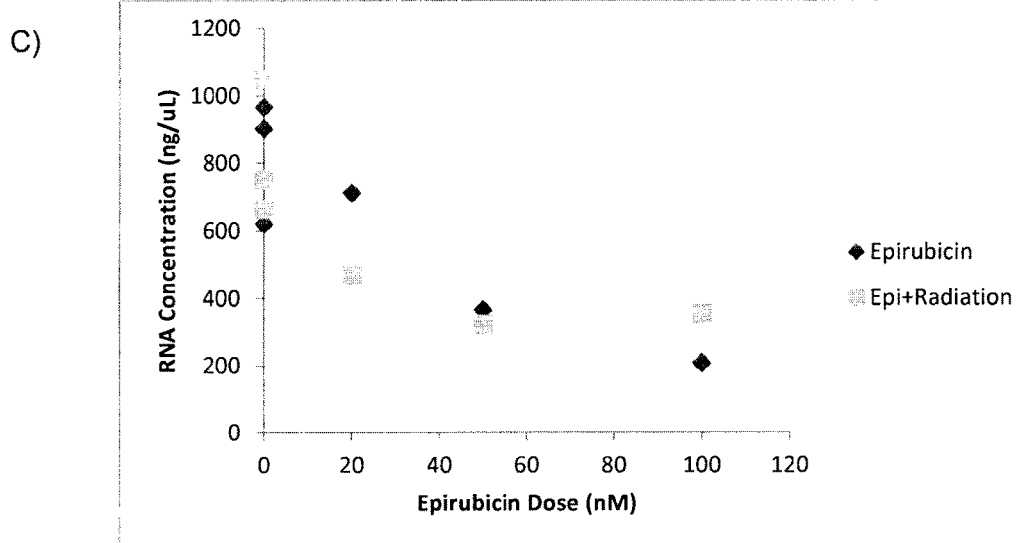

FIG. 9A shows RIN value vs. Epirubicin Dose and demonstrates a loss in RIN value when combined with radiation.

Both MCF-7 and SkBr3 cells had a 45% increase in RDI with 2 Gy of radiation only. RDI is more sensitive and the RNA degradation effect is less evident as a change in the RIN value.

FIG. 9B shows RDI value vs. Epirubicin Dose and demonstrates an increase in RDI value with radiation up to 100 uM Epirubicin. FIG. 9C shows RNA concentration vs. Epirubicin Dose and demonstrates a loss in RNA concentration with increasing doses of Epirubicin. RDI is more sensitive than RIN in measuring radiation induced effects.

In another experiment, A2780 cells were treated with 5 nM Docetaxel, 10 Gy Radiation and 10 Gy Radiation+5 nM Docetaxel for 72 hours or 96 hours. The results demonstrate that signal induced RNA degradation is time-dependent.

Figure 10:
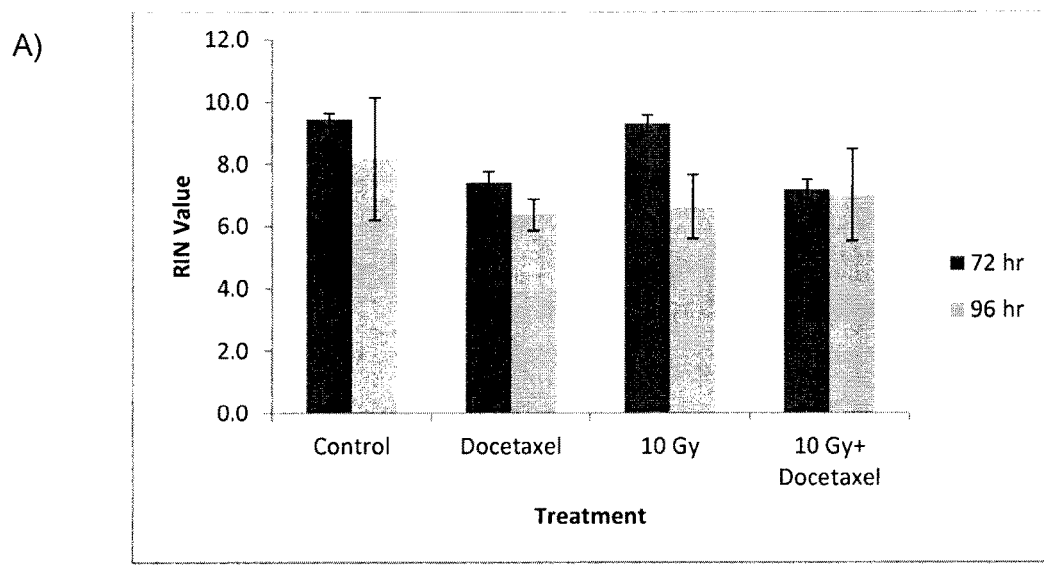
FIG. 10: Graphs of A2780 cells treated with 5 nM Docetaxel, 10 Gy Radiation and 10 Gy Radiation+5 nM Docetaxel at 72 hours and 96 hours. A) Mean RIN value with drug and radiation treatment (n=3). Error bars represent std deviation; B) Mean RDI value with Docetaxel and radiation treatment (n=3) suggest an increase in RDI value with radiation+Docetaxel compared with Docetaxel alone at 96 hr. Error bars represent standard deviation.
Figure 10:
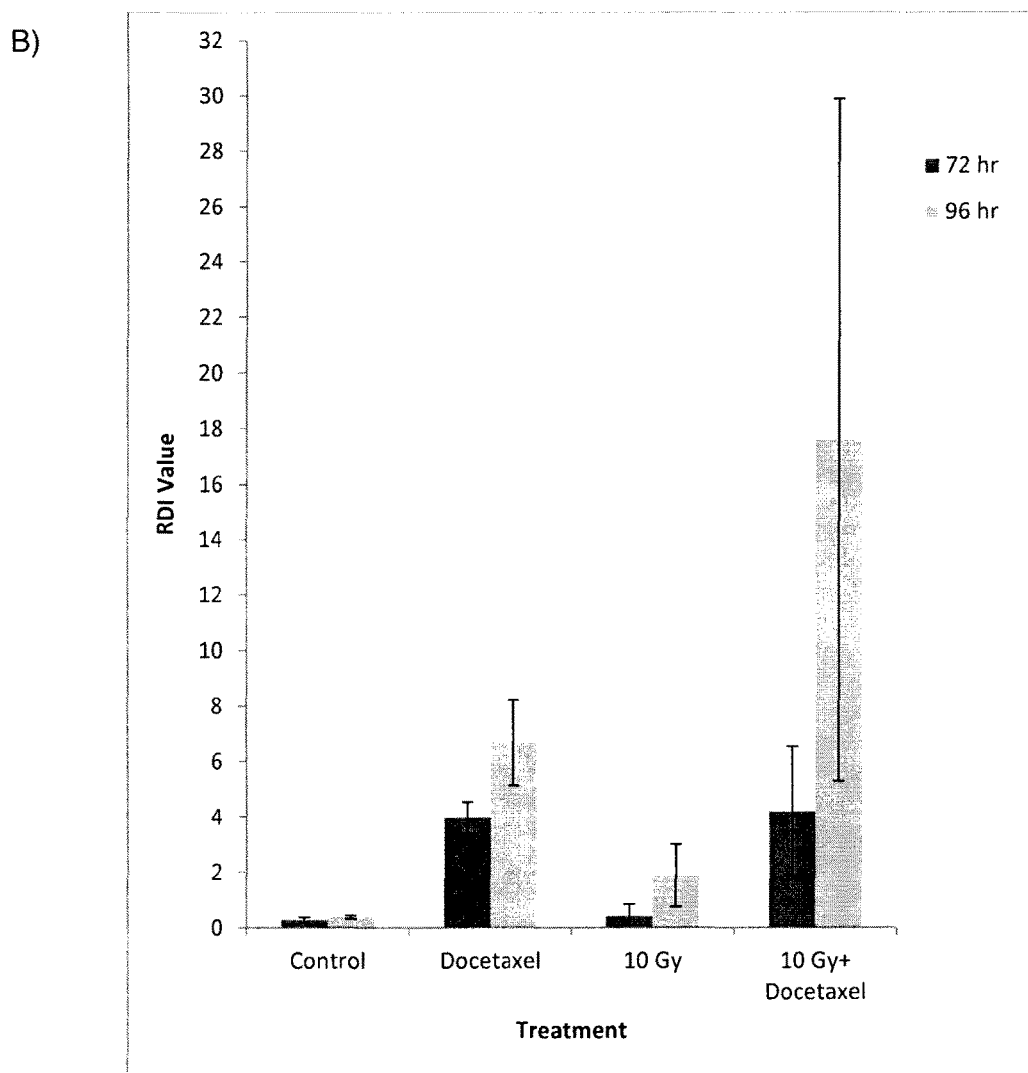

FIG. 10A provides the mean RIN value versus drug and radiation treatment (n=3). Error bars represent standard deviation. FIG. 10A shows an increased loss in RIN value with radiation+Docetaxel at 72 hr.

FIG. 10B provides the mean RDI value versus Docetaxel and radiation treatment (n=3). The results suggest an increase in RDI value with radiation+Docetaxel compared with Docetaxel alone at 96 hr. Error bars represent standard deviation.

Example 4

Electropherogram data obtained from patients in Example 1 was reanalyzed by calculating RDI values. The RDI values were calculated using features (Intermediate Area+LowC Area)/(28S Area+18S Area).

Figure 11:
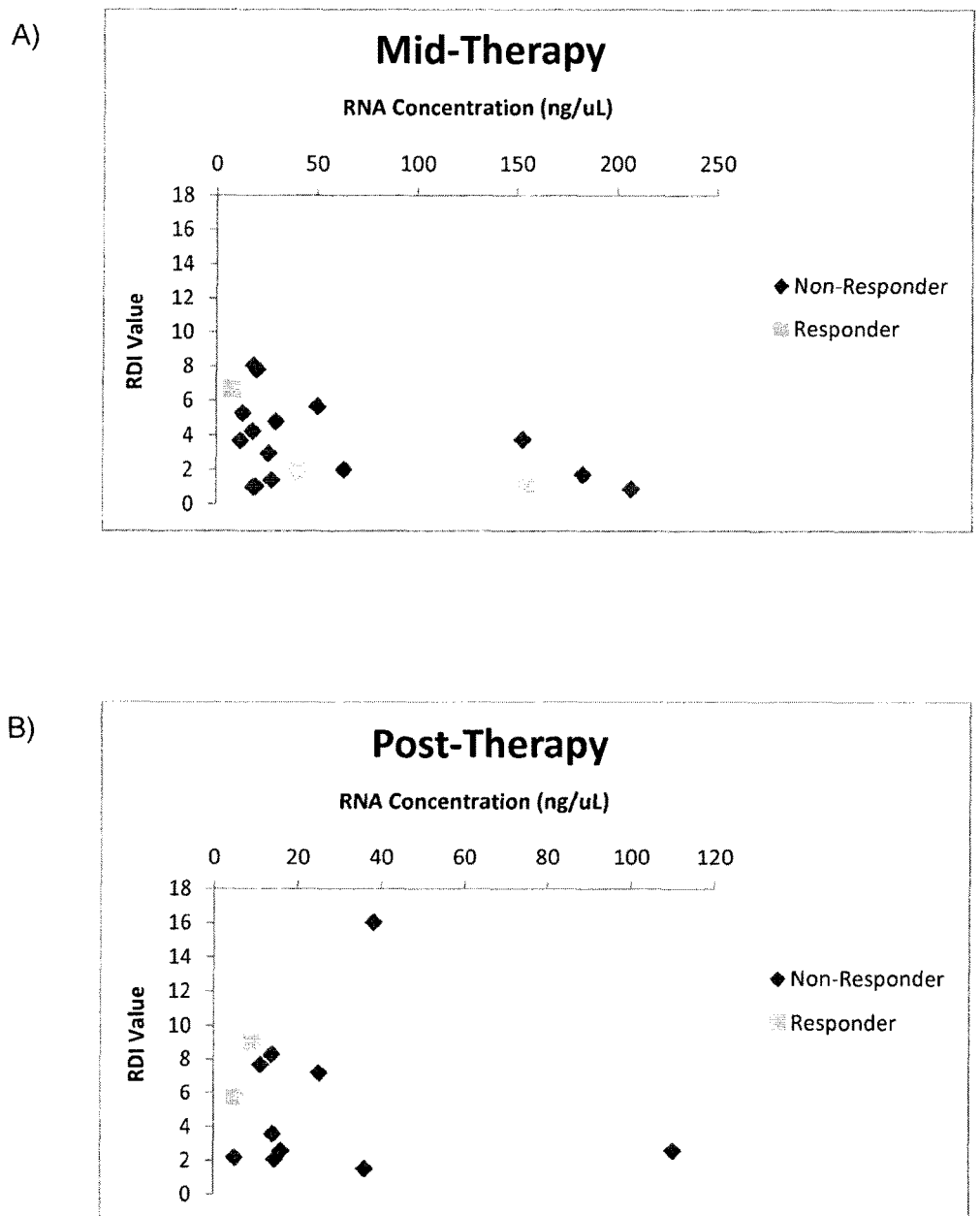
FIG. 11: Graphs of RDI versus RNA concentration of pCR responders and pCR non-responders for samples taken (A) mid therapy and (B) post therapy.

FIG. 11 plots RNA concentration versus RDI values for A) mid-treatment (before radiation) and B) post treatment samples (after radiation).

Based on the above, an RDI value of 3 or less may indicate non-response to radiation. For example, FIG. 11 b shows that post-treatment samples which had a RDI vaule of 3 or less are non-responders to the radiation/docetaxel combination. High RNA concentration and low RDI are suggestive of non-response post treatment.

Example 5

A2780 ovarian cancer cells were treated with radiation of 2 to 10 Gray using a Gulmay RS320 Irradiation System and subsequently harvested after 24, 48 and 72 hr. RNA was isolated and run on an Agilent Bioanalyzer. Analysis of the electropherogram demonstrated that an increase in the ratio Intermediate Area/(28S+18S Areas) at 72 hours is detectable in radiation treated cells. For example, cells treated at 10 Gray for 72 hours show radiation induced RNA degradation in the intermediate region and the low banding region, but not much difference in the area of the electropherogram where the autolysis peak resides. Radiation induced RNA degradation is evident at 72 hrs at both dose levels.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

CITATIONS FOR REFERENCES REFERRED TO IN THE SPECIFICATION

1. Canadian Cancer Society. Canadian Cancer Statistics. http://www cancer ca/vgn/images/portal/cit_86751114/10/34/614137951cw_library_WYNTK_Bladder_Punjabi2005 pdf [2008 Available from: URL:www.cancer.ca
2. Kuerer H M, Newman L A, Smith T L, Ames F C, Hunt K K, Dhingra K et al. Clinical course of breast cancer patients with complete pathologic primary tumor and axillary lymph node response to doxorubicin-based neo-adjuvant chemotherapy. J Clin Oncol 1999; 17(2):460-469.
3. Formenti S C, Dunnington G, Uzieli B, Lenz H, Keren-Rosenberg S, Silberman H et al. Original p53 status predicts for pathological response in locally advanced breast cancer patients treated preoperatively with continuous infusion 5-fluorouracil and radiation therapy. Int J Radiat Oncol Biol Phys 1997; 39(5):1059-1068.
6. Scholl S M et al. Breast tumours response to primary chemotherapy predicts local and distant control as well as survival. Eur J Ca 1995; 31A: 1969-1995.
7. Chollet P et al. Clinical and pathological response to primary chemotherapy in operable breast cancer. Eur J Ca 1997; 33: 862-866.
8. Gazet J C et al. Assessment of the effect of pretreatment with neoadjuvant therapy on primary breast cancer. Br J Ca 1996; 73: 758-762.
9. Bissery M C et al. Experimental antitumor activity of Taxotere (RP 56976, NCS 628503) a Taxol analogue. Ca Res 1991; 51: 4845-4852.
10. Ganansia-Leymarie V et al. Signal transduction pathways of taxane-induced apoptosis. Curr Med Chem Antica Ag 2003; 3: 291-306.
11. Valero V et al. Phase II trial of docetaxel: a new highly effective antineoplastic agent in the management of patients with anthracycline-resistant metastatic breast cancer. JCO 1995; 13: 2886-2894.
12. Ravdin P M et al. Phase II trial of docetaxel in advanced anthracycline-resistant or anthracenedione-resistant breast cancer. JCO 1995; 13: 2879-2885.
13. Chan S et al. Prospective randomized trial of docetaxel versus doxorubicin in patients with metastatic breast cancer. The 303 Study Group. JCO 1999; 17: 2341-2354.
14. Nabholtz J M et al. Docetaxel and doxorubicin compared with docetaxel and cyclophosphamide as first-line chemotherapy for metastatic breast cancer: results of a randomized, multicenter phase III trial. JCO 2003; 21: 968-975.
15. O'Shaughnessy J et al. Superior survival with capecitabine plus docetaxel combination therapy in anthracycline-pretreated patients with advanced breast cancer; phase III trial results. JCO 2002; 20: 2812-2823.
16. Rivera E et al. Phase 3 study comparing the use docetaxel on an every-3-week versus weekly schedule in the treatment of metastatic breast cancer. Cancer 2008; 112: 1455-1461.

17. Roche H et al. Sequential adjuvant epirubicin-based and docetaxel chemotherapy for node-positive breast cancer patients; the FNCLCC PACS 01 trial. JCO 2006; 24: 5664-5671.
18. Martin M et al. Adjuvant docetaxel for node-positive breast cancer. NEJM 2005; 352: 2302-2313.
19. Amat S et al. Induction chemotherapy in operable breast cancer: high pathological response rate induced by docetaxel. Proc Am Soc Clin Onc 1999; 18: 79a, abstract 297.
20. Tubiana-Hulin M et al. Phase II trial combining docetaxel (D) doxorubicin (DOX) as neoadjuvant treatment in patients (Pts) with operable breast carcinoma (BC). Proc Am Soc Clin Onc 2000; 19: 127a, abstract 492.
21. Limentani S A et al. Phase II study of doxorubicin and docetaxel as neoadjuvant therapy for women with stage IIB or III breast cancer. Proc Am Soc Clin Onc 2000; 19: 131a, abstract 511.
22. Teston L et al. Dose-dense chemotherapy with sequential doxorubicin (D) and docetaxel (Dt) for intial treatment of operable and inoperable stage II-IIIb breast cancer. Proc Am Soc Clin Onc 2000; 19: 134a, abstract 524.
23. Wynendale W et al. Neoadjuvant chemotherapy with sequential doxorubicin (DOX) and docetaxel (DOC) in locally advanced breast cancer (LABC): a pilot study. Proc Am Soc Clin Onc 1999; 18: 106a, abstract 389.
24. Bear H D et al. the effect on tumor response of adding sequential preoperative docetaxel to preoperative doxorubicin and cyclophosphamide: preliminary results from National Surgical Adjuvant Breast and Bowel Project protocol B-27. JCO 2003; 21: 4165-4174.
25. Smith I C et al. Neoadjuvant chemotherapy in breast cancer significantly enhanced response with docetaxel. JCO 2002; 20: 1456-1466.
26. Hutcheon A W et al. Improvements in survival in patients receiving primary chemotherapy with docetaxel for breast cancer: a randomized controlled trial. Br Ca Res Tr 2001; 69: 298.
27. Von Minckwitz G et al. Doxorubicin with cyclophosphamide followed by docetaxel every 21 days compared with doxorubicin and docetaxel every 14 days as preoperative treatment in operable breast cancer: the GEPAR-DUO study of the German Breast Group. JCO 2005; 23: 2676-2685.
28. Sauer R et al. Preoperative versus postoperative chemoradiotherapy for rectal cancer. NEJM 2004; 351: 1731-1740.
29. Bosset J F et al. Chemotherapy with preoperative radiotherapy in rectal cancer. NEJM 2006; 355: 1114-1123.
30. Rodel C et al. Prognostic significance of tumor regression after preoperative chemoradiotherapy for rectal cancer. JCO 2005; 23: 8688-8696.
31. Adelstein D J et al. An Intergroup phase III comparison of standard radiation therapy and two schedules of concurrent chemoradiotherapy in patients with unresectable squamous cell head and neck cancer. JCO 2003; 21: 92-98.
32. Denis F et al. Final results of the 94-01 French Head and Neck Oncology and Radiotherapy Group randomized trial comparing radiotherapy alone with concomitant radiochemotherapy in advanced-stage oropharynx carcinoma. JCO 2004; 22: 69-76.
33. Forastiere A A et al. Concurrent chemotherapy and radiotherapy for organ preservation in advanced laryngeal cancer. NEJM 2003; 349: 2091-2098.
34. Posner M R et al. Cisplatin and Fluorouracil alone or with docetaxel in head and neck cancer. NEJM 2007; 357: 1705-1715.
35. Furuse K et al. Phase III study of concurrent versus sequential thoracic radiotherapy in combioation with mitomycin, vindesine and cisplatin in unresectable stage III non-small cell lung cancer. JCO 1999; 17: 2692-2699.
36. Curran W et al. Phase III comparison of sequential versus concurrent chemo-radiation for patients with unresected stage III non-small cell lung cancer (NSCLC): report of Radiation Oncology Group (RTOG) 9410. Lung Ca 2003; 29 (suppl 1): 93, abstract 303.
37. Pierre F et al. a randomized phase III trial of sequential chemo-radiotherapy versus concurrent chemo-radiotherapy in locally advanced non-small cell lung cancer (NSCLC) (GLOT-GFPC NPC 95-01 study). Proc Am Soc Clin Onc 2001; 20: 312a, abstract 1246.
38. Zatloukal P V et al. Concurrent versus sequential radiochemotherapy with vinorelbine plus cisplatin (V-P) in locally advanced non-small cell lung cancer. A randomized phase II study. Proc Am Soc Clin Onc 2002; 21: 290a, abstract 1159.
39. Mauer A M et al. Phase I study of docetaxel with concomitant thoracic radiation therapy. JCO 1998; 16: 159-164.
40. Mudad R et al. Concomitant docetaxel, cisplatin and radiation (XRT) in the treatment of locally advanced non-small cell lung cancer (NSCLC): a phase I study. Proc Am Soc Clin Onc 2000; 19: 544a.
41. Koukourakis M I et al. Weeky docetaxel and concomitant boost radiotherapy for non-small cell lung cancer. A phase I/II dose escalation trial. Eur J Ca 1998; 34: 838-844.
42. Ramlan R et al. Randomized phase II study evaluating the feasibility of thoracic radiotherapy with or without weekly docetaxel (Taxotere®) following induction chemotherapy with cisplatin and docetaxel in unresectable stage III A-B non-small cell lung cancer. ESMO Congress 2002; Poster 491.
43. Wu H G et al. Phase I study of weekly docetaxel and cisplatin concurrent with thoracic radiotherapy in stage III non-small cell lung cancer. Int J Rad Onc Bio Phys 2002; 52: 75-80.
44. Onishi H et al. Concurrent two-dimensional radiotherapy and weekly docetaxel in the treatment of stage III non-small cell lung cancer: a good local response but no good survival due to radiation pneumonitis. Lung Ca 2003; 40: 79-84.
45. Bellon J R et al. Concurrent radiation therapy and paclitaxel or docetaxel chemotherapy in high-risk breast cancer. Int J Rad Onc Bio Phys 2000; 48: 393-397.
46. Formenti S C et al. Preoperative twice-weekly paclitaxel with concurrent radiation therapy followed by surgery and postoperative doxorubicin-based chemotherapy in locally advanced breast cancer: a phase I/II trial. JCO 2003; 21: 864-870.
48. Brewer-Goufbely Y P et al. Neoadjuvant concurrent chemoradiotherapy (CT-RT) with paclitaxel (TAXOL) and 5-fluorouracil (5-FU) followed by epirubicin-cyclophosphamide (FEC) and surgery in patients (Pts) with locally advanced breast cancer (LABC). Proc Am Soc Clin Onc 2001; 20, abstract 1815.
49. Roche H, Fumoleau P, Spielmann M, Canon J L, Delozier T, Serin D et al. Sequential adjuvant epirubicin-based and docetaxel chemotherapy for node-positive breast cancer patients: the FNCLCC PACS 01 Trial. J Clin Oncol 2006; 24(36):5664-5671.

50. Tabernero J, Climent M A, Lluch A, Albanell J, Vermorken J B, Barnadas A et al. A multicentre, randomised phase II study of weekly or 3-weekly docetaxel in patients with metastatic breast cancer. Ann Oncol 2004; 15(9): 1358-1365.
51. Rivera E, Mejia J A, Arun B K, Adinin R B, Walters R S, Brewster A et al. Phase 3 study comparing the use of docetaxel on an every-3-week versus weekly schedule in the treatment of metastatic breast cancer. Cancer 2008; 112(7):1455-1461.
52. A. Schroeder, O. Mueller, S. Stocker, R. Salowsky, M. Leiber, M. Gassmann, S. Lightfoot, W. Menzel, M. Granzow, and T. Ragg, The RIN: an RNA integrity number for assigning integrity values to RNA measurements, BMC. Mol. Biol. 7 (2006) 3.
53. A. M. Parissenti, J. A. Chapman, H. J. Kahn, B. Guo, L. Han, P. O'Brien, M. P. Clemons, R. Jong, R. Dent, B. Fitzgerald, K. I. Pritchard, L. E. Shepherd, and M. E. Trudeau, Association of low tumor RNA integrity with response to chemotherapy in breast cancer patients, Breast Cancer Res.Treat. 119 (2010) 347-356.
54. C. Cera, G. Palu, S. M. Magno, and M. Palumbo, Interaction between second generation anthracyclines and DNA in the nucleosomal structure, Nucleic Acids Res. 19 (1991) 2309-2314.
55. S. Spadari, G. Pedrali-Noy, F. Focher, A. Montecucco, T. Bordoni, C. Geroni, F. C. Giuliani, G. Ventrella, F. Arcamone, and G. Ciarrocchi, DNA polymerases and DNA topoisomerases as targets for the development of anticancer drugs, Anticancer Res. 6 (1986) 935-940.
56. N. R. Bachur, F. Yu, R. Johnson, R. Hickey, Y. Wu, and L. Malkas, Helicase inhibition by anthracycline anticancer agents, Mol.Pharmacol. 41 (1992) 993-998.
57. R. Olinski, P. Jaruga, M. Foksinski, K. Bialkowski, and J. Tujakowski, Epirubicin-induced oxidative DNA damage and evidence for its repair in lymphocytes of cancer patients who are undergoing chemotherapy, Mol.Pharmacol. 52 (1997) 882-885.
58. U. Vaishampayan, R. E. Parchment, B. R. Jasti, and M. Hussain, Taxanes: an overview of the pharmacokinetics and pharmacodynamics, Urology 54 (1999) 22-29.
59. D. L. Morse, H. Gray, C. M. Payne, and R. J. Gillies, Docetaxel induces cell death through mitotic catastrophe in human breast cancer cells, Mol.Cancer Ther. 4 (2005) 1495-1504.
60. T. Wieder, F. Essmann, A. Prokop, K. Schmelz, K. Schulze-Osthoff, R. Beyaert, B. Dorken, and P. T. Daniel, Activation of caspase-8 in drug-induced apoptosis of B-lymphoid cells is independent of CD95/Fas receptor-ligand interaction and occurs downstream of caspase-3, Blood 97 (2001) 1378-1387.
61. Mueller, O. L. S. Schroeder, A (2004) RNA Integrity Number (RIN)—Standardization of RNA Quality Control.
62. Agilent 2100 Bioanalyzer,Agilent Technologies, Inc.2100 Expert User's Guide. Agilent Technologies Hewlett-Packard Str. 876337 Waldbronn Germany, Agilent Technologies, Inc. . Agilent2100 G2946-90004_Vespucci_UG_eBook_(NoSecPack)[2].
63. F Xia and S N Powell, 2002. "The molecular basis of radiosensitivity and chemosensitivity in the treatment of breast cancer". Semin Radiat Oncol (2002), 12(4) 296-304.
64. Hu, Z-P et al., 2012. "Metabolomic response of human skin tissue to low dose ionizing radiation". Mol BioSyst 8; 1979-1986.
65. Delic, J. et al., 1993. "Gamma-ray induced transcription and apoptosis-associated loss of 28S rRNA in interphase human lymphocytes". Int J Radiat Biol 64; 39-46.
66. Al-Mayah, A. H. J. et al., 2012. "Possible role of exosomes containing RNA in mediating nontargeted effect of ionizing radiation". Radiat Research 177; 539-545.
67. Krolak, J. M. et al., 1989. "18S Ribosomal RNA is Degraded during Ribosome Maturation in Irradiated HeLa cells". Radiat Research 118; 330-340.

The invention claimed is:

1. A method of treating a patient receiving a cancer treatment regimen comprising radiation, the method comprising:
   a. obtaining isolated RNA of a cancer cell sample from a patient who has received one or more doses of radiation for cancer treatment; the isolated RNA comprising radiation induced degraded RNA and intact RNA;
   b. separating the isolated RNA through a separation channel of a RNA chip using an analytic microcapillary electrophoresis system where intercalating fluorescent dye binds the RNA and detecting the isolated RNA by detecting the fluorescent dye; wherein the detecting is recorded in an electropherogram dataset;
   c. measuring the amount of degraded RNA and intact RNA, the measuring comprising:
      locating a dye-only peak, an 18S peak, and a 28S peak, and determining an intermediate region and a low C banding region, where the dye-only peak is at about 22.5 seconds, the intermediate region is the region of the electropherogram between the located 18S and 28S peaks, and the low C banding region is the region between 35 seconds and a start of the 18S peak; and
      determining values for the 18S peak area, the 28S peak area, and at least one of the intermediate region area and the low C banding region area;
   d. determining an RNA Disruption assay (RDA) score for the cancer cell sample, the RDA score comprising: (1) a ratio of the intermediate area to a sum of the 28S peak area and the 18S peak area; (2) a ratio of the low C banding region area to the sum of the 28S peak area and the 18S peak area; or (3) a ratio of the sum of the low C banding region area and the intermediate area to the sum of the 28S peak area and the 18S peak area;
   e. comparing the RDA score determined for the cancer cell sample to at least one RDA score threshold determined from a plurality of samples from responders to the cancer treatment regimen comprising radiation or non-responders to the cancer treatment regimen comprising radiation, and;
   f. detecting that the RDA score determined for the cancer cell sample is at least as high as the RDA score threshold determined from a plurality of responders, and continuing the cancer treatment regimen comprising radiation; or
      detecting that the RDA score determined for the cancer cell sample is lower than the RDA score threshold determined from a plurality of responders, or lower than the RDA score threshold determined from a plurality of non-responders, and changing the cancer treatment regimen comprising radiation, the changing selected from increasing the dosage level and/or schedule of the radiation, adding a chemotherapeutic agent, biologic or radiosensitizing agent to the treatment, or changing to an alternate cancer drug therapy or surgery.

2. The method of claim 1, further comprising measuring RNA concentration.

3. The method of claim 1, wherein the cancer cells have received 1, 2, 3, 4, 5, 6 or more doses of radiation.

4. The method of claim 1, wherein cells of the cancer cell sample are treated with a dose of a chemotherapeutic agent, prior to, concurrently and/or subsequent to the radiation treatment, optionally wherein the chemotherapeutic agent is selected from anthracyclines, taxanes and combinations thereof, preferably wherein the chemotherapeutic agent comprises epirubicin, docetaxel or combinations thereof; optionally wherein the taxane is selected from paclitaxel, docetaxel, larotaxel, Abraxane, docoxahexaenoic acid-linked paclitaxel, paclitaxel polyglumex, Ortataxel, Genexol, liposomal-encapsulated paclitaxel, and paclitaxel in a Vitamin E emulsion.

5. The method of claim 1, wherein the cells are treated with a test agent prior to the radiation treatment to determine if the test agent is a radiosensitizer or a radio protector.

6. The method of claim 1, wherein the RDA score threshold, is more than one RDA score thresholds defining multiple zones, the RDA score thresholds derived from a plurality of unresponsive samples and responsive samples.

7. The method of claim 1, wherein the cancer cell sample is a breast cancer cell sample obtained from a breast cancer patient, or an ovarian cancer cell sample obtained from an ovarian cancer patient, optionally wherein the breast cancer is Her2+, basal subtype or luminal B subtype and/or wherein the breast cancer patient has locally advanced breast cancer (LABC).

8. The method of claim 6, wherein the RDA score thresholds define 3 zones stratified for risk.

9. The method of claim 6, wherein the cancer cell sample is a breast cancer cell sample obtained from a breast cancer patient, or an ovarian cancer cell sample obtained from an ovarian cancer patient, optionally wherein the breast cancer is Her2+, basal subtype or luminal B subtype and/or wherein the breast cancer patient has locally advanced breast cancer (LABC).

10. The method of claim 7, wherein the RDA score threshold is more than one RDA score thresholds defining multiple zones, the RDA score thresholds derived from a plurality of unresponsive samples and responsive samples.

11. The method of claim 1, wherein the changed treatment comprises treating the patient with a chemotherapeutic agent, selected from taxane chemotherapeutics, anthracyclines and combinations thereof, optionally wherein the taxane is selected from paclitaxel, docetaxel, larotaxel, Abraxane, docoxahexaenoic acid-linked paclitaxel, paclitaxel polyglumex, Ortataxel, Genexol, liposomal-encapsulated paclitaxel, and paclitaxel in a Vitamin E emulsion.

12. The method of claim 1, wherein two or more cancer cell samples are obtained from the subject and assayed and an average or maximum RDA score is determined.

13. The method of claim 1, wherein the method further comprises:
   a) exposing the patient with cancer to a radiation dose;
   b) obtaining a cancer cell sample after administration of the radiation dose, wherein said cancer cell sample is processed for obtaining the isolated RNA.

14. The method of claim 1, wherein the changed treatment comprises treating the patient with an increased radiation treatment dose and/or schedule.

15. The method of claim 1, comprising:
   obtaining the cancer cell from the patient who has received one or more doses of radiation for cancer treatment, and wherein the RDA score determined for the cancer cell sample is lower than the RDA score threshold determined from a plurality of responders, or lower than the RDA score threshold determined from a plurality of non-responders, and changing the cancer treatment regimen comprises administration of a chemotherapeutic agent, alternate cancer drug therapy or surgery.

16. The method of claim 13, wherein the cancer cell sample is a breast cancer cell sample or an ovarian cancer cell sample.

\* \* \* \* \*